US012510538B2

(12) United States Patent
Stojanovic et al.

(10) Patent No.: US 12,510,538 B2
(45) Date of Patent: Dec. 30, 2025

(54) STEM-LOOP RECEPTOR-BASED FIELD-EFFECT TRANSISTOR SENSOR DEVICES FOR SMALL-MOLECULE TARGET DETECTION UNDER PHYSIOLOGICAL SALT CONCENTRATIONS

(71) Applicants: THE TRUSTEES OF COLUMBIA UNIVERSITY IN THE CITY OF NEW YORK, New York, NY (US); THE REGENTS OF THE UNIVERSITY OF CALIFORNIA, Oakland, CA (US)

(72) Inventors: Milan Stojanovic, Ridgewood, NJ (US); Anne Milasincic Andrews, Los Angeles, CA (US); Kyungae Yang, New York, NY (US); Paul S. Weiss, Los Angeles, CA (US); Nako Nakatsuka, Adliswill (CH)

(73) Assignees: THE TRUSTEES OF COLUMBIA UNIVERSITY IN THE CITY OF NEW YORK, New York, NY (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1175 days.

(21) Appl. No.: 17/175,190

(22) Filed: Feb. 12, 2021

(65) Prior Publication Data

US 2021/0223240 A1 Jul. 22, 2021

Related U.S. Application Data

(63) Continuation of application No. PCT/US2019/046891, filed on Aug. 16, 2019.

(60) Provisional application No. 62/765,162, filed on Aug. 17, 2018.

(51) Int. Cl.

| | |
|---|---|
| ***G01N 33/543*** | (2006.01) |
| ***C12Q 1/6825*** | (2018.01) |
| ***C12Q 1/6869*** | (2018.01) |
| ***G01N 27/414*** | (2006.01) |
| ***G01N 33/68*** | (2006.01) |

(52) U.S. Cl.

CPC ..... *G01N 33/54373* (2013.01); *C12Q 1/6825* (2013.01); *C12Q 1/6869* (2013.01); *G01N 27/4145* (2013.01); *G01N 27/4148* (2013.01); *G01N 33/6818* (2013.01)

(58) Field of Classification Search

CPC ......... G01N 33/54373; G01N 27/4145; G01N 27/4148; G01N 33/6818; C12Q 1/6825; C12Q 1/6869; C12Q 2525/205; C12Q 2525/301; C12N 2310/16; C12N 2310/3517; C12N 2320/13; C12N 15/115

See application file for complete search history.

(56) References Cited

FOREIGN PATENT DOCUMENTS

| | | |
|---|---|---|
| WO | WO 2009/012420 A1 | 1/2009 |
| WO | WO 2017/210683 A1 | 12/2017 |

OTHER PUBLICATIONS

Goda et al, A hairpin DNA aptamer for a filed coupled with groove binders as a smart switch for a field-effect transistor biosensor, Biosensors and Bioelectronics, 2012, 32 , pgs., 244-249. (Year: 2012).*

Vinalia et al, Smart DNA interfaces, Chem.Soc. Rev, 2014, 43, pp. 1612-1626 (Year: 2014).*

Kim et al., "Fabrication of High-Performance Ultrathin In2O3 Film Field-Effect Transistors and Biosensors Using Chemical Lift-Off Lithography," ACS Nano 2015 [Supporting Information].

Barhoumi et al., "Correlation of Molecular Orientation and Packing Density in a dsDNA Self-Assembled Monolayer Observable with Surface-Enhanced Raman Spectroscopy," J. Am. Chem. Soc. 130, 14040-14041 (2008).

Chen et al., "Quasi-Two-Dimensional Metal Oxide Semiconductors Based Ultrasensitive Potentiometric Biosensors," ACS Nano 11, 4710-4718 (2017).

Doering et al., "Single-Molecule and Single-Nanoparticle SERS: Examining the Roles of Surface Active Sites and Chemical Enhancement," J. Phys. Chem. B 106, 311-317 (2002).

Hu et al., "A simple and rapid approach for measurement of dissociation constants of DNA aptamers against proteins and small molecules via automated microchip electrophoresis," Analyst 136, 3461-3468 (2011).

International Search Report and Written Opinion for International Patent Application No. PCT/US2019/046891 dated Jan. 30, 2020.

Ishikawa et al., "A calibration method for nanowire biosensors to suppress device-to-device variation," ACS Nano 3, 3969-3976 (2009).

Kim et al., "Fabrication of High-Performance Ultrathin $In_2O_3$ Film Field-Effect Transistors and Biosensors Using Chemical Lift-Off Lithography," ACS Nano 9, No. 4, 4572-4582 (2015).

Kypr et al., "Circular dichroism and conformational polymorphism of DNA," Nucleic Acids Res. 37, 1713-1725 (2009).

Le Ru et al., "Single-Molecule Surface-Enhanced Raman Spectroscopy," Annu. Rev. Phys. Chem. 63, 65-87 (2012).

Moskovits, "Surface-enhanced Raman spectroscopy: a brief retrospective," J. Raman Spectrosc. 36, 485-496 (2005).

Neumann et al., "Direct Optical Detection of Aptamer Conformational Changes Induced by Target Molecules," Anal. Chem. 81, 10002-10006 (2009).

(Continued)

*Primary Examiner* — Narayan K Bhat

(74) *Attorney, Agent, or Firm* — Baker Botts L.L.P.

(57) ABSTRACT

Devices for detecting at least one target molecule in a sample are provided. The devices comprise a field-effect transistor and an aptamer attached to the field-effect transistor. The aptamer comprises a capture region and a stem region, wherein the target molecule can selectively bind to the capture region of the aptamer. The stem region can change a conformation of the aptamer when the capture region binds to the target molecule. Techniques for detecting a target molecule using such devices are also provided.

7 Claims, 49 Drawing Sheets

Specification includes a Sequence Listing.

(56) References Cited

OTHER PUBLICATIONS

Otto et al., "Surface-Enhanced Raman Spectroscopy of DNA Bases," J. Raman Spectrosc. 17, 289-298 (1986).

Pagba et al., "Direct detection of aptamer-thrombin binding via surface-enhanced Raman spectroscopy," J. Biomed. Opt. 15 047006 (2010).

Walsh et al., "Retention of function in the DNA homolog of the RNA dopamine aptamer," Biochem. Biophys. Res. Commun., 388 732-735 (2009).

Yang et al., "In vitro selection and amplification protocols for isolation of aptameric sensors for small molecules," Methods 106, 58-65 (2016).

Yang et al., "Recognition and Sensing of Low-Epitope Targets via Ternary Complexes with Oligonucleotides and Synthetic Receptors," Nat. Chem. 6, 1003-1008 (2014).

Yunker et al., "Suppression of the coffee-ring effect by shape-dependent capillary interactions," Nature 476, 308-311 (2011).

Zuker, "Mfold web server for nucleic acid folding and hybridization prediction," Nucleic Acids Res. 31, 3406-3415 (2003).

* cited by examiner

*D-glucose 6-phosphate*

Glucosamine hydrochloride

*N-acetyl-D-glucosamine*

1,2,5,6-di-*O*-Isopropyldiene-alpha-*D*-glucofuranose

Methyl alpha-*D*-glucopyranoside

Methyl beta-*D*-glucopyranoside 1-thlo-beta-*D*-glucopyranoside

3-*O*-methyl-*D*-glucopyranose

PCPA

PEPA

STEM-LOOP RECEPTOR-BASED FIELD-EFFECT TRANSISTOR SENSOR DEVICES FOR SMALL-MOLECULE TARGET DETECTION UNDER PHYSIOLOGICAL SALT CONCENTRATIONS

CROSS REFERENCE TO RELATED APPLICATION

This application is a continuation of International Patent Application No. PCT/US 2019/046891 filed Aug. 16, 2019, which claims the benefit of priority of U.S. Provisional Patent Application No. 62/765,162 filed Aug. 17, 2018, which are hereby incorporated by reference in their entirety.

GRANT INFORMATION

This invention was made with Government Support under Grant Nos. GM104960 and DA045550 awarded by the National Institutes of Health and Grant No. CCF1518715 awarded by the National Science Foundation. The Government has certain rights in the invention.

SEQUENCE LISTING

The instant application contains a Sequence Listing, which has been submitted electronically in ASCII format and is hereby incorporated by reference in its entirety. Said ASCII copy, created on Oct. 11, 2019, is named 070050_6481_SL.txt and is 29,540 bytes in size.

BACKGROUND

Certain field-effect transistors (FETs) can be useful in biosensing applications. Biosensors based on FETs can be constructed by immobilizing biomolecule receptors on the semiconductor surfaces of FETs. When biomolecules immobilized on FETs bind to targets (analytes), they can change the charge distribution of the semiconductor material of the FET. This change in the surface potential of a FET can gate the voltage between source and drain electrodes resulting in a change in the conductance of the FET. Accordingly, the binding of targets to biomolecule receptors can be detected by measuring changes in FET transconductance, which manifest as changes in source-drain currents.

Certain limitations have prevented the reduction to practice of biosensors based on biomolecule-receptor-functionalized FETs. When biomolecule-FETs are placed in common sensing environments containing high concentrations of ions, (e.g., physiological environments), the interactions between a biomolecule receptor and a target can occur far from the semiconductor surface, and thus there is little to no measurable change in transconductance. The distance wherein biomolecule-target interactions can influence transconductance is governed by the Debye length. Under high ionic strength conditions (e.g., body fluids and in vivo environments), the Debye length is less than 1 nm. Thus, some portion of charge change due to biomolecule receptor conformation rearrangement associated with target capture and/or added charge associated with receptor capture of highly charged targets can occur within or near the Debye length above the FET semiconductor surface. Certain types of biomolecule receptors, (e.g., antibodies), can be larger than 1 nm. When these large biomolecule receptors are used with FETs, target detection through binding can only occur in dilute ionic strength samples where the Debye length is increased. This need for highly dilute sample environments limits FET biosensor applications wherein direct sensing in high ionic strength environments is required, (e.g., in vivo).

Furthermore, certain small-molecule targets, which are ubiquitous in biology and other sensing applications, themselves possess little to no charge. To enable electronic FET detection of these small-molecule targets, highly charged, compact receptors that undergo substantial target-induced conformational changes can be required. Additionally, certain nearly neutral or neutral receptors can also enable FET detection through the displacement of the ions in the measurement medium. In either case, FETs can be sensitive to small changes in transconductance associated with biomolecule-target association.

Thus, there remains a need for techniques for electronic detection of small-molecule targets under physiological, high ionic strength conditions via changes in transconductance in FETs.

SUMMARY

The presently disclosed subject matter relates to devices and methods for the detection of small target molecules in a sample.

In certain embodiments, an exemplary sensor can include a field-effect transistor (FET) and an oligonucleotide. The oligonucleotide can be a compact, highly charged nucleic-acid receptor. The oligonucleotide can be coupled to a field-effect transistor. In some embodiments, the oligonucleotide can include a capture region and a stem region. The stem region can be positioned to transform a stem-loop structure of the oligonucleotide to a new conformation that involves movement of the stem and/or capture region (loop) when the capture region binds to the target molecule. For example, the conformation change can induce a change in the FET semiconductor conductance because the backbone of the oligonucleotide can move to or away from a semiconductor surface of a FET. The backbone can be a neutral backbone, a nearly neutral backbone, or a negatively charged backbone. In non-limiting embodiments, a negatively charged portion of the backbone can reposition toward or away from a surface of a FET. Such capture of a specific target can cause a change in FET transconductance.

In certain embodiments, the oligonucleotide can be an aptamer. An exemplary aptamer can include a stem and at least one loop. The at least one loop can include a capture region and the stem can include a complementary stem region. When the capture region binds to the target molecule, the loop can surround the target molecule (binding pocket). The loop movement can also induce movement in the stem. In non-limiting embodiments, the oligonucleotide stem-loop structure can be transformed into a new conformation within one or a few Debye lengths from the surface, wherein the Debye length ranges from about 0.5 nm to about 3 nm in physiological conditions. In some embodiments, the loop can include a secondary structure. The secondary structure can include a base-paired structure that is configured to be formed by folding.

In certain embodiments, the oligonucleotide can further include molecules that amplify the charge of the oligonucleotide. For example, molecules that amplify the charge of the oligonucleotide can be selected from non-binding oligonucleotides, particles, dendrimers, organic species that have less than 1000 D molecular weight, or fragments that attract other species as amplifiers and combination thereof.

In certain embodiments, a certain portion of the aptamer conformation change occurs close enough to the semiconductor surface so that a change in transconductance occurs.

Detection can occur by moving charges of the aptamer or by displacing charges in the surrounding medium. In some embodiments, the target molecule can include glucose, hydrocortisone, phenylalanine, dehydroisoandrosterone, deoxycortisone, testosterone, aldosterone, dopamine, norepinephrine, sphingosine-1-phosphate, serotonin, melatonin, tyrosine, tobramycin, amikacin, methylene blue, ammonium, boronic acid, epinephrine, creatinine, urea, lithium, glycine, gamma-aminobutyric acid (GABA), glutamate, glutamine, tryptophan, tyrosine, and combinations thereof.

In certain embodiments, the disclosed field-effect transistor can include a metal oxide. In some embodiments, the disclosed field-effect transistor can include an organic conducting polymer, a carbon material, or a combination thereof. For example, the carbon material can be graphene or nanotubes. In non-limiting embodiments, the field-effect transistor can be a quasi-two-dimensional field-effect transistor.

In certain embodiments, the disclosed subject matter provides methods for detecting or measuring the presence and/or amount of a target molecule in a sample. An example method can include contacting an aptamer on a surface of a field-effect transistor with at least a portion of a sample and detecting a conductance change in the field-effect transistor. The stem region of the aptamer can induce a second conformation when the capture region of the aptamer binds to the target molecule. In some embodiments, the aptamer can include a stem and at least one loop. The at least one loop can include a capture region and the stem can include a stem region. The aptamer can selectively detect the target molecule and allow a direct measurement of the target molecule without dilution of the sample and without additional labeling reagents.

In certain embodiments, the method for identifying an aptamer, which is a specific sequence of nucleic acids, can be performed using a solution-phase selection of the aptamer from among many different sequences. In some embodiments, the detection method can include immobilizing the aptamer on the surface of a field-effect transistor. In non-limiting embodiments, the method can include adjusting the sensitivity of the aptamer-FET by modifying a length of the stem region.

In certain embodiments, the disclosed subject matter provides oligonucleotides that can selectively bind to target molecules. For example, a glucose oligonucleotide, which has at least five-times higher binding affinity for glucose, compared to non-glucose molecules, can include oligonucleotide sequences with consecutive bases identical at least 80% to CGTGTG or 80% to GTGTCC and a dissociation constant between about $1\times10^{-5}$ M to about $50\times10^{-3}$ M. A creatinine oligonucleotide, which has at least five-times higher binding affinity for creatinine, compared to non-creatinine molecules, can include oligonucleotide sequences with consecutive bases identical at least 80% to GGTGG or 75% to GGGG and a dissociation constant between about $1\times10^{-7}$ M to about $0.5\times10^{-3}$ M. A dopamine oligonucleotide, which has at least five-times higher binding affinity for dopamine, compared to non-dopamine molecules, can include oligonucleotide sequences with consecutive bases identical at least 80% to CCAGT or 75% to GGTGT and a dissociation constant between about $1\times10^{-9}$ M to about $1\times10^{-5}$ M. An oligonucleotide, which has at least five-times higher binding affinity for serotonin, sphingosine-1-phosphate, or phenylalanine, compared to non-target molecules, can include oligonucleotide sequences comprising GG and GGGG and GGG, or a variant thereof, respectively, and dissociation constants between about $1\times10^{-9}$ M to about $1\times10^{-4}$ M.

BRIEF DESCRIPTION OF THE FIGURES

FIG. 18C-F provide surface-enhanced Raman spectra of (13C) dopamine-, (13D) serotonin-, (13E) glucose-, or (13F) SIP-aptamer-thiol monolayers on Au-nanoshells prior to exposure to targets, after correct target exposure, and following non-target exposure.

FIG. 23A discloses SEQ ID NO: 22.

DETAILED DESCRIPTION

Figure 1A:
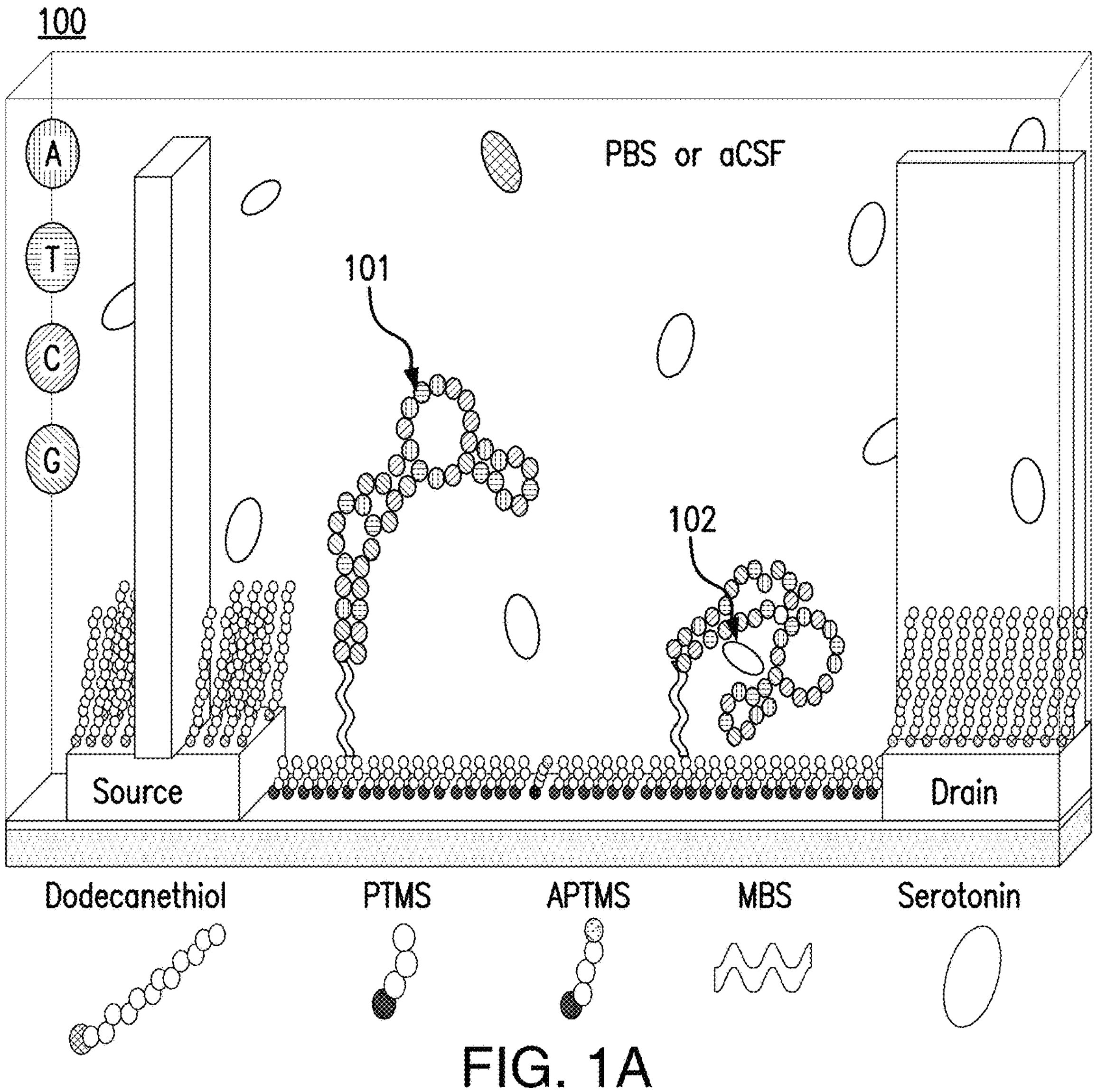
FIG. 1A provides an illustration of an exemplary field-effect transistor (FET) surface in accordance with the present disclosure.

The presently disclosed subject matter provides systems and methods for detecting analytes (targets) in a sample. The present disclosure provides devices based on aptamers attached to field-effect transistors (FETs). The aptamer can have a stem-loop structure and bind to analytes through interaction of the loop structure. Upon binding to the analyte, the aptamers can reorient (change conformation) and affect behavior of charge carriers in a semiconductor resulting in a change in the conductance of a FET.

As used herein, the term "analyte" or "target" refers to a substance whose chemical constituents are being identified and measured through the disclosed systems and arrays. An analyte can include, but is not limited to, all molecules with molecular weight less than 1000 D, ions, chemicals, peptides less than 5000 D, etc.

As used herein, the term "epitope" refers to the binding site on an analyte that is recognized by an aptamer.

As used herein, the term "about" or "approximately" means within an acceptable error range for a particular value, as determined by one of ordinary skill in the art, which will depend, in part, on how the value is measured or determined, (i.e., the limitations of the measurement system). For example, "about" can mean within 3 or more than 3 standard deviations, per the practice of the art.

As used herein, the term "subject" includes any human or nonhuman animal. The term "nonhuman animal" includes, but is not limited to, all vertebrates, (e.g., mammals and non-mammals, such as nonhuman primates, dogs, cats, sheep, horses, cows, chickens, rodents, amphibians, reptiles, etc). In certain embodiments, the subject is a pediatric patient. In certain embodiments, the subject is an adult patient.

Where a sequence provided herein refers to nucleotide "N", that position in the sequence can be filled by any natural or unnatural nucleotide, unless specified to the contrary.

As embodied herein, the disclosed subject matter provides a field-effect transistor (FET) for target/analyte detection. The disclosed FET can be used for direct electronic detection of targets, including but not limited to ions, small organic molecules, peptides or large molecules or biomolecules, determined under physiological, ionic-strength conditions. In certain embodiments, the FET can be a metal-oxide FET array 100 with deoxyribonucleotide aptamers 101 selected to bind their targets 102 adaptively (FIG. TA). A nanometer-thin metal-oxide FET (FIG. 1B) can be produced by methods that facilitate micro- and nanoscale patterning and can be readily scalable with respect to fabrication at high densities and for large numbers of devices. The metal-oxide FET can include a source electrode, a drain electrode, and a semiconductor channel between the source and drain electrodes. In non-limiting embodiments, the disclosed field-effect transistor can include an organic conducting polymer, a carbon material, or a combination thereof. For example, the carbon material can be 1D or 2D graphene or nanotubes.

In certain embodiments, the disclosed substrate can include a wafer and a semiconductor film. The wafer and semiconductor film can have any suitable size, shape, and dimensions for intended applications. For example, the wafer can be covered by an ultrathin semiconductor film such as an indium oxide film 103. Aqueous solutions of indium(III) nitrate hydrate ($In(NO_3)_3 \cdot xH_2O$, 99.999%) can be spin-coated onto heavily doped silicon wafers 104. In non-limiting embodiments, the substrate can include silicon dioxide ($SiO_2$) 105, titanium (Ti) 106, and gold (Au) 107. In some embodiments, the ultrathin semiconductor film can have a thickness ranging from about 1 nm to about 100 nm, from about 1 nm to about 50 mm, from about 1 nm to 10 nm, or 1 nm to 5 nm. The wafer can have a thickness ranging about 1 μm to 1000 μm or about 1 μm to 500 μm. In some embodiments, the wafer and semiconductor film can have a wide range of lengths and/or widths. The term "lateral dimension," as used herein, refers to the length and width. The term "thickness", as used herein, refers to the semiconductor depth. In accordance with certain embodiments, at least one lateral dimension of the wafer or semiconductor ribbon structure can be between about 2 nm and about 3000 μm or between about 1 nm and about 1500 m.

Figure 1B:
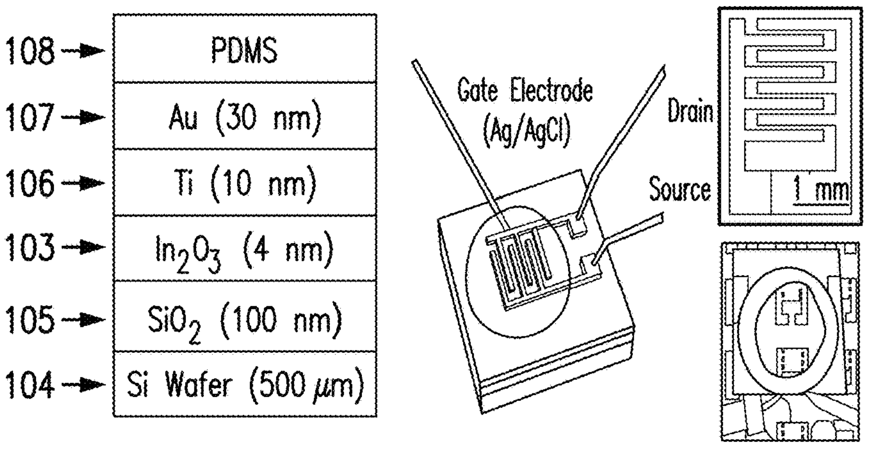
FIG. 1B provides a schematic illustration of an exemplary layer-by layer composition of a FET in accordance with the present disclosure.

In certain embodiments, an electrode can be located on the substrate. For example, interdigitated source and drain electrodes can be patterned by photolithography and deposited by electron-beam evaporation on top of the semiconductor film to obtain improved transconductances and uniform current distributions. The pattern of the electrodes can determine the semiconductor channel dimensions. For example, as shown in FIGS. 1A and 1B, a semiconductor channel can be created between the drain and source electrodes.

In certain embodiments, the disclosed FET can detect a target molecule or analyte through signal transduction and amplification. The signal transduction and amplification can be based on electrostatic gating of semiconductor channels by target-receptor complexes to produce changes in semiconductor transconductance. The receptors can be placed on the surface of the semiconductor channel. The receptors can be immobilized on the semiconductor channel exposed regions using a top-gate device configuration. For example, as shown in FIGS. 1A and 1B, (3-aminopropyl)trimethoxysilane (APTMS) and trimethoxy(propyl)silane (PTMS) (1:9 v/v ratio) can be thermally evaporated using vapor-phase deposition onto $In_2O_3$ surfaces at 40° C. for 1 h followed by incubation in 1 mM ethanolic solutions of 1-dodecanethiol for 1 h to passivate Au electrodes. In addition to electrode passivation, device-to-device cross-talk with other FETs on each substrate can be prevented by isolating each device individually during measurements via PDMS cups or other methods of isolation. Furthermore, substrates can have substantial inter-FET distances (~2 mm). There is no or minimal leakage current from the gate electrode (Ag/AgCl). In certain embodiments, surface ratios of methyl-terminated (PTMS) and amine-terminated (APTMS) silanes can be altered to change the numbers of aptamers attached to the semiconductor channel. Other linking chemistries for the aptamers can be applied to the disclosed system, as known to those skilled in the art.

As embodied herein, the disclosed receptors can include an aptamer that can selectively recognize a target molecule/analyte. The aptamer can include a capture region and a stem region. The aptamer can bind to the target molecule or analyte through the capture region. For example, the capture region can include a core sequence that acts as a binding pocket for the target analyte. In certain embodiments, the aptamer can include a particular core sequence, a consensus core sequence, and/or an operative sequence. In some embodiments, the aptamer can optionally include an additional sequence, other than core sequence or operative sequence, which does not substantially impact its functionality. The aptamer comprising a core sequence that binds to a target analyte of interest can be utilized in diverse assays, including but not limited to those exemplified herein.

In certain embodiments, the disclosed subject matter provides a stem-loop aptamer. The stem-loop aptamer can include at least one stem and at least one loop. The at least one loop can include a capture region that includes a core sequence that acts as a binding pocket for the target analyte. In non-limiting embodiments, more than one loop can form the target binding pocket. In some embodiments, the binding of the target analyte can occur through interactions with the loop. For example, and not by way of limitation, the stem-loop aptamer can have loose loop structures in the absence of target analytes. Upon binding of the target analytes to the capture region, the loop can wrap around the target analytes ligands. In some embodiments, the loop can further include a secondary structure. The secondary structure can include a base-paired structure (e.g., canonical Watson-Crick base pairs, but also wobble and mismatched base pairs), which can be predicted to be formed using folding programs. For example, in FIG. 2A, the glucose aptamer as shown has an additional stem-loop formed by the sequence ACAATGTCTCGTTGT (SEQ ID NO: 1), while the serotonin aptamer has an additional stem-loop formed by the sequence GAAGCTGATTC (SEQ ID NO: 2) In certain embodiments, the aptamer can reorient its stem-region and/or its loop(s) region(s) upon the binding of the target analyte. For example, and not by way of limitation, a significant portion of the negatively charged backbone of the aptamer can move closer to surface of the FET, increasing electrostatic repulsion of charge carriers in an n-type FET and decreasing transconductance, measured as target-related current responses. In some embodiments, and not by way of limitation, a significant portion of the negatively charged backbone of the aptamer can move further away from the semiconductor channel of the FET, decreasing electrostatic repulsion of charge carriers in an n-type FET, and thereby increasing transconductance, measured as concentration-dependent target-related current responses. In some embodiments, the aptamer can include a partly charged oligonucleotide, neutral oligonucleotide analogues, and/or other modifications. For example, the aptamer can include a partly charged backbone. The aptamer can include at least about 1%, 5%, 10%, 15%, 20%, 25%, 30%, 35%, 40%, 45%, or 50% of a negatively charged backbone. In some embodiments, aptamers can increase or decrease their volume upon target binding, displacing or associating solution ions, which can also change FET transconductance. In neutral or nearly neutral aptamers, the displacement of the ionic solution can be sufficient to gate the FET channel conductance and thus effect signal transduction and target measurement.

In certain embodiments, the aptamers can have any size consistent with their intended function. In certain non-limiting embodiments, an aptamer or associated oligonucleotide is between about 20-250 nucleotides in length. For example, but not by way of limitation, the length can be between about 20-200 nucleotides, or between about 20-150 nucleotides, or between about 30 and 200 nucleotides, or between about 40-200 nucleotides, or between about 50-200 nucleotides, or between about 60-200 nucleotides, or between about 70-200 nucleotides, or between about 80-200 nucleotides, or between about 100-200 nucleotides, or between about 150-200 nucleotides, or between about 30-150 nucleotides, or between about 30-100 nucleotides, or between about 30-80 nucleotides, or between about 30-50 nucleotides, or between about 40-100 nucleotides; or at least about 20 nucleotides, or at least about 30 nucleotides, or up to about 100 nucleotides, or up to about 200 nucleotides or between 20-250 nucleotides, or between 25 and 100 nucleotides. In certain non-limiting embodiments, aptamers can be spiegelmers or contain unnatural enantiomers of nucleic acids. In certain non-limiting embodiments, aptamers can contain unnatural nucleotides.

In certain embodiments, the oligonucleotide can further include molecules that amplify the charge of the oligonucleotide. The molecules can be selected from a group consisting of non-binding oligonucleotides, particles, dendrimers, or fragments that can attract other species as amplifiers and combinations thereof.

Figure 2A:
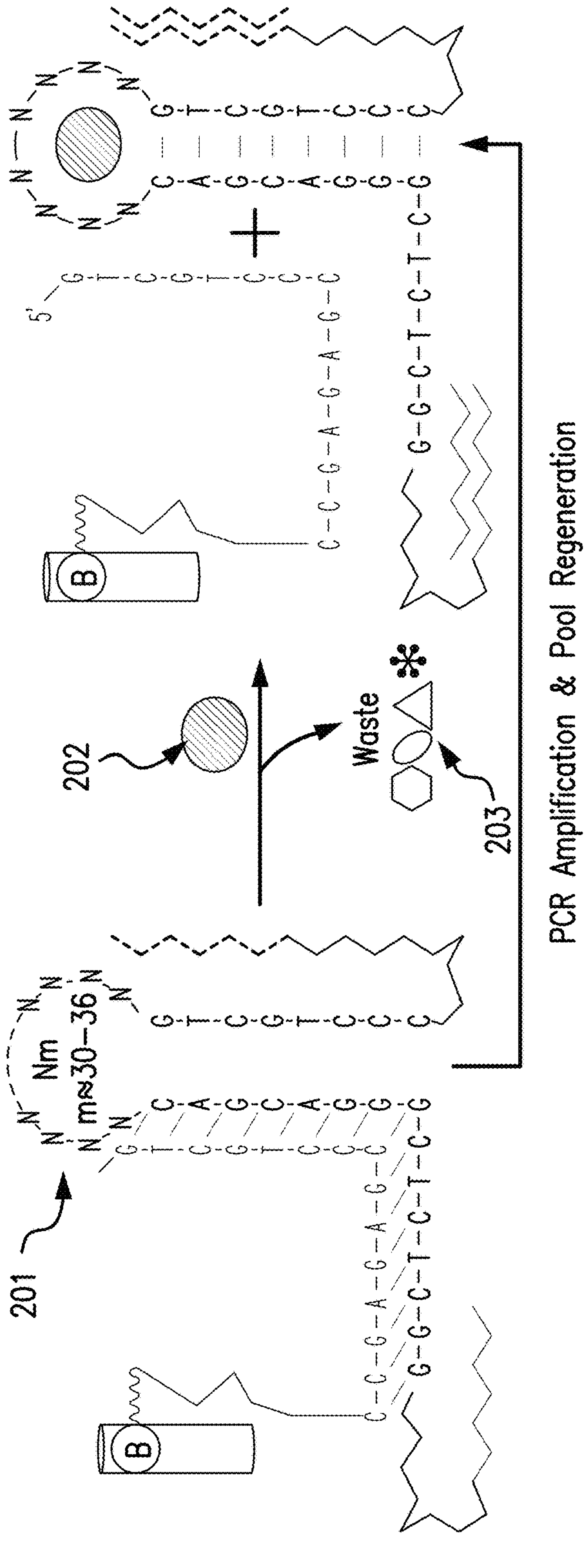
FIG. 2A provides an illustration of an exemplary aptamer selection. Figure discloses SEQ ID NOS 91, 92, 91, and 93, respectively, in order of appearance.

In certain embodiments, the disclosed subject matter provides methods of generating aptamers for adaptive target recognition selection. In certain embodiments, an aptamer can be isolated by solution-phase or solid-phase selection. As shown in FIG. 2A, solution-phase selection that circumvents tethering small-molecule targets and is based on stem-loop closing can be used to isolate receptors with appropriate counter-selection against interferents. FIG. 2A provides an illustration of an exemplary aptamer selection. Oligonucleotide libraries (Nm, with random regions, for example, m=30-36 nucleotides, flanked by constant regions and primer-specific regions for PCR amplification) can be attached to agarose-streptavidin columns via biotinylated complementary oligonucleotides. Exposure to targets 202 can cause elution of specific oligonucleotide sequences in which stems are stabilized. These sequences can be preferentially amplified. Exposure to counter-targets 203 can eliminate cross-reactive sequences. This approach can yield aptamers characterized by adaptive-loop binding. Aptamers can be identified that selectively bind to diverse target analytes, including, but not limited to amino acids, mono- and oligo-saccharides, steroids, catecholamines, monoamines, amino acids, serotonin, dopamine, glucose, sphinghosine-1 phosphate, melatonin, phenylalanine, lipids, hormones, and/or peptides.

In certain non-limiting embodiments, the method can be used to produce aptamers that can be converted to spiegelmers for vasopressin, aminoglycosides and other antibiotics, immunosupressants, anti-tumor agents, pesticides, hormones, etc. In some embodiments, original receptors for dopamine, serotonin, glucose, and sphingosine-1-phosphate (S1P) can be isolated through a solution-phase selection method (FIG. 2B-E).

Figures 2B, 2C, 2D, 2E:
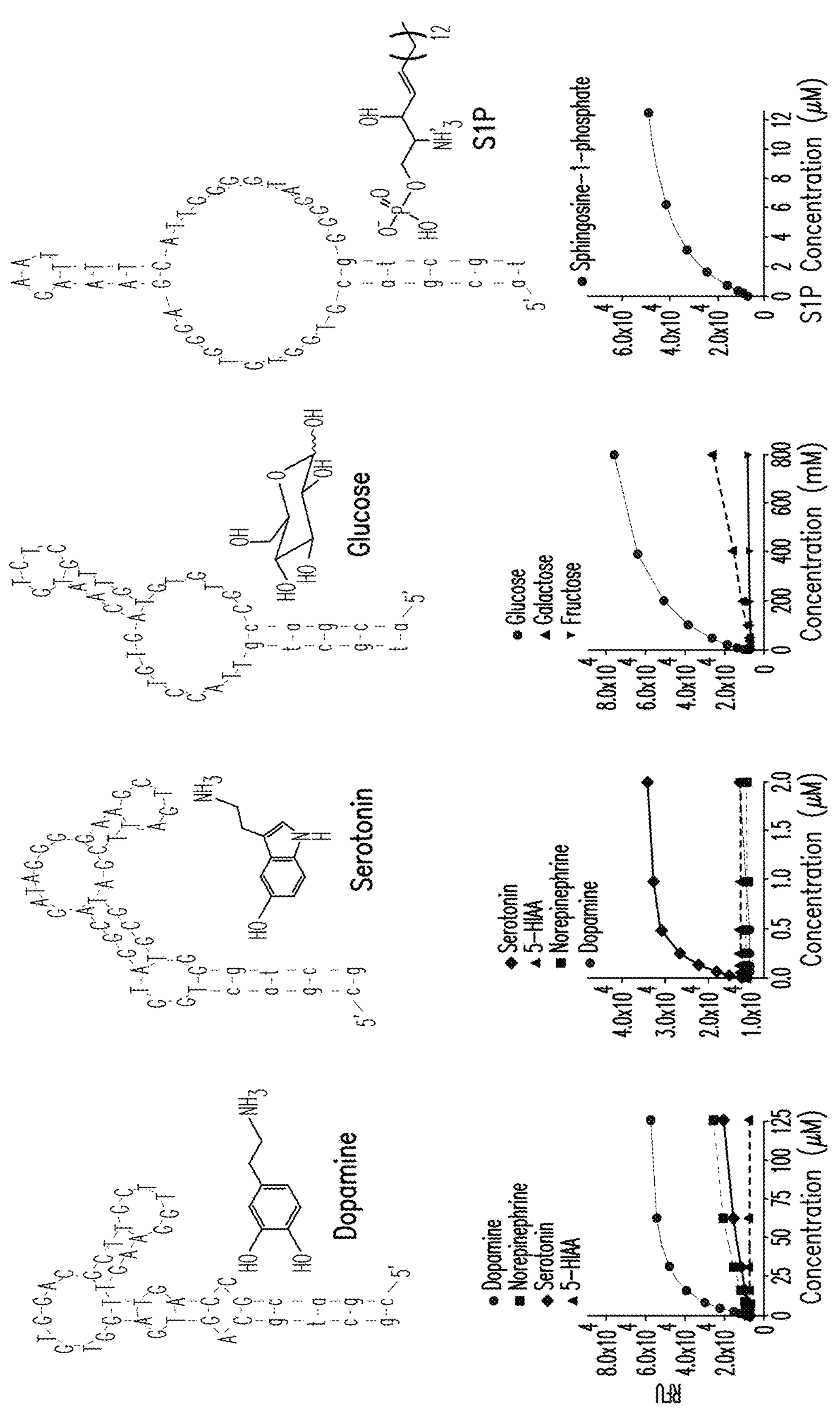
FIG. 2B provides an exemplary structure (SEQ ID NO: 28) and fluorescence responses of the selected dopamine aptamer to target and nontarget neurotransmitters.
FIG. 2C provides an exemplary structure (SEQ ID NO: 45) and fluorescence responses of the selected serotonin aptamer to target and nontarget neurotransmitters.
FIG. 2D provides an exemplary structure (SEQ ID NO: 5) and fluorescence responses of the selected glucose aptamer to various target and nontarget sugars.
FIG. 2E provides an exemplary structure (SEQ ID NO: 25) and fluorescence responses of the selected sphingosine-1-phospate (S1P) aptamer to target.

FIG. 2B provides an exemplary structure and fluorescence responses of the selected dopamine aptamer to target and nontarget neurotransmitters. FIG. 2C provides an exemplary structure and fluorescence responses of the selected serotonin aptamer to target and nontarget neurotransmitters. FIG. 2D provides an exemplary structure and fluorescence responses of the selected glucose aptamer to various target and nontarget sugars. FIG. 2E provides an exemplary structure and fluorescence responses of the selected sphingosine-1-phospate (SIP) aptamer to target. Fluorescence-concentration curves are the result of triplicate measurements with standard deviations too small to be visualized in the graphs shown.

In certain non-limiting embodiments, the method of generating aptamers can include attaching a biotinylated complementary strand ($C_B$) to an agarose-streptavidin column. The complementary strand can be designed to hybridize with one of the fixed primer (stem) regions to capture library sequences on a column. The library can have different oligonucleotide sequences, which can have viable regions (e.g., but not limited to, $N_8$-$N_{100}$). Two primer regions on the library 5'- and 3'-ends can also be partially complementary. Members of the library that interact with a target in a way that favors stem formation between these nucleotide ends can release the specific sequences from the agarose column by displacing complementary strand $C_B$. Only these sequences can be amplified by PCR to create an enriched pool of potential aptamers. In solution-phase selection, target analytes can be used without any attachment to a matrix, thus, no target functional groups need to be altered or rendered unavailable for recognition. This can increase interactions with aptamers leading to increased affinities. Target concentrations can be used up to the limit of target solubility allowing isolation of weak-affinity aptamers (e.g., against metabolites and glucose).

In certain non-limiting embodiments, fluorescence assays can be used to characterize aptamer-target dissociation constants ($K_d$). The solution-phase selected dopamine aptamer shows improved-affinity for dopamine compared to a different dopamine aptamer previously identified by solid-phase selection (FIG. 2B). A new serotonin aptamer can be generated by solution-phase selection (FIG. 2C). Counter-selection can eliminate interactions with other monoamine neurotransmitters, precursors, and metabolites, (i.e., nontargets). Aptamer selectivity for recognizing targets is critical for sensing in the presence of high concentrations of similarly structured counter-targets in vivo. The disclosed aptamers do not recognize non-target molecules, in contrast to cross-reactivity plaguing previously reported aptamers. (FIGS. 2B-2E).

In certain non-limiting embodiments, aptamer candidates can be identified using the following procedures: (1) Isolating aptamers by solution-phase or solid-phase selection; use of enantiomeric aptamers (spiegelmers), if desired to minimize Watson-Crick base pairing (e.g., fusing aptamers to minimize background interactions without analyte); (2) Testing of the aptamer in its structure-switching form and modifying its structure switching form; (3) If necessary, preparing a shortened form of the aptamer originally isolated; and (4) If necessary, modifying the optionally shortened aptamer by introducing an operative sequence; and/or modifying the optionally shortened aptamer by substituting one or more nucleotides in its binding pocket to improve binding properties in the intended assay.

In certain embodiments, the selected aptamers can be functionalized to semiconductor surfaces. For example, substrates can be rinsed in ethanol and immersed in 1 mM solutions of 3-maleimidobenzoic acid N-hydroxysuccinimide ester (MBS) dissolved in a mixture of dimethyl sulfoxide and PBS. The MBS can crosslink amine-terminated silanes to thiolated DNA aptamers. Aptamers can be prepared for attachment to substrates by heating in nuclease-free water followed by rapid cooling in an ice bath. Substrates can be rinsed with deionized water and immersed in 1 μM solutions of thiolated DNA aptamers, rinsed again with deionized water, and blown dry with $N_2$ gas. In some embodiments, the disclosed field-effect transistor can include an organic conducting polymer, a carbon material, or a combination thereof. For example, the carbon material can be 1D or 2D graphene or nanotubes.

In certain aspects, the disclosed FETs can detect a target analyte in a sample. The sample can include a target in a high ionic-strength solution, including but not limited to whole blood, blood serum or plasma, urine, kidney or brain dialysate, or buffer solutions that mimic the high-ionic content of physiological samples. In solutions containing ions, the ionic double-layer that forms near the semiconductor surface can shield semiconductor charge carriers from responding to changes in electric fields near semiconductor surfaces needed to detect receptor-target interactions. The extent of shielding, i.e., the effective sensing distance, can be characterized by the Debye length, which in high ionic-strength solutions is <1 nm. Accordingly, the Debye length in high ionic-strength solutions can require that a significant portion of charge redistribution upon receptor-target binding needs to be within or near the Debye length for semiconductor transconductance to be altered.

In certain aspects, the disclosed FETs can detect a target analyte in tissue or in vivo. The sample can include a target in an organ or part of an organ of a human or non-human animal, including but not limited to the brain or a subregion of the brain, on the skin, in the oral cavity, in the vaginal cavity, or in the gut. Target analytes can include signaling molecules that are part of microbial communication in the local microbiome. In non-limiting embodiments, the target molecule can also include atoms and atomic ions such as lithium ions. The sample can include donor organs that can be used for transplantation ensuring their safety and compatibility. In non-limiting embodiments, the disclosed FETs can detect a target analyte in soil, the atmosphere, a body of water, food, food components, or food waste, or in a waste stream or waste container.

In certain embodiments, the present disclosure provides an ultrathin metal-oxide FET coupled to conformationally flexible, compact, highly negatively charged aptamers to detect low-charge or electroneutral targets selectively over large, physiologically relevant concentration ranges, and where direct and massively parallel measurements can preclude sample dilution or another sample manipulation. For example, and not by way of limitation, as an aptamer loop structure wraps around a target analyte, certain changes in the average positions of the negatively charged oligonucleotide backbone and associated companion ions can result in changes in the electric field close to semiconductor surfaces to modify FET transconductance.

Figure 3A:
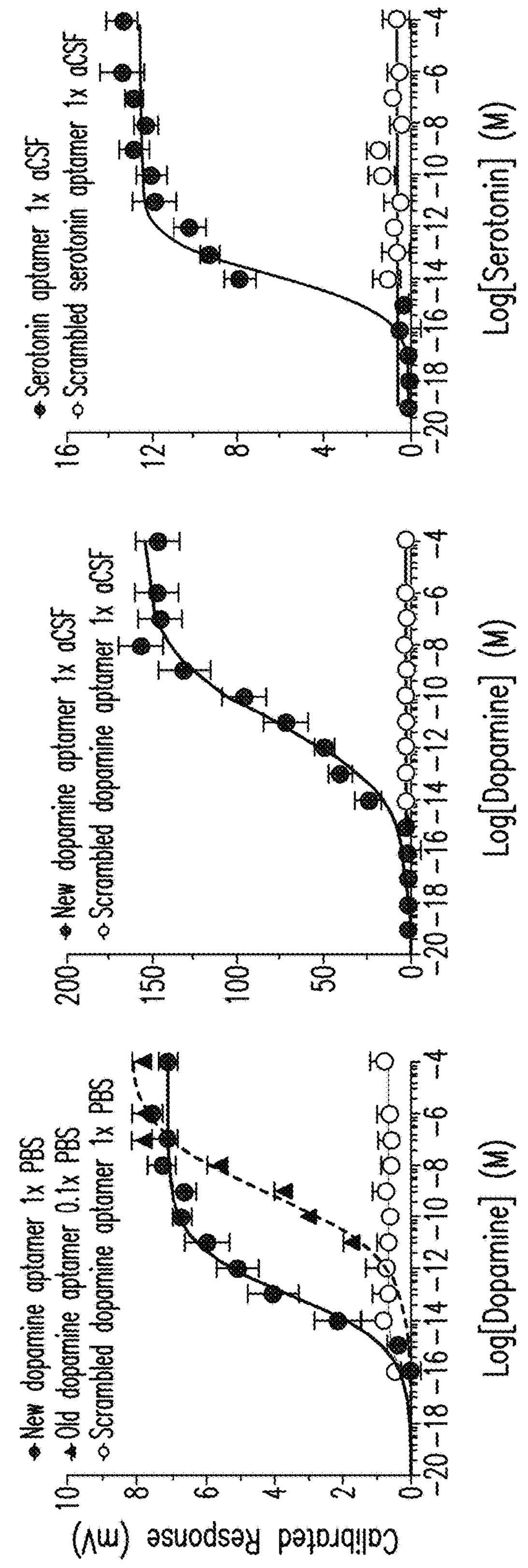
FIG. 3A provides graphs of responses of field-effect transistor (FET) sensors functionalized with a dopamine aptamer, a scrambled dopamine aptamer, a serotonin aptamer, or a scrambled serotonin aptamer in high ionic strength physiological solutions, (i.e., phosphate-buffered saline (PBS) or artificial cerebrospinal fluid (aCSF)).
Figure 3B:
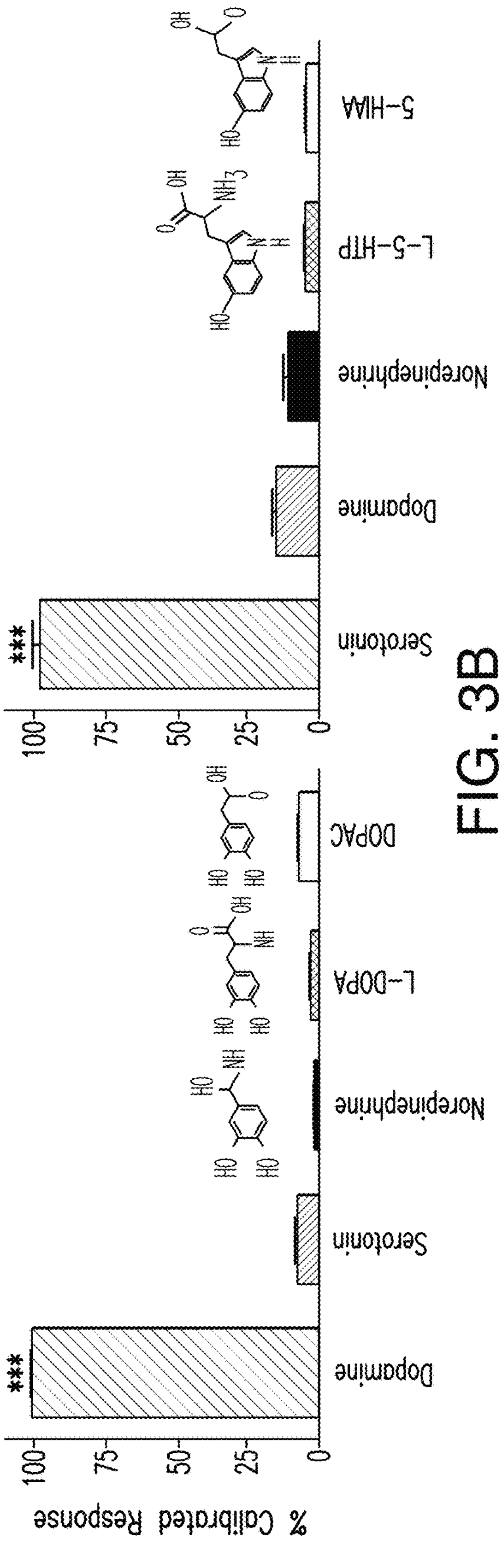
FIG. 3B provides plots of dopamine or serotonin-aptamer-FET responses to targets vs. nontargets (i.e., norepinephrine, serotonin, L-3,4-dihydroxyphenylalanine (L-DOPA), 3,4-dihydroxyphenylacetic acid (DOPAC), and dopamine).

In certain embodiments, the disclosed FET can provide nonlinear detection of the target over large and low concentration ranges compared to equilibrium-based sensors. For example, despite sub-nanometer Debye screening lengths, the disclosed aptamer-FET can respond to wide ranges of target concentrations ($10^{-14}$-$10^{9}$ M) in undiluted, i.e., high ionic strength, physiological samples such as those that include target in phosphate-buffered saline (PBS) or artificial cerebrospinal fluid (aCSF) (FIG. 3A). Both of these solutions can contain high concentrations of ions, which can shield the semiconductor surface. Even at physiological ion concentrations and hence, significantly reduced Debye lengths, the disclosed FET can have responses that are more than three orders of magnitude greater than those of a previously reported dopamine aptamer in PBS diluted tenfold (FIG. 2A), due to by-design positioning of aptamer recognition regions capable of adaptive conformational changes. Dopamine-aptamer-FETs can selectively respond to dopamine compared to non-dopamine molecules with similar chemical structures, such as serotonin, norepinephrine, tyramine, and dopamine precursors and metabolites (FIG. 3B). Serotonin-aptamer-FETs can selectively detect serotonin compared to non-serotonin but similar molecules, such as dopamine, norepinephrine, histamine, and other biogenic amines and indole precursors or metabolites (FIG. 3B).

Figures 4A, 4B, 4C, 4D, 4E, 4F:
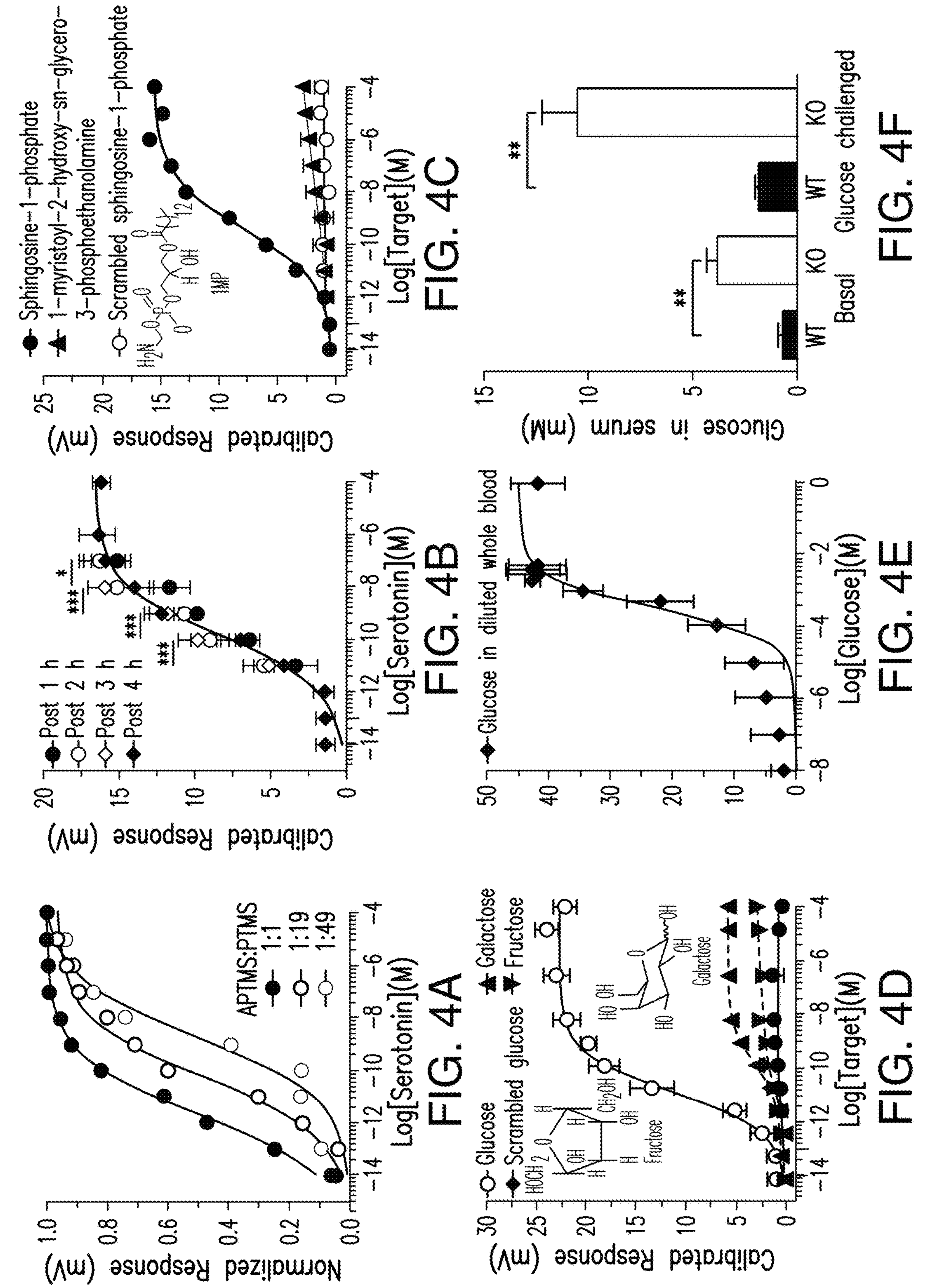
FIG. 4A provides plots showing that serotonin aptamer-FET sensitivities can be shifted by altering ratios of amine: methyl-terminated silane molecules.
FIG. 4B provides plots of responses of serotonin-aptamer-functionalized FETs after exposure to brain tissue lacking serotonin for 1, 2, 3, or 4 hours followed by the addition of increasing concentrations of serotonin.
FIG. 4C provides plots of concentration-dependent responses of S1P aptamer-FETs to S1P target molecules vs. nontarget lipid molecules.
FIG. 4D provides plots of responses in Ringer's buffer of glucose-aptamer-FETs to glucose and the nontarget molecules galactose or fructose, and a scrambled sequence.
FIG. 4E provides plots of glucose aptamer-FET responses in mouse whole blood diluted in Ringer's to measure glucose levels.
FIG. 4F provides graphs illustrating glucose levels in serum from normal mice and mice that develop hyperglycemia under basal and glucose challenged conditions.

In certain embodiments, concentration sensitivity ranges of FETs can be tuned by altering the numbers of aptamers on FET surfaces. For example, as shown in FIG. 4A, the sensitivity of a serotonin-aptamer-FET can be modified by changing the ratios of amine:methyl-terminated silane molecules, which in turn, can change the numbers of serotonin aptamers covalently attached to a semiconductor surface. Silane molecules can self-assemble on a metal oxide semiconductor surface. The amine-terminated silane molecules react with aptamer molecules to covalently bind the aptamers to a semiconductor surface. The methyl-terminated silane molecules cannot form a bond with thiolated aptamers. Methyl-terminated silane molecules dilute the numbers of aptamers on a semiconductor surface and can prevent target and nontarget molecules in a sample from associating with the semiconductor surface nonspecifically. In addition to the various surface chemistries disclosed, it will be apparent to those skilled in the art that various modifications and variations can be made to attach and to dilute aptamers on a surface without departing from the scope of the disclosed surface chemistries. Thus, it is intended that the disclosed surface chemistries include modifications and variations that are within the scope of the disclosed chemistries and their equivalents. In some embodiments, the disclosed FETs can be exposed to a sample without altering the sensitivity of the FET. For example, continuous exposure of a serotonin-aptamer FET to brain tissue for 1-4 h can result in reproducible concentration-dependent conductance responses indicative of sensor stability in complex biological environments (FIG. 4B).

Figure 6A:
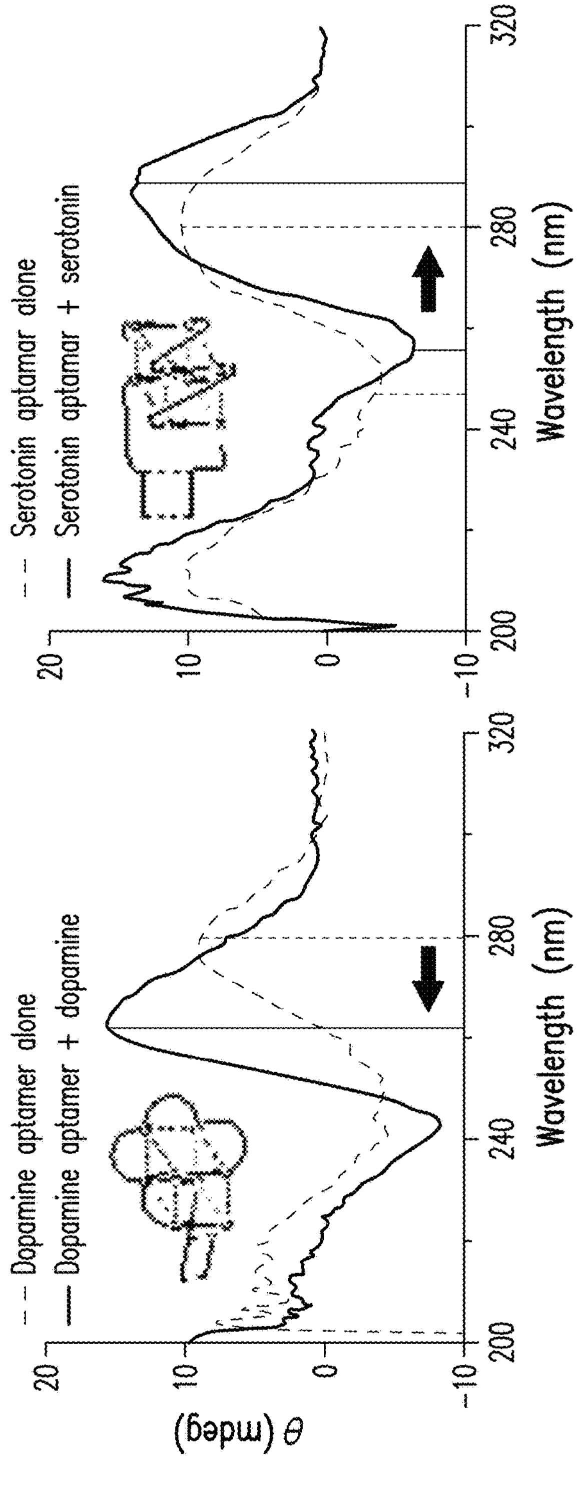
FIG. 6A provides circular dichroism plots illustrating changes in secondary structures of dopamine and serotonin aptamers upon target capture.
Figure 6B:
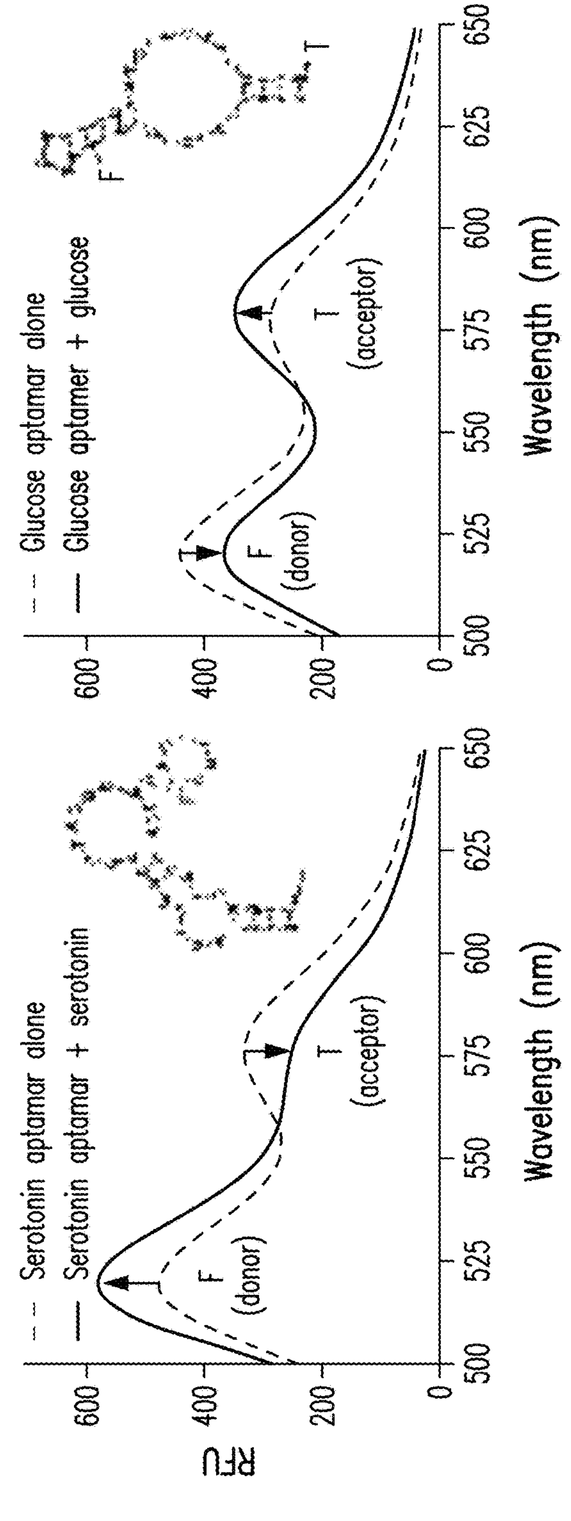
FIG. 6B provide plots of Forster resonance energy transfer fluorescence responses illustrating that for the serotonin aptamer, donor fluorescence increased, while acceptor emission decreased upon serotonin incubation in accordance with the proposed mechanism in FIG. 5C. By contrast, for the glucose aptamer, donor fluorescence decreased, while acceptor fluorescence increased upon target recognition in accordance with the proposed mechanism in FIG. 5B. Figure discloses SEQ ID NOS 94 and 95, respectively, in order of appearance.
Figure 6C:
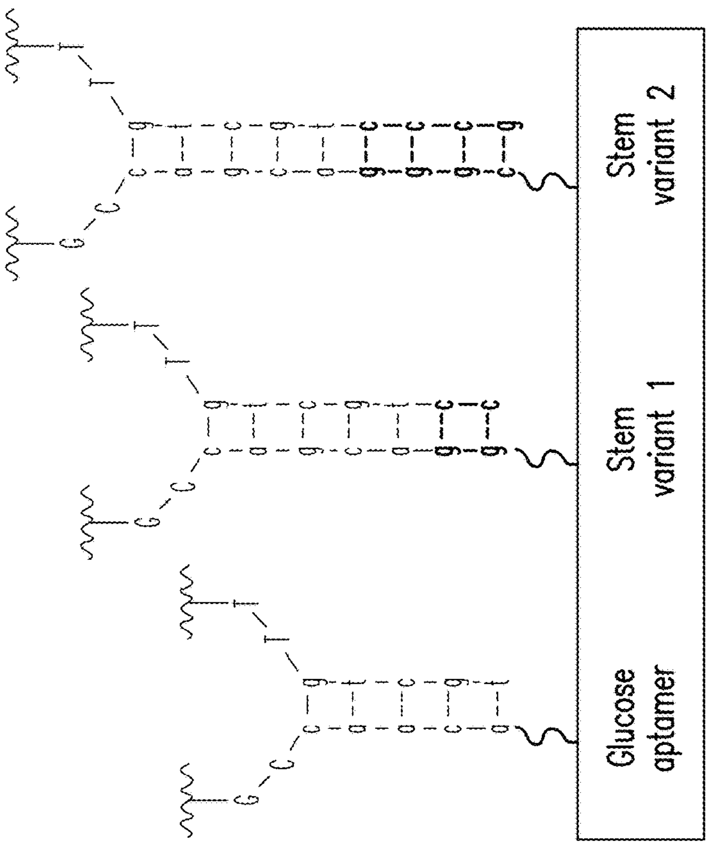
FIG. 6C provides a schematic illustration of an exemplary lengthening of the glucose stem-loop aptamer stem region. Figure discloses SEQ ID NOS 96 and 97, respectively, in order of appearance.
Figure 6D:
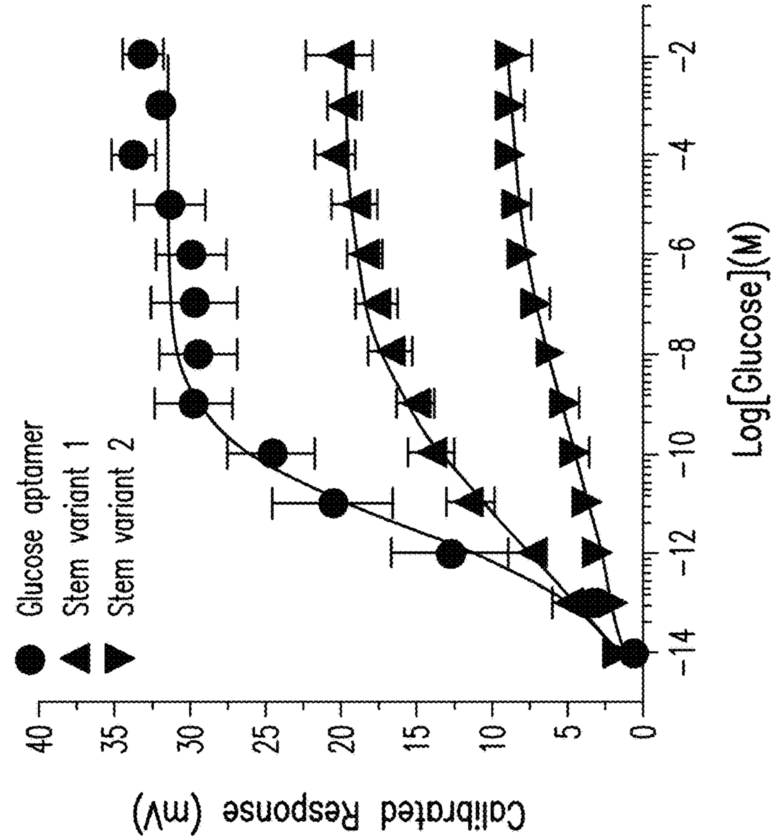
FIG. 6D provides plots illustrating responses corresponding to FIG. 6C.

In some embodiments, the sensitivity of the disclosed aptamers can be tuned by adjusting a length of the stem region. For example, as shown in FIGS. 6C and 6D, distances from semiconductor surface can be increased by adding additional base pairs to the attachment stem. For the glucose aptamer, conductance responses decreased with additional base pairs (FIG. 6D), indicating that recognition occurred further away from FETs as the attachment stems became longer.

In certain embodiments, the disclosed FET can selectively respond to lipid S1P or glucose. Similar to dopamine- and serotonin-aptamer-FETs, these SIP- and glucose-aptamer-FETs can differentiate their target molecules from non-target molecules (FIGS. 4C and 4D).

In certain embodiments, the disclosed FET can sense a target molecule in full ionic strength blood or blood serum. The disclosed FET can also differentiate physiologically relevant differences in neutral target concentrations. For example, the disclosed FET can detect glucose in whole blood diluted with Ringer's buffer (FIG. 4E). By way of example, but not limited to a particular biological model or medical condition, the disclosed FET can measure glucose levels in diluted serum from mice lacking serotonin transporter expression characterized by hyperglycemia. Elevations in serum glucose in basal and glucose-challenged states can be observed using the glucose-aptamer-FETs (FIG. 4F). Glucose aptamer-FETs can distinguish hyperglycemia in serotonin transporter deficient (knockout (KO)) mice from wildtype (WT) mice by measuring glucose levels in serum in basal and glucose challenged conditions. All calibrated responses were at gate voltage VG=100 mV. Error bars are standard errors of the means. *$P<0.001$ vs. counter-targets; $P<0.01$ KO vs. WT.

Figure 5A:
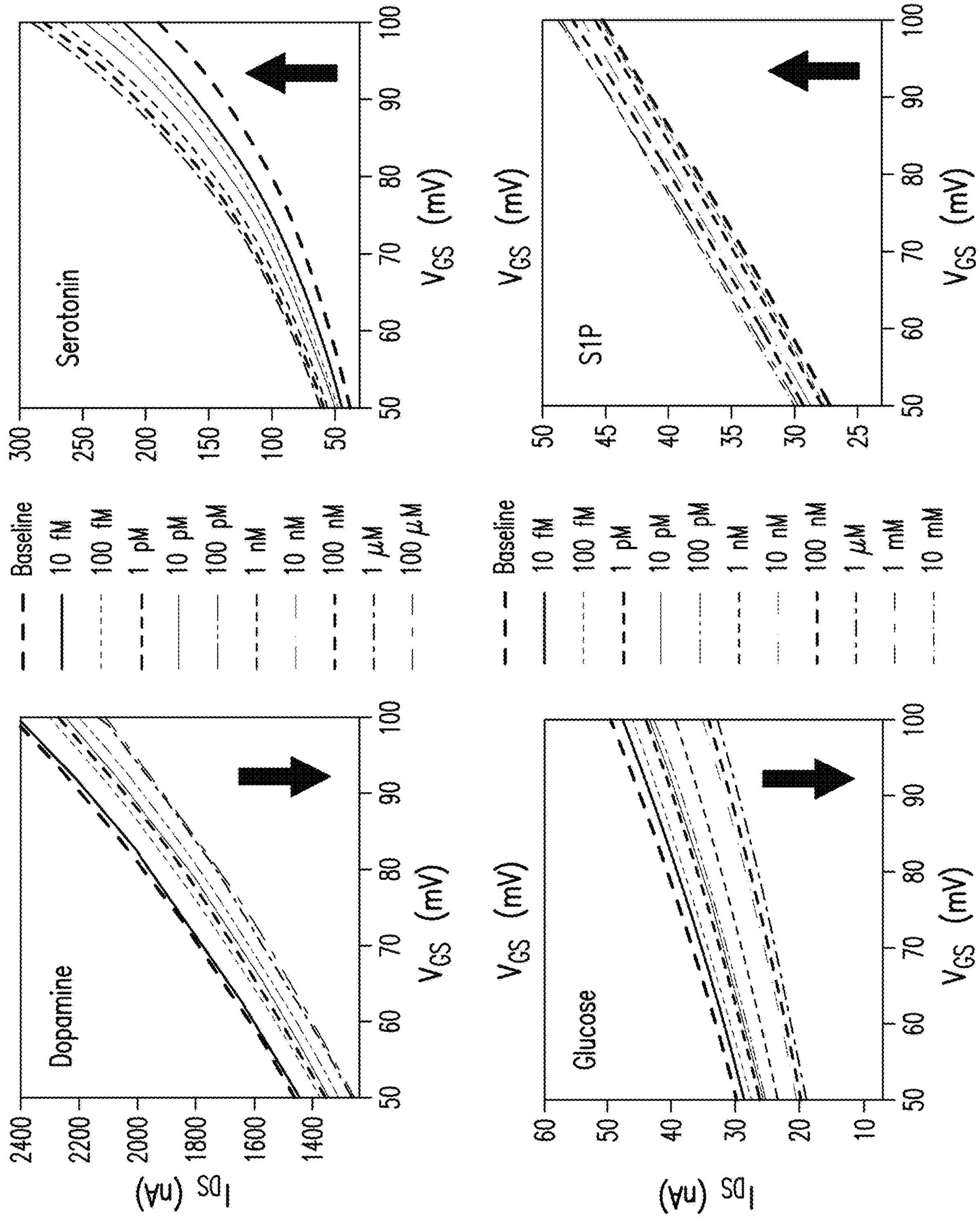
FIG. 5A provides plots of concentration-dependent changes in source-drain currents as a function of gate voltage measured from dopamine, serotonin, glucose, and S1P-aptamer-FETs.
Figure 5B:
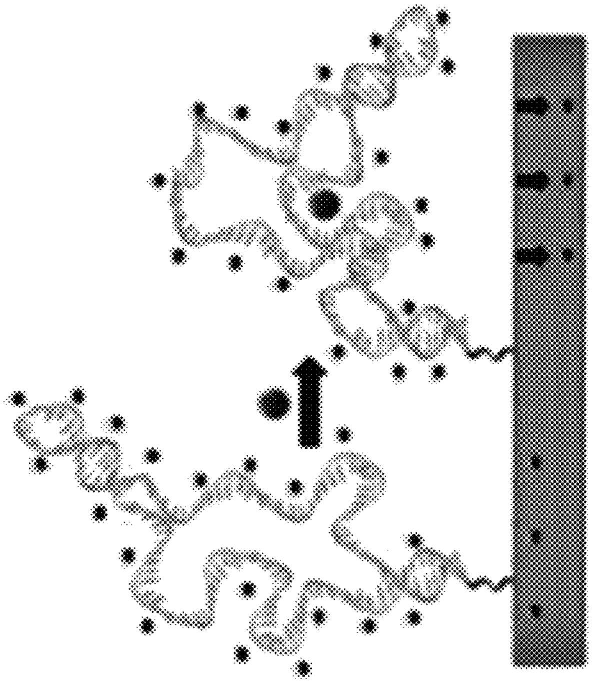
FIG. 5B provides a schematic illustration of an exemplary mechanism of stem-loop aptamer target-induced reorientations.
Figure 5C:
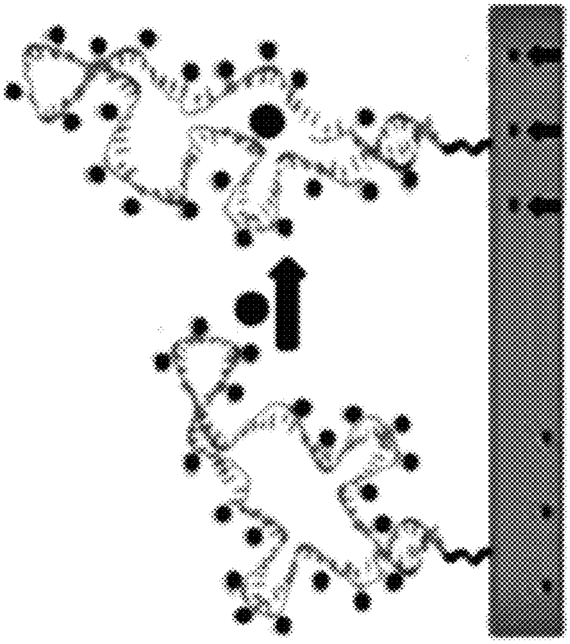
FIG. 5C provides a schematic illustration of another exemplary reorientation mechanism.

In certain embodiments, the disclosed FETs can include an aptamer that can change its structure upon the binding of the target analyte. The disclosed dopamine and glucose aptamers can move a significant portion of their negatively charged oligonucleotide backbones closer to surface of the FET, increasing electrostatic repulsion of semiconductor charge carriers and decreasing transconductance in n-type FETs. In some embodiments, the aptamer can include a partly charged oligonucleotide and/or other modifications. For example, the aptamer can include a partly charged backbone. The aptamer can include at least about 1%, 5%, 10%, 15%, 20%, 25%, 30%, 35%, 40%, 45%, or 50% of a negatively charged backbone. By way of example, serotonin and S1P aptamers can move away from the surface of FET upon target capture increasing transconductance. For example, as shown in FIG. 5A, exposure of dopamine-aptamer-FETs to dopamine (artificial cerebrospinal fluid (1×aCSF)) can cause concentration-dependent reductions in source-drain currents. For serotonin-aptamer-FETs, increasing concentrations of serotonin (1×aCSF) can produce increases in source-drain currents. Exposure of glucose aptamer-FETs to glucose (1×Ringer's) can induce reductions in source-drain currents. The S1P aptamer-FET transfer curves (1×HEPES) increase in response to target concentrations. FIG. 5B shows that certain aptamers can reorient closer to FETs to deplete channels electrostatically (e.g., dopamine, glucose). The aptamer can reorient upon target binding so that a portion of the aptamer rearrangement brings more of the negatively charged oligonucleotide backbone closer to the semiconductor surface. FIG. 5C shows that other aptamer stem-loops can reorient away from semiconductor channels upon target capture increasing transconductance (e.g., serotonin, SIP). The aptamer recognition of target can cause a conformational reorientation such that the negatively charged oligonucleotide backbone moves further away from the semiconductor surface. Schematics are idealized and do not reflect individual aptamer secondary structural motifs.

In certain embodiments, the disclosed aptamers can form new secondary structures upon target recognition and binding. The disclosed dopamine and serotonin aptamers can form new target-induced secondary structural motifs. For example, the dopamine aptamer complex can form a parallel G-quadruplex and the serotonin-aptamer complexes can form an antiparallel G-quadruplex. As shown in FIG. 6A, the dopamine aptamer can have significant shifts in the circular dichroism spectra indicating formation of a compact parallel G-quadruplex. By contrast, the serotonin aptamer can have a shift in peak positions of the circular dichroism spectra indicating formation of an antiparallel G-quadruplex. Forster resonance energy transfer (FRET) between donor-, fluorescein (F), excited at 470 nm, and acceptor-, 5-carboxytetramethylrhodamine (T), modified aptamers can be monitored before and after target incubation. As shown in FIG. 6B, donor fluorescence increased while acceptor emission decreased upon serotonin incubation, suggesting that fluorophores move further away from each other upon target exposure for serotonin aptamers, (i.e., aptamer moves further away from FET semiconductor surface upon target capture). Conversely, for glucose aptamers, the emission spectra for the acceptor increased, while donor fluorescence decreased upon glucose exposure indicative of acceptor moving closer to donor enabling increased energy transfer (i.e., aptamer moves closer to FET semiconductor surface upon target capture). As shown in FIG. 6C, for glucose-aptamer-FETs with rigid double-stranded attachment stems (left), increasing the distances from semiconductor surfaces by increasing the stem lengths (stem variants; right) can cause length-associated decreases in FET calibrated responses (right). The secondary structure can include a base-paired stem structure that is configured to hybridize upon target capture.

In certain embodiments, the isolation of aptamers can be performed using the SELEX and counter-SELEX processes. For example, the first aptamers can be selected though the first round 701 based on conditions of the target (e.g., epitope of the target). If the target has no cross-reactivity, the same conditions as the first round 701 can be maintained at round 2 702. If more prominent target elution bands appear after round 2 702, then the target concentration can be reduced. If the target elution bands are not changed or reduced, the same condition as round 2 can be maintained for additional rounds 703. If there are no prominent target elution bands after the last wash, then an increased target concentration can be tried for the next trial 704. If there are prominent target elution bands after the last wash, the target concentration can be further reduced 705. If the applied concentration from 705 is satisfactory, the product from 705 can be selected from the final round 706. If the target has cross-reactivity, counter SELEX can be introduced 706. If there are no prominent target elution bands after the wash with counter SELEX, the same conditions as round 1 can be maintained for the next round 707. If there are still no prominent target elution bands, the same conditions as round 1 can be maintained for the next round 709 and then an increased target concentration can be tested for the next trial 711. If prominent target elution bands appear from previous rounds 706, 707, and 709, the counter SELEX can be reintroduced and decreased concentration of the counter target can be applied 708. If more prominent target elution bands appear, the target concentration can be reduced or maintained 710. Alternatively, for 710, the target concentration can be maintained, and the counter target concentration can be increased. If there are prominent target elution bands after 710, a similar process can be repeated for 712. If the applied concentration from 712 is satisfactory, the product can be selected at the final round 713. In certain non-limiting embodiments, the aptamers can be isolated by either solid- (traditional) or newer solution-phase selections. Further, in certain non-limiting embodiments, the solution-phase selection has inherent advantages for small molecules, such as higher affinity and ease of screening of aptamers.

In certain embodiments, the disclosed subject matter provides multiple oligonucleotides and aptamers that can be used for the disclosed system.

Glucose-Binding Aptamers

In certain non-limiting embodiments, an aptamer binds to glucose in an aqueous solution at room temperature or 25° C. with a dissociation constant of less than $10^{-4}$ M (affinity 10) and binds selectively with glucose versus galactose.

In certain non-limiting embodiments, a glucose-binding aptamer includes the sequences CCGTGTGT and either AGTGTCCATTG (SEQ ID NO: 3) or AGTGTCCTTTG (SEQ ID NO: 4) or a variant of any of these sequences that differs in one or two bases by substitution, deletion, insertion or extension, where the aptamer binds to glucose in an aqueous solution at room temperature or 25° C. with a dissociation constant of less than $10^{-4}$ M (affinity 10), and binds selectivity to glucose versus galactose or fructose. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, the glucose-binding aptamer includes the sequences CCGTGTGT and either AGTGTCCATTG (SEQ ID NO: 3) or AGTGTCCTTTG (SEQ ID NO: 4) or a variant thereof has a binding affinity for glucose that is at least about 50 percent or at least about 75 percent the binding affinity of the aptamer having a sequence: ACGACCGTGTGTGTTGCTCTGTAACAGTGTCCATTGTCGT (SEQ ID NO: 5). In certain non-limiting embodiments, the glucose-binding aptamer includes the sequences CCGTGTGT and either AGTGTCCATTG (SEQ ID NO: 3) or AGTGTCCTTTG (SEQ ID NO: 4) or a variant thereof competes with aptamer having a sequence: ACGACCGTGTGTGTTGCTCTGTAACAGTGTCCATTGTCGT (SEQ ID NO: 5) for glucose binding. In certain non-limiting embodiments, a glucose-binding aptamer includes the sequences CCGTGTGT and either AGTGTCCATTG (SEQ ID NO: 3) or AGTGTCCTTTG (SEQ ID NO: 4) or a variant thereof and at least one operative sequence. In certain non-limiting embodiments, a glucose-binding aptamer includes the sequences CCGTGTGT and either AGTGTCCATTG (SEQ ID NO: 3) or AGTGTCCTTTG (SEQ ID NO: 4), or a variant thereof, and at least one operative sequence the that is complementary to a sequence comprised in a sensor oligonucleotide. In certain non-limiting embodiments, a glucose-binding aptamer includes the sequences CCGTGTGT and either AGTGTCCATTG (SEQ ID NO: 3) or AGTGTCCTTTG (SEQ ID NO: 4), or a variant thereof, and at least one operative sequence on either side (flanking) these two sequences. In certain non-limiting embodiments, a glucose-binding aptamer includes the sequences CCGTGTGT and either AGTGTCCATTG (SEQ ID NO: 3) or AGTGTCCTTTG (SEQ ID NO: 4), or a variant thereof, and at least one operative sequence on either side (flanking) these two sequences, where two of the operative sequences contain mutually complementary portions and can form a duplex.

In certain non-limiting embodiments, a glucose-binding aptamer has a predicted secondary structure that comprises two stems connected by sequences that bind to glucose (e.g., binding selectively to glucose versus galactose) and/or one or more of the following: a 4-O—R-glucose epitope, where R is hydrogen, an alkyl group, another carbohydrate or a protein; cellobiose; and/or maltose.

For example, but not by way of limitation, a glucose-binding aptamer can include a sequence selected from:

```
>S-Glu01:
                                        (SEQ ID NO: 6)
CTCTCGGGACGACCGTGTGTGTTGCTCTGTAAC---------AGTGTCC
ATTGTCGTCCC;

>S-Glu02:
                                        (SEQ ID NO: 7)
CTCTCGGGACGACCGTGTGTGGTAGAGTCGTCGGGCTCTAACAGTGTCC
TTTGTCGTCCC;
```

-continued

>S-Glu03:

(SEQ ID NO: 8)

CTCTCGGGACGACCGTGTGTGACGTGCGCCGTGGGGAACGTCAGTGTTC TTTGTCGTCCC;

>S-Glu04:

(SEQ ID NO: 9)

CTCTCGGGACGACCGTGTGTCGACTTAGAGTCG---------AGTGTCC TTTGTCGTCCC; and

>S-Glu05:

(SEQ ID NO: 10)

CTCTCGGGACGACCGTGTGTTGCAATTCTTGCA---------AGTGTTC TTTGTCGTCCC.

In certain non-limiting embodiments, a glucose-binding aptamer includes a core sequence as set forth in a sequence: NNCGTGTGNNNNGTGTCCATTNN (SEQ ID NO: 11). In certain non-limiting embodiments, a glucose-binding aptamer includes a core sequence as set forth in a sequence: NNCGTGTGNNNNGTGTCCATTNN (SEQ ID NO: 11) and has a binding affinity for glucose that is at least about 50 percent or at least about 75 percent the binding affinity of the aptamer having a sequence: ACGACCGTGT GTGTTGCTCTGTAACAGTGTCCATTGTCGT (SEQ ID NO: 5). In certain non-limiting embodiments, a glucose-binding aptamer includes a core sequence as set forth in a sequence: NNCGTGTGNNNNGTGTCCATTNN (SEQ ID NO: 11) competes with aptamer having a sequence: ACGACCGTGTGTGTTGCTCTGTAACAGTGTCCAT-TGTCGT (SEQ ID NO: 5) for glucose binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a glucose-binding aptamer includes a core sequence as set forth in a sequence: NNCGTGTGNNNNGTGTCCATTNN (SEQ ID NO: 11) and at least one operative sequence. In certain non-limiting embodiments, a glucose-binding aptamer includes a core sequence as set forth in a sequence: NNCGTGTGNNNNGTGTCCATTNN (SEQ ID NO: 11) and at least one operative sequence the that is complementary to a sequence included in a sensor oligonucleotide. In certain non-limiting embodiments, a glucose-binding aptamer includes a core sequence as set forth in a sequence: NNCGTGTGNNNNGTGTCCATTNN (SEQ ID NO: 11) and at least one operative sequence on either side (flanking) the core sequence. In certain non-limiting embodiments, a glucose-binding aptamer includes a core sequence as set forth in a sequence: NNCGTGTGNNNNGTGTCCATTNN (SEQ ID NO: 11) and at least one operative sequence on either side (flanking) the core sequence, where two of the operative sequences contain mutually complementary portions and can form a duplex.

In certain non-limiting embodiments, isolated glucose-binding aptamers include the nucleotide sequence of CTCTCGGGACGACCGTGTGTGTTGCTCTGTAACAG TGTCC ATTGTCGTCCC (SEQ ID NO: 6), ACGACCGTGTGTGTTGCTCTGTAACAGTGTCCAT-TGTCGT (SEQ ID NO: 5), or CGACCTGGTGTGTTGCTCTGTAACAGTGTC TAT-TGTCG (SEQ ID NO: 12) or variants of these sequences having at least about 80 percent, or at least about 85 percent, or at least about 90 percent, or at least about 95 percent, or at least about 98 percent homology to the original sequence, for example obtained by substitutions, deletions, and insertions of Watson-Crick base pairs or by mutations at non-conserved positions. Percent homology can be determined using standard software such as BLAST or FASTA. In certain non-limiting embodiments, isolated glucose-binding aptamers include the nucleotide sequence of CTCTCGGGACGACCGTGTGTGTTGCTCTGTAACAG TGTCC ATTGTCGTCCC (SEQ ID NO: 6), ACGACCGTGTGTGTTGCTCTGTAACAGTGTCCAT-TGTCGT (SEQ ID NO: 5), or CGACCTGGTGTGTTGCTCTGTAACAGTGTCTAT-TGTCG (SEQ ID NO: 12). The aptamers can bind to glucose and in their structure-switching formats in which they can respond by an increase in fluorescence or by changes in FET response, or by other spectroscopic signal changes (e.g., circular dichroism spectral changes, Raman spectral changes, or surface-enhanced Raman spectral changes).

Phenylalanine-Binding Aptamers

In certain non-limiting embodiments, an aptamer binds to phenylalanine in an aqueous solution at room temperature or 25° C. with a dissociation constant of less than $10^{-4}$ M and binds selectively with phenylalanine versus tyrosine (or hydroxyl-phenylalanine) or tryptophan.

In certain non-limiting embodiments, a phenylalanine-binding aptamer includes the sequences GCGT and AGC and GGTT or a variant of any of these sequences that differs in one or two bases by substitution, deletion, insertion or extension, where the aptamer binds to phenylalanine in an aqueous solution at room temperature or 25° C. with a dissociation constant of less than 10-M and binds selectively to phenylalanine versus tyrosine (or hydroxyl-phenylalanine) or tryptophan. In certain non-limiting embodiments, the phenylalanine-binding aptamer includes the sequences GCGT and AGC and GGTT, or a variant thereof, has a binding affinity for phenylalanine that is at least about 50 percent or at least about 75 percent the binding affinity of an aptamer having a sequence CTCTCGGGAC GACCGCGTTT CCCAAGAAAG CAAGTATTGG TTGGTCGTCC C (SEQ ID NO: 13), CTCTCGGGAC GACCGGTGGG GGTTCTTTTT CAGGGGAGGT ACGGTCGTCC C (SEQ ID NO: 14), CTCTCGGGAC GACGAGGCTG GATGCATTCG CCGGATGTTC GATGTCGTCC C (SEQ ID NO: 15), OR GACCGGTGGG GGTTCTTTTT CAGGGGAGGT ACGGTC (SEQ ID NO: 16). In certain non-limiting embodiments, the phenylalanine-binding aptamer includes the sequences GCGT and AGC and GGTT, or a variant thereof, and competes with a phenylalanine-binding aptamer having a sequence CTCTCGGGAC GACCGCGTTT CCCAAGAAAG CAAGTATTGG TTGGTCGTCC C (SEQ ID NO: 13), CTCTCGGGAC GACCGGTGGG GGTTCTTTTT CAGGGGAGGT ACGGTCGTCC C (SEQ ID NO: 14), CTCTCGGGAC GACGAGGCTG GATGCATTCG CCG-GATGTTC GATGTCGTCC C (SEQ ID NO: 15), OR GACCGGTGGG GGTTCTTTTT CAGGGGAGGT ACGGTC (SEQ ID NO: 16). In certain non-limiting embodiments, a phenylalanine-binding aptamer includes the sequences GCGT and AGC and GGTT or a variant thereof and further comprises at least one operative sequence. In certain non-limiting embodiments, a phenylalanine-binding aptamer includes the sequences GCGT and AGC and GGTT, or a variant thereof, and at least one operative sequence the that is complementary to a sequence comprised in a sensor oligonucleotide. In certain non-limiting embodiments, a phenylalanine-binding aptamer includes the sequences GCGT and AGC and GGTT, or a variant thereof, and at least one operative sequence on either side (flanking) these three sequences. In certain non-limiting embodiments, a phenylalanine-binding aptamer includes the sequences GCGT and AGC and GGTT, or a variant thereof, and at least one operative sequence on either side (flanking) these three sequences, where two of the operative sequences contain mutually complementary portions and can form a duplex. For example, but not by way of limitation, a phenylalanine-binding aptamer can include e the sequence: CTC TCG GGA CGA CCG CGT TTC CCA AGA AAG CAA GTA TTG GTT GGT CGT CCC (SEQ ID NO: 13) or a portion thereof including the core such as sequences: NNCGNNNNCC AANNNNGNNN GTANNNGTNN (SEQ ID NO: 17) or GACCGCGTTT CCCAAGAAAG CAAGTATTGG TTGGTC (SEQ ID NO: 18).

In certain non-limiting embodiments, a phenylalanine-binding aptamer includes a core sequence as set forth in a sequence: NNCGNNNNCC AANNNNGNNN GTANNNGTNN (SEQ ID NO: 17). In certain non-limiting embodiments, a phenylalanine-binding aptamer includes a core sequence as set forth in a sequence: NNCGNNNNCC AANNNNGNNN GTANNNGTNN (SEQ ID NO: 17) has a binding affinity for phenylalanine that is at least about 50 percent or at least about 75 percent the binding affinity of the aptamer having a sequence: GACCGCGTTT CCCAAGAAAG CAAGTATTGG TTGGTC (SEQ ID NO: 18). In certain non-limiting embodiments, a phenylalanine-binding aptamer includes a core sequence as set forth in a sequence: NNCGNNNNCC AANNNNGNNN GTANNNGTNN (SEQ ID NO: 17) competes with aptamer having a sequence: ACCGCGTTT CCCAAGAAAG CAAGTATTGG TTGGTC (SEQ ID NO: 19) for phenylalanine binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a phenylalanine-binding aptamer includes a core sequence as set forth in a sequence: NNCGNNNNCC AANNNNGNNN GTANNNGTNN (SEQ ID NO: 17) and further includes at least one operative sequence. In certain non-limiting embodiments, a phenylalanine-binding aptamer includes a core sequence as set forth in a sequence: NNCGNNNNCC AANNNNGNNN GTANNNGTNN (SEQ ID NO: 17) and further includes at least one operative sequence, the operative sequence complementary to a sequence included in a sensor oligonucleotide. In certain non-limiting embodiments, a phenylalanine-binding aptamer includes a core sequence as set forth in a sequence: NNCGNNNNCC AANNNNGNNN GTANNNGTNN (SEQ ID NO: 17) and at least one operative sequence on either side (flanking) the core sequence. In certain non-limiting embodiments, a phenylalanine-binding aptamer includes a core sequence as set forth in a sequence: NNCGNNNNCC AANNNNGNNN GTANNNGTNN (SEQ ID NO: 17) and at least one operative sequence on either side (flanking) the core sequence, where two of the operative sequences contain mutually complementary portions and can form a duplex.

In certain non-limiting embodiments, a phenylalanine-binding aptamer includes the sequences GG and GGGGG and GGGG or a variant of any of these sequences that differs in one or two bases by substitution, deletion, insertion or extension, where the aptamer binds to phenylalanine in an aqueous solution at room temperature or 25° C. with a dissociation constant of less than 10' M and binds to phenylalanine selectively versus tyrosine (or hydroxyl-phenylalanine) or tryptophan. In certain non-limiting embodiments, a phenylalanine-binding aptamer includes the sequences GG and GGGGG and GGGG or a variant thereof and further includes at least one operative sequence. In certain non-limiting embodiments, a phenylalanine-binding aptamer includes the sequences GG and GGGGG and GGGG, or a variant thereof, and further includes at least one operative sequence, the operative sequence complementary to a sequence included in a sensor oligonucleotide. In certain non-limiting embodiments, a phenylalanine-binding aptamer includes the sequences GG and GGGGG and GGGG, or a variant thereof, and at least one operative sequence on either side (flanking) these three sequences. In certain non-limiting embodiments, a phenylalanine-binding aptamer includes the sequences GG and GGGGG and GGGG, or a variant thereof, and at least one operative sequence on either side (flanking) these three sequences, where two of the operative sequences contain mutually complementary portions and can form a duplex. For example, but not by way of limitation, a phenylalanine-binding aptamer can include the sequence:

```
                                          (SEQ ID NO: 14)
CTC TCG GGA CGA CCG GTG GGG GTT CTT TTT CAG GGG
AGG TAC GGT CGT CCC.
```

In certain non-limiting embodiments, a phenylalanine-binding aptamer includes a core sequence as set forth in a sequence: NNGTGGGGGN NNNTTTTCNN NNGAGGTANN (SEQ ID NO: 20). In certain non-limiting embodiments, a phenylalanine-binding aptamer includes a core sequence as set forth in a sequence: NNGTGGGGGN NNNTTTTCNN NNGAGGTANN (SEQ ID NO: 20) has a binding affinity for phenylalanine that is at least about 50 percent or at least about 75 percent the binding affinity of the aptamer having a sequence: GACCGGTGGG GGTTCTTTTT CAGGGGAGGT ACGGTC (SEQ ID NO: 16). In certain non-limiting embodiments, a phenylalanine-binding aptamer includes a core sequence as set forth in a sequence: NNGTGGGGGN NNNTTTTCNN NNGAGGTANN (SEQ ID NO: 20) competes with aptamer having a sequence: GACCGGTGGG GGTTCTTTTT CAGGGGAGGT ACGGTC (SEQ ID NO: 16) for phenylalanine binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a phenylalanine-binding aptamer includes a core sequence as set forth in a sequence: NNGTGGGGGN NNNTTTTCNN NNGAGGTANN (SEQ ID NO: 20) and further includes at least one operative sequence. In certain non-limiting embodiments, a phenylalanine-binding aptamer includes a core sequence as set forth in a sequence: NNGTGGGGGN NNNTTTTCNN NNGAGGTANN (SEQ ID NO: 20) and further includes at least one operative sequence, the operative sequence complementary to a sequence included in a sensor oligonucleotide. In certain non-limiting embodiments, a phenylalanine-binding aptamer includes a core sequence as set forth in a sequence: NNGTGGGGGN NNNTTTTCNN NNGAGGTANN (SEQ ID NO: 20) and at least one operative sequence on either side (flanking) the core sequence. In certain non-limiting embodiments, a phenylalanine-binding aptamer includes a core sequence as set forth in a sequence: NNGTGGGGGN NNNTTTTCNN NNGAGGTANN (SEQ ID NO: 20) and at least one operative sequence on either side (flanking) the core sequence, where two of the operative sequences contain mutually complementary portions and can form a duplex.

In certain non-limiting embodiments, a phenylalanine-binding aptamer includes the sequences GAGG and CATT or CCGG and TGTT or a variant of any of these sequences that differs in one or two bases by substitution, deletion, insertion or extension, where the aptamer binds to phenylalanine in an aqueous solution at room temperature or 25° C. with a dissociation constant of less than $10^{-4}$ M and binds to phenylalanine selectively versus tyrosine (or hydroxyl-phenylalanine) or tryptophan. In certain non-limiting embodiments, a phenylalanine-binding aptamer includes the sequences GAGG and CATT or CCGG and TGTT or a variant thereof and further includes at least one operative sequence. In certain non-limiting embodiments, a phenylalanine-binding aptamer includes the sequences GAGG and CATT or CCGG and TGTT, or a variant thereof, and further includes at least one operative sequence, the operative sequence complementary to a sequence included in a sensor oligonucleotide. In certain non-limiting embodiments, a phenylalanine-binding aptamer includes the sequences GAGG and CATT or CCGG and TGTT, or a variant thereof, and at least one operative sequence on either side (flanking) these four sequences. In certain non-limiting embodiments, a phenylalanine-binding aptamer includes the sequences GAGG and CATT or CCGG and TGTT, or a variant thereof, and at least one operative sequence on either side (flanking) these four sequences, where two of the operative sequences contain mutually complementary portions and can form a duplex. For example, but not by way of limitation, a phenylalanine-binding aptamer can include the sequence: CTC TCG GGA CGA GGC TGG ATG CAT TCG CCG GAT GTT CGA TGT CGT CCC (SEQ ID NO: 21) or related sequence: CGACGAGGCT GGATGCATTC GCCGGATGTT CGATGTCG (SEQ ID NO: 22).

In certain non-limiting embodiments, a phenylalanine-binding aptamer includes a core sequence as set forth in a sequence: NNNAGGCTGG ATGCATTCGC CGGATGTTCG ANNN (SEQ ID NO: 23). In certain non-limiting embodiments, a phenylalanine-binding aptamer includes a core sequence as set forth in a sequence: NNNAGGCTGG ATGCATTCGC CGGATGTTCG ANNN (SEQ ID NO: 23) has a binding affinity for phenylalanine that is at least about 50 percent or at least about 75 percent the binding affinity of the aptamer having a sequence: CGACGAGGCT GGATGCATTC GCCGGATGTT CGATGTCG (SEQ ID NO: 22). In certain non-limiting embodiments, a phenylalanine-binding aptamer includes a core sequence as set forth in a sequence: NNNAGGCTGG ATGCATTCGC CGGATGTTCG ANNN (SEQ ID NO: 23) competes with aptamer having a sequence: CGACGAGGCT GGATGCATTC GCCGGATGTT CGATGTCG (SEQ ID NO: 22) for phenylalanine binding. In non-limiting embodiments, the aptamer has a length of between about 20 and about 100 nucleotides, or between about 20 and 80 nucleotides, or between about 20 and 70 nucleotides, or between about 20 and 60 nucleotides. In certain non-limiting embodiments, a phenylalanine-binding aptamer includes a core sequence as set forth in a sequence: NNNAGGCTGG ATGCATTCGC CGGATGTTCG ANNN (SEQ ID NO: 23) and further includes at least one operative sequence. In certain non-limiting embodiments, a phenylalanine-binding aptamer includes a core sequence as set forth in a sequence: NNNAGGCTGG ATGCATTCGC CGGATGTTCG ANNN (SEQ ID NO: 23) and further includes at least one operative sequence, the operative sequence complementary to a sequence included in a sensor oligonucleotide. In certain non-limiting embodiments, a phenylalanine-binding aptamer includes a core sequence as set forth in a sequence: NNNAGGCTGG ATGCATTCGC CGGATGTTCG ANNN (SEQ ID NO: 23) and at least one operative sequence on either side (flanking) the core sequence. In certain non-limiting embodiments, a phenylalanine-binding aptamer includes a core sequence as set forth in a sequence: NNNAGGCTGG ATGCATTCGC CGGATGTTCG ANNN (SEQ ID NO: 23) and at least one operative sequence on either side (flanking) the core sequence, where two of the operative sequences contain mutually complementary portions and can form a duplex.

In certain non-limiting embodiments, isolated phenylalanine-binding aptamers include the nucleotide sequence of CTCTCGGGAC GACCGCGTTT CCCAAGAAAG CAAGTATTGG TTGGTCGTCC C (SEQ ID NO: 13), CTCTCGGGAC GACCGGTGGG GGTTCTTTTT CAGGGGAGGT ACGGTCGTCC C (SEQ ID NO: 14), CTCTCGGGAC GACGAGGCTG GATGCATTCG CCGGATGTTC GATGTCGTCC C (SEQ ID NO: 15), GACCGGTGGG GGTTCTTTTT CAGGGGAGGT ACGGTC (SEQ ID NO: 16), GACCGCGTTT CCCAAGAAAG CAAGTATTGG TTGGTC (SEQ ID NO: 18), CGACGAGGCT GGATGCATTC GCCGGATGTT CGATGTCG (SEQ ID NO: 22) or variants of these sequences having at least about 80 percent, or at least about 85 percent, or at least about 90 percent, or at least about 95 percent, or at least about 98 percent homology to the original sequence, for example obtained by substitutions, deletions, and insertions of Watson-Crick base pairs or by mutations at non-conserved positions. Percent homology can be determined using standard software such as BLAST or FASTA. In certain non-limiting embodiments, isolated phenylalanine-binding aptamers include the nucleotide sequence of

```
                                        (SEQ ID NO: 13)
CTCTCGGGAC GACCGCGTTT CCCAAGAAAG CAAGTATTGG
TTGGTCGTCC C,

                                        (SEQ ID NO: 14)
CTCTCGGGAC GACCGGTGGG GGTTCTTTTT CAGGGGAGGT
ACGGTCGTCC C,

                                        (SEQ ID NO: 15)
CTCTCGGGAC GACGAGGCTG GATGCATTCG CCGGATGTTC
GATGTCGTCC C,

                                        (SEQ ID NO: 16)
GACCGGTGGG GGTTCTTTTT CAGGGGAGGT ACGGTC,

                                        (SEQ ID NO: 18)
GACCGCGTTT CCCAAGAAAG CAAGTATTGG TTGGTC, OR

                                        (SEQ ID NO: 22)
CGACGAGGCT GGATGCATTC GCCGGATGTT CGATGTCG.
```

The aptamers can bind to phenylalanine and in their structure-switching formats they can respond by an increase in fluorescence, or by changes in FET response, or by other spectroscopic signal changes (e.g., circular dichroism spectral changes, Raman spectral changes, or surface-enhanced Raman spectral changes).

Sphingosine-1-Phosphate-Binding Aptamers

In certain non-limiting embodiments, an aptamer binds to sphingosine-1-phosphate in an aqueous solution at room temperature or 25° C. with a dissociation constant of less than $10^{-4}$ M.

In certain non-limiting embodiments, a sphingosine-1-phosphate-binding aptamer includes the sequences GG and GGGG and GGGGG or a variant of any of these sequences that differs in one or two bases by substitution, deletion, insertion or extension, where the aptamer binds to sphingosine-1-phosphate in an aqueous solution at room temperature or 25° C. with a dissociation constant of less than $10^{-4}$ M and binds selectively to sphingosine-1-phosphate. In certain non-limiting embodiments, a sphingosine-1-phosphate-binding aptamer includes the sequences GG and GGGG and GGGGG or a variant thereof and further includes at least one operative sequence. In certain non-limiting embodiments, a sphingosine-1-phosphate-binding aptamer includes the sequences GG and GGGG and GGGGG, or a variant thereof, and further includes at least one operative sequence, the operative sequence complementary to a sequence included in a sensor oligonucleotide. In certain non-limiting embodiments, a sphingosine-1-phosphate-binding aptamer includes the sequences GG and GGGG and GGGGG, or a variant thereof, and at least one operative sequence on either side (flanking) these three sequences. In certain non-limiting embodiments, a sphingosine-1-phosphate-binding aptamer includes the sequences GG and GGGG and GGGGG or a variant thereof, and at least one operative sequence on either side (flanking) these three sequences, where two of the operative sequences contain mutually complementary portions and can form a duplex.

For example, but not by way of limitation, a sphingosine-1-phosphate-binding aptamer can include the sequence: CTC TCG GGA CGA CGT GGT GTG GGA GAA AGA ATT TTC ATT GGG GTA GGG GGT CGT CCC (SEQ ID NO: 24) or related sequence: ACGACGTGGT GTGGGAGAAA GAATTTTCAT TGGGGTAGGG GGTCGT (SEQ ID NO: 25).

In certain non-limiting embodiments, a sphingosine-1-phosphate-binding aptamer includes a core sequence as set forth in a sequence: NNGTGGTGTG GGAGNNCATT GGGGTAGGGG NN (SEQ ID NO: 26). In certain non-limiting embodiments, a sphingosine-1-phosphate-binding aptamer includes a core sequence as set forth in a sequence: NNGTGGTGTG GGAGNNCATT GGGGTAGGGG NN (SEQ ID NO: 26) has a binding affinity for sphingosine-1-phosphate that is at least about 50 percent or at least about 75 percent the binding affinity of the aptamer having a sequence: ACGACGTGGT GTGGGAGAAA GAATTTTCAT TGGGGTAGGG GGTCGT (SEQ ID NO: 25). In certain non-limiting embodiments, a sphingosine-1-phosphate-binding aptamer includes a core sequence as set forth in a sequence: NNGTGGTGTG GGAGNNCATT GGGGTAGGGG NN (SEQ ID NO: 26) competes with aptamer having a sequence: ACGACGTGGT GTGGGAGAAA GAATTTTCAT TGGGGTAGGG GGTCGT (SEQ ID NO: 25) for sphingosine-1-phosphate binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a sphingosine-1-phosphate-binding aptamer includes a core sequence as set forth in a sequence: NNGTGGTGTG GGAGNNCATT GGGGTAGGGG NN (SEQ ID NO: 26) and further includes at least one operative sequence. In certain non-limiting embodiments, a sphingosine-1-phosphate-binding aptamer includes a core sequence as set forth in a sequence: NNGTGGTGTG GGAGNNCATT GGGGTAGGGG NN (SEQ ID NO: 26) and further includes at least one operative sequence, the operative sequence complementary to a sequence included in a sensor oligonucleotide. In certain non-limiting embodiments, a sphingosine-1-phosphate-binding aptamer includes a core sequence as set forth in a sequence: NNGTGGTGTG GGAGNNCATT GGGGTAGGGG NN (SEQ ID NO: 26) and at least one operative sequence on either side (flanking) the core sequence. In certain non-limiting embodiments, a sphingosine-1-phosphate-binding aptamer includes a core sequence as set forth in a sequence: NNGTGGTGTG GGAGNNCATT GGGGTAGGGG NN (SEQ ID NO: 26) and at least one operative sequence on either side (flanking) the core sequence, where two of the operative sequences contain mutually complementary portions and can form a duplex.

In certain non-limiting embodiments, isolated sphingosine-1-phosphate-binding aptamers include the nucleotide sequence of CTCTCGGGAC GACGTGGTGT GGGAGAAAGA ATTTTCATTG GGGTAGGGGG TCGTCCC (SEQ ID NO: 24), ACGACGTGGT GTGGGAGAAA GAATTTTCAT TGGGGTAGGG GGTCGT (SEQ ID NO: 25), or variants of these sequences having at least about 80 percent, or at least about 85 percent, or at least about 90 percent, or at least about 95 percent, or at least about 98 percent homology to the original sequence, for example obtained by substitutions, deletions, and insertions of Watson-Crick base pairs or by mutations at non-conserved positions. Percent homology can be determined using standard software such as BLAST or FASTA. In certain non-limiting embodiments, isolated sphingosine-1-phosphate-binding aptamers include the nucleotide sequence of CTCTCGGGAC GACGTGGTGT GGGAGAAAGA ATTTTCATTG GGGTAGGGGG TCGTCCC (SEQ ID NO: 24) OR ACGACGTGGT GTGGGAGAAA GAATTTTCAT TGGGGTAGGG GGTCGT (SEQ ID NO: 25). The aptamers can bind to sphingosine-1-phosphate and in their structure-switching formats they can respond by an increase in fluorescence, or by changes in FET response, or by other spectroscopic signal changes (e.g., circular dichroism spectral changes, Raman spectral changes, or surface-enhanced Raman spectral changes).

Dopamine-Binding Aptamers

In certain non-limiting embodiments, an aptamer binds to dopamine in an aqueous solution at room temperature or 25° C. with a dissociation constant of less than $10^{-4}$ M and binds selectively with dopamine.

In certain non-limiting embodiments, a dopamine-binding aptamer includes the sequences CCAGT and GGTGT or a variant of any of these sequences that differs in one or two bases by substitution, deletion, insertion or extension, where the aptamer binds to dopamine in an aqueous solution at room temperature or 25° C. with a dissociation constant of less than $10^{-4}$ M and binds to dopamine selectively versus serotonin or norepinephrine. In certain non-limiting embodiments, a dopamine-binding aptamer includes the sequences CCAGT and GGTGT or a variant thereof and further includes at least one operative sequence. In certain non-limiting embodiments, a dopamine-binding aptamer includes the sequences CCAGT and GGTGT, or a variant thereof, and further includes at least one operative sequence, the operative sequence complementary to a sequence included in a sensor oligonucleotide. In certain non-limiting embodiments, a dopamine-binding aptamer includes the sequences CCAGT and GGTGT, or a variant thereof, and at least one operative sequence on either side (flanking) these two sequences. In certain non-limiting embodiments, a dopamine-binding aptamer includes the sequences CCAGT and GGTGT or a variant thereof, and at least one operative sequence on either side (flanking) these two sequences, where two of the operative sequences contain mutually complementary portions and can form a duplex. For example, but not by way of limitation, a dopamine-binding aptamer can include the sequence: CTC TCG GGA CGA CGC CAG TTT GAA GGT TCG TTC GCA GGT GTG GAG TGA CGT CCC (SEQ ID NO: 27) or related sequence: CGACGCCAGT TTGAAGGTTC GTTCGCAGGT GTG-GAGTGAC GTCG (SEQ ID NO: 28). In certain non-limiting embodiments, a dopamine-binding aptamer includes a core sequence as set forth in a sequence: NGCCAGTTTN NNGGTTCGNN NGCAGGTGTG GAGTGACN (SEQ ID NO: 29). In certain non-limiting embodiments, a dopamine-binding aptamer includes a core sequence as set forth in a sequence: NGCCAGTTTN NNGGTTCGNN NGCAGGTGTG GAGTGACN (SEQ ID NO: 29) has a binding affinity for dopamine that is at least about 50 percent or at least about 75 percent the binding affinity of the aptamer having a sequence: CGACGCCAGT TTGAAGGTTC GTTCGCAGGT GTGGAGTGAC GTCG (SEQ ID NO: 28). In certain non-limiting embodiments, a dopamine-binding aptamer includes a core sequence as set forth in a sequence: NGCCAGTTTN NNGGTTCGNN NGCAGGTGTG GAGTGACN (SEQ ID NO: 29) competes with aptamer having a sequence: CGACGCCAGT TTGAAGGTTC GTTCGCAGGT GTGGAGTGAC GTCG (SEQ ID NO: 28) for dopamine binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a dopamine-binding aptamer includes a core sequence as set forth in a sequence: NGCCAGTTTN NNGGTTCGNN NGCAGGTGTG GAGTGACN (SEQ ID NO: 29) and further includes at least one operative sequence. In certain non-limiting embodiments, a dopamine-binding aptamer includes a core sequence as set forth in a sequence: NGCCAGTTTN NNGGTTCGNN NGCAGGTGTG GAGTGACN (SEQ ID NO: 29) and further includes at least one operative sequence, the operative sequence complementary to a sequence included in a sensor oligonucleotide. In certain non-limiting embodiments, a dopamine-binding aptamer includes a core sequence as set forth in a sequence: NGCCAGTTTN NNGGTTCGNN NGCAGGTGTG GAGTGACN (SEQ ID NO: 29) and at least one operative sequence on either side (flanking) the core sequence. In certain non-limiting embodiments, a dopamine-binding aptamer includes a core sequence as set forth in a sequence: NGCCAGTTTN NNGGTTCGNN NGCAGGTGTG GAGTGACN (SEQ ID NO: 29) and at least one operative sequence on either side (flanking) the core sequence, where two of the operative sequences contain mutually complementary portions and can form a duplex.

In certain non-limiting embodiments, a dopamine-binding aptamer includes the sequences GGG and GGGG or a variant of any of these sequences that differs in one or two bases by substitution, deletion, insertion or extension, where the aptamer binds to dopamine in an aqueous solution at room temperature or 25° C. with a dissociation constant of less than $10^{-4}$ M and binds to dopamine selectively versus serotonin or tyrosine. In certain non-limiting embodiments, a dopamine-binding aptamer includes the sequences GGG and GGGG or a variant thereof and further includes at least one operative sequence. In certain non-limiting embodiments, a dopamine-binding aptamer includes the sequences GGG and GGGG, or a variant thereof, and further includes at least one operative sequence, the operative sequence complementary to a sequence included in a sensor oligonucleotide. In certain non-limiting embodiments, a dopamine-binding aptamer includes the sequences GGG and GGGG, or a variant thereof, and at least one operative sequence on either side (flanking) these two sequences. In certain non-limiting embodiments, a dopamine-binding aptamer includes the sequences GGG and GGGG or a variant thereof, and at least one operative sequence on either side (flanking) these two sequences, where two of the operative sequences contain mutually complementary portions and can form a duplex. For example, but not by way of limitation, a dopamine-binding aptamer can include the sequence: CTC TCG GGA CGA CTG CAG CCT GGG GTT GTG GGG GGT AGG GGA GGT CTG AGT CGT CCC (SEQ ID NO: 30) or related sequence: CGACTGCAGC CTGGGGTTGT GGGGGGTAGG GGAGGTCTGA GTCG (SEQ ID NO: 31). In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32). In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32) has a binding affinity for dopamine that is at least about 50 percent or at least about 75 percent the binding affinity of the aptamer having a sequence: CGACTGCAGC CTGGGGTTGT GGGGGGTAGG GGAGGTCTGA GTCG (SEQ ID NO: 31). In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32) competes with aptamer having a sequence: CGACTGCAGC CTGGGGTTGT GGGGGGTAGG GGAGGTCTGA GTCG (SEQ ID NO: 31) for dopamine binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32) and further includes at least one operative sequence. In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32) and further includes at least one operative sequence, the operative sequence complementary to a sequence included in a sensor oligonucleotide. In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32) and at least one operative sequence on either side (flanking) the core sequence. In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32) and at least one operative sequence on either side (flanking) the core sequence, where two of the operative sequences contain mutually complementary portions and can form a duplex.

In certain non-limiting embodiments, a dopamine-binding aptamer includes the sequences CACAG and CACAA or a variant of any of these sequences that differs in one or two bases by substitution, deletion, insertion or extension, where the aptamer binds to dopamine in an aqueous solution at room temperature or 25° C. with a dissociation constant of less than 10' M and binds to dopamine selectively versus serotonin, melatonin or tyrosine). In certain non-limiting embodiments, a dopamine-binding aptamer includes the sequences CACAG and CACAA or a variant thereof and further includes at least one operative sequence. In certain non-limiting embodiments, a dopamine-binding aptamer includes the sequences CACAG and CACAA or a variant thereof, and further includes at least one operative sequence, the operative sequence complementary to a sequence included in a sensor oligonucleotide. In certain non-limiting embodiments, a dopamine-binding aptamer includes the sequences CACAG and CACAA, or a variant thereof, and at least one operative sequence on either side (flanking) these two sequences. In certain non-limiting embodiments, a dopamine-binding aptamer includes the sequences CACAG and CACAA or a variant thereof, and at least one operative sequence on either side (flanking) these two sequences, where two of the operative sequences contain mutually complementary portions and can form a duplex. For example, but not by way of limitation, a dopamine-binding aptamer can include the sequence: CTC TCG GGA CGA CCA CAC AGA GGC ACA ACT CGC AGG AGC AAA GCG GCA GGT CGT CCC (SEQ ID NO: 33) or related sequence: CGACCACACA GAGGCACAAC TCGCAG-GAGC AAAGCGGCAG GTCG (SEQ ID NO: 34). In certain non-limiting embodiments, a dopamine-binding aptamer includes a core sequence as set forth in a sequence: NNACACAGAG GCACAACTNN NAGGAGCAAA NNNGCANN (SEQ ID NO: 35). In certain non-limiting embodiments, a dopamine-binding aptamer includes a core sequence as set forth in a sequence: NNACACAGAG GCACAACTNN NAGGAGCAAA NNNGCANN (SEQ ID NO: 35) has a binding affinity for dopamine that is at least about 50 percent or at least about 75 percent the binding affinity of the aptamer having a sequence: CGACCACACA GAGGCACAAC TCGCAGGAGC AAAGCGGCAG GTCG (SEQ ID NO: 34). In certain non-limiting embodiments, a dopamine-binding aptamer includes a core sequence as set forth in a sequence: NTGCAGCCTG GGGTTGTGGG GGGTAGGGGA GGTCTGAN (SEQ ID NO: 32) competes with aptamer having a sequence: CGAC-CACACA GAGGCACAAC TCGCAGGAGC AAAGCGGCAG GTCG (SEQ ID NO: 34) for dopamine binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a dopamine-binding aptamer includes a core sequence as set forth in a sequence: NNACACAGAG GCACAACTNN NAGGAGCAAA NNNGCANN (SEQ ID NO: 35) and further includes at least one operative sequence. In certain non-limiting embodiments, a dopamine-binding aptamer includes a core sequence as set forth in a sequence: NNACACAGAG GCACAACTNN NAGGAGCAAA NNNGCANN (SEQ ID NO: 35) and further includes at least one operative sequence, the operative sequence complementary to a sequence included in a sensor oligonucleotide. In certain non-limiting embodiments, a dopamine-binding aptamer includes a core sequence as set forth in a sequence: NNACACAGAG GCACAACTNN NAGGAGCAAA NNNGCANN (SEQ ID NO: 35) and at least one operative sequence on either side (flanking) the core sequence. In certain non-limiting embodiments, a dopamine-binding aptamer includes a core sequence as set forth in a sequence: NNACACAGAG GCACAACTNN NAGGAGCAAA NNNGCANN (SEQ ID NO: 35) and at least one operative sequence on either side (flanking) the core sequence, where two of the operative sequences contain mutually complementary portions and can form a duplex.

In certain non-limiting embodiments, a dopamine-binding aptamer includes the sequences GGGG and GG or a variant of any of these sequences that differs in one or two bases by substitution, deletion, insertion or extension, where the aptamer binds to dopamine in an aqueous solution at room temperature or 25° C. with a dissociation constant of less than 10' M and binds to dopamine selectively versus serotonin, melatonin or tyrosine. In certain non-limiting embodiments, a dopamine-binding aptamer includes the sequences GGGG and GG or a variant thereof and further includes at least one operative sequence. In certain non-limiting embodiments, a dopamine-binding aptamer includes the sequences GGGG and GG or a variant thereof, and further includes at least one operative sequence, the operative sequence complementary to a sequence included in a sensor oligonucleotide. In certain non-limiting embodiments, a dopamine-binding aptamer includes the sequences GGGG and GG, or a variant thereof, and at least one operative sequence on either side (flanking) these two sequences. In certain non-limiting embodiments, a dopamine-binding aptamer includes the sequences GGGG and GG or a variant thereof, and at least one operative sequence on either side (flanking) these two sequences, where two of the operative sequences contain mutually complementary portions and can form a duplex. For example, but not by way of limitation, a dopamine-binding aptamer can include the sequence: CTC TCG GGA CGA CGG GGA GTT AGC ATG ACG GCA ACT TTA GTA CTT CGT CCC (SEQ ID NO: 36) or related sequence: CGACGGGGAG GAGTTAGCAT GACGGCAACT TTAGTACTTC GTCG (SEQ ID NO: 37). In certain non-limiting embodiments, a dopamine-binding aptamer includes a core sequence as set forth in a sequence: NGGGGAGGAN NTTTAGTACT TCN (SEQ ID NO: 38). In certain non-limiting embodiments, a dopamine-binding aptamer includes a core sequence as set forth in a sequence: NGGGGAGGAN NTTTAGTACT TCN (SEQ ID NO: 38) has a binding affinity for dopamine that is at least about 50 percent or at least about 75 percent the binding affinity of the aptamer having a sequence: CGACGGGGAG GAGTTAG-CAT GACGGCAACT TTAGTACTTC GTCG (SEQ ID NO: 37). In certain non-limiting embodiments, a dopamine-binding aptamer includes a core sequence as set forth in a sequence: NGGGGAGGAN NTTTAGTACT TCN (SEQ ID NO: 38) competes with aptamer having a sequence: CGACGGGGAG GAGTTAGCAT GACGGCAACT TTAGTACTTC GTCG (SEQ ID NO: 37) for dopamine binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a dopamine-binding aptamer includes a core sequence as set forth in a sequence: NGGGGAGGAN NTTTAGTACT TCN (SEQ ID NO: 38) and further includes at least one operative sequence. In certain non-limiting embodiments, a dopamine-binding aptamer includes a core sequence as set forth in a sequence: NGGGGAGGAN NTTTAGTACT TCN (SEQ ID NO: 38) and further includes at least one operative sequence, the operative sequence complementary to a sequence included in a sensor oligonucleotide. In certain non-limiting embodiments, a dopamine-binding aptamer includes a core sequence as set forth in a sequence: NGGGGAGGAN NTTTAGTACT TCN (SEQ ID NO: 38) and at least one operative sequence on either side (flanking) the core sequence. In certain non-limiting embodiments, a dopamine-binding aptamer includes a core sequence as set forth in a sequence: NGGGGAGGAN NTTTAGTACT TCN (SEQ ID NO: 38) and at least one operative sequence on either side (flanking) the core sequence, where two of the operative sequences contain mutually complementary portions and can form a duplex.

In certain non-limiting embodiments, a dopamine-binding aptamer includes the sequences GGGG and GG or a variant of any of these sequences that differs in one or two bases by substitution, deletion, insertion or extension, where the aptamer binds to dopamine in an aqueous solution at room temperature or 25° C. with a dissociation constant of less than 10' M and binds to dopamine selectively versus serotonin, melatonin or tyrosine. In certain non-limiting embodiments, a dopamine-binding aptamer includes the sequences GGGG and GG or a variant thereof and further includes at least one operative sequence. In certain non-limiting embodiments, a dopamine-binding aptamer includes the sequences GGGG and GG or a variant thereof, and further includes at least one operative sequence, the operative sequence complementary to a sequence included in a sensor oligonucleotide. In certain non-limiting embodiments, a dopamine-binding aptamer includes the sequences GGGG and GG, or a variant thereof, and at least one operative sequence on either side (flanking) these two sequences. In certain non-limiting embodiments, a dopamine-binding aptamer includes the sequences GGGG and GG or a variant thereof, and at least one operative sequence on either side (flanking) these two sequences, where two of the operative sequences contain mutually complementary portions and can form a duplex. For example, but not by way of limitation, a dopamine-binding aptamer can include the sequence: CTC TCG GGA CGA CCA CTT CAG ACG CTC AAC GTT TGG GGA GGC ACG GCA GGT CGT CCC (SEQ ID NO: 39) or related sequence: CGACCACTTC AGACGCTCAA CGTTTGGGGA GGCACGGCAG GTCG (SEQ ID NO: 40). In certain non-limiting embodiments, a dopamine-binding aptamer includes a core sequence as set forth in a sequence: NCACNNNNNN NGCTCAACNN NNNNNGAGGC ACGGCAGN (SEQ ID NO: 41). In certain non-limiting embodiments, a dopamine-binding aptamer includes a core sequence as set forth in a sequence: NCACNNNNNN NGCTCAACNN NNNNNGAGGC ACGGCAGN (SEQ ID NO: 41) has a binding affinity for dopamine that is at least about 50 percent or at least about 75 percent the binding affinity of the aptamer having a sequence: CGACCACTTC AGACGCTCAA CGTTTGGGGA GGCACGGCAG GTCG (SEQ ID NO: 40). In certain non-limiting embodiments, a dopamine-binding aptamer includes a core sequence as set forth in a sequence: NCACNNNNNN NGCTCAACNN NNNNNGAGGC ACGGCAGN (SEQ ID NO: 41) competes with aptamer having a sequence: CGACCACTTC AGACGCTCAA CGTTTGGGGA GGCACGGCAG GTCG (SEQ ID NO: 40) for dopamine binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a dopamine-binding aptamer includes a core sequence as set forth in a sequence: NCACNNNNNN NGCTCAACNN NNNNNGAGGC ACGGCAGN (SEQ ID NO: 41) and further includes at least one operative sequence. In certain non-limiting embodiments, a dopamine-binding aptamer includes a core sequence as set forth in a sequence: NCACNNNNNN NGCTCAACNN NNNNNGAGGC ACGGCAGN (SEQ ID NO: 41) and further includes at least one operative sequence, the operative sequence complementary to a sequence included in a sensor oligonucleotide. In certain non-limiting embodiments, a dopamine-binding aptamer includes a core sequence as set forth in a sequence: NCACNNNNNN NGCTCAACNN NNNNNGAGGC ACGGCAGN (SEQ ID NO: 41) and at least one operative sequence on either side (flanking) the core sequence. In certain non-limiting embodiments, a dopamine-binding aptamer includes a core sequence as set forth in a sequence: NCACNNNNNN NGCTCAACNN NNNNNGAGGC ACGGCAGN (SEQ ID NO: 41) and at least one operative sequence on either side (flanking) the core sequence, where two of the operative sequences contain mutually complementary portions and can form a duplex.

In certain non-limiting embodiments, isolated dopamine-binding aptamers include the nucleotide sequence of CTCTCGGGAC GACGCCAGTT TGAAGGTTCG TTCGCAGGTG TGGAGTGACG TCGTCCC (SEQ ID NO: 42), CGACGCCAGT TTGAAGGTTC GTTCGCAGGT GTGGAGTGAC GTCG (SEQ ID NO: 28), CTCTCGGGAC GACTGCAGCC TGGGGTTGTG GGGGGTAGGG GAGGTCTGAG TCGTCCC (SEQ ID NO: 30), CGACTGCAGC CTGGGGTTGT GGGGGGTAGG GGAGGTCTGA GTCG (SEQ ID NO: 31), CTCTCGGGAC GACCACACAG AGGCACAACT CGCAGGAGCA AAGCGGCAGG TCGTCCC (SEQ ID NO: 33), CGACCACACA GAGGCACAAC TCGCAGGAGC AAAGCGGCAG GTCG (SEQ ID NO: 34), CTCTCGGGAC GACGGGGAGG AGTTAGCATG ACGGCAACTT TAGTACTTCG TCGTCCC (SEQ ID NO: 43), CGACGGGGAG GAGTTAGCAT GACGGCAACT TTAGTACTTC GTCG (SEQ ID NO: 37), CTCTCGGGAC GACCACTTCA GACGCTCAAC GTTTGGGGAG GCACGGCAGG TCGTCCC (SEQ ID NO: 39), CGACCACTTC AGACGCTCAA CGTTTGGGGA GGCACGGCAG GTCG (SEQ ID NO: 40) or variants of these sequences having at least about 80 percent, or at least about 85 percent, or at least about 90 percent, or at least about 95 percent, or at least about 98 percent homology to the original sequence, for example obtained by substitutions, deletions, and insertions of Watson-Crick base pairs or by mutations at non-conserved positions. Percent homology can be determined using standard software such as BLAST or FASTA. In certain non-limiting embodiments, isolated dopamine-binding aptamers include the nucleotide sequence of CTCTCGGGAC GACGCCAGTT TGAAGGTTCG TTCGCAGGTG TGGAGTGACG TCGTCCC (SEQ ID NO: 42), CGACGCCAGT TTGAAGGTTC GTTCGCAGGT GTGGAGTGAC GTCG (SEQ ID NO: 28), CTCTCGGGAC GACTGCAGCC TGGGGTTGTG GGGGGTAGGG GAGGTCTGAG TCGTCCC (SEQ ID NO: 30), CGACTGCAGC CTGGGGTTGT GGGGGGTAGG GGAGGTCTGA GTCG (SEQ ID NO: 31), CTCTCGGGAC GACCACACAG AGGCACAACT CGCAGGAGCA AAGCGGCAGG TCGTCCC (SEQ ID NO: 33), CGACCACACA GAGGCACAAC TCGCAGGAGC AAAGCGGCAG GTCG (SEQ ID NO: 34), CTCTCGGGAC GACGGGGAGG AGTTAGCATG ACGGCAACTT TAGTACTTCG TCGTCCC (SEQ ID NO: 43), CGACGGGGAG GAGTTAGCAT GACGGCAACT TTAGTACTTC GTCG (SEQ ID NO: 37), CTCTCGGGAC GACCACTTCA GACGCTCAAC GTTTGGGGAG GCACGGCAGG TCGTCCC (SEQ ID NO: 39), or CGAC- CACTTC AGACGCTCAA CGTTTGGGGA GGCACGGCAG GTCG (SEQ ID NO: 40). The aptamers can bind to dopamine and in their structure-switching formats they can respond by an increase in fluorescence, or by changes in FET response, or by other spectroscopic signal changes (e.g., circular dichroism spectral changes, Raman spectral changes, or surface-enhanced Raman spectral changes).

Serotonin-Binding Aptamers

In certain non-limiting embodiments, an aptamer binds to serotonin in an aqueous solution at room temperature or 25° C. with a dissociation constant of less than $10^{-4}$ M and binds selectively with serotonin versus dopamine, melatonin, or 5-hydroxytryptophan.

In certain non-limiting embodiments, a serotonin-binding aptamer includes the sequences GG and GGGG and GGG or a variant of any of these sequences that differs in one or two bases by substitution, deletion, insertion or extension, where the aptamer binds to serotonin in an aqueous solution at room temperature or 25° C. with a dissociation constant of less than $10^{-4}$ M and binds to serotonin selectively versus dopamine, melatonin, or 5-hydroxytryptophan. In certain non-limiting embodiments, a serotonin-binding aptamer includes the sequences GG and GGGG and GGG or a variant thereof and further includes at least one operative sequence. In certain non-limiting embodiments, a serotonin-binding aptamer includes the sequences GG and GGGG and GGG or a variant thereof, and further includes at least one operative sequence, the operative sequence complementary to a sequence included in a sensor oligonucleotide. In certain non-limiting embodiments, a serotonin-binding aptamer includes the sequences GG and GGGG and GGG, or a variant thereof, and at least one operative sequence on either side (flanking) these three sequences. In certain non-limiting embodiments, a serotonin-binding aptamer includes the sequences GG and GGGG and GGG or a variant thereof, and at least one operative sequence on either side (flanking) these three sequences, where two of the operative sequences contain mutually complementary portions and can form a duplex.

For example, but not by way of limitation, a serotonin-binding aptamer can include the sequence: CTC TCG GGA CGA CTG GTA GGC AGA TAG GGG AAG CTG ATT CGA TGC GTG GGT CGT CCC (SEQ ID NO: 44) or related sequence: CGACTGGTAG GCAGATAGGG GAAGCTGATT CGATGCGTGG GTCG (SEQ ID NO: 45). In certain non-limiting embodiments, a serotonin-binding aptamer includes a core sequence as set forth in a sequence: NTGGTAGNNN GATAGGGNNN GCTGANNNGA NNNGTGGN (SEQ ID NO: 46). In certain non-limiting embodiments, a serotonin-binding aptamer includes a core sequence as set forth in a sequence: NTGGTAGNNN GATAGGGNNN GCTGANNNGA NNNGTGGN (SEQ ID NO: 46) has a binding affinity for serotonin that is at least about 50 percent or at least about 75 percent the binding affinity of the aptamer having a sequence: CGACTGGTAG GCAGATAGGG GAAGCTGATT CGATGCGTGG GTCG (SEQ ID NO: 45). In certain non-limiting embodiments, a serotonin-binding aptamer includes a core sequence as set forth in a sequence: NTGGTAGNNN GATAGGGNNN GCTGANNNGA NNNGTGGN (SEQ ID NO: 46) competes with aptamer having a sequence: CGACTGGTAG GCAGATAGGG GAAGCTGATT CGATGCGTGG GTCG (SEQ ID NO: 45) for serotonin binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a serotonin-binding aptamer includes a core sequence as set forth in a sequence: NTGGTAGNNN GATAGGGNNN GCTGANNNGA NNNGTGGN (SEQ ID NO: 46) and further includes at least one operative sequence. In certain non-limiting embodiments, a serotonin-binding aptamer includes a core sequence as set forth in a sequence: NTGGTAGNNN GATAGGGNNN GCTGANNNGA NNNGTGGN (SEQ ID NO: 46) and further includes at least one operative sequence, the operative sequence complementary to a sequence included in a sensor oligonucleotide. In certain non-limiting embodiments, a serotonin-binding aptamer includes a core sequence as set forth in a sequence: NTGGTAGNNN GATAGGGNNN GCTGANNNGA NNNGTGGN (SEQ ID NO: 46) and at least one operative sequence on either side (flanking) the core sequence.

In certain non-limiting embodiments, a serotonin-binding aptamer includes a core sequence as set forth in a sequence: NTGGTAGNNN GATAGGGNNN GCTGANNNGA NNNGTGGN (SEQ ID NO: 46) and at least one operative sequence on either side (flanking) the core sequence, where two of the operative sequences contain mutually complementary portions and can form a duplex.

For example, but not by way of limitation, a serotonin-binding aptamer can include the sequence: CTC TCG GGA CGA CTG GTA GGC AAC AGG GGA AGG GAG TTC TGC GTA CGT GGG TCG TCC C (SEQ ID NO: 47) or related sequence: CGACTGGTAG GCAACAGGGG AAGGGAGTTC TGCGTACGTG GGTCG (SEQ ID NO: 48). In certain non-limiting embodiments, a serotonin-binding aptamer includes a core sequence as set forth in a sequence: NTGGNAGGNA ACAGGGGNNG GGAGNNCTNC GTNCGTGGN (SEQ ID NO: 49). In certain non-limiting embodiments, a serotonin-binding aptamer includes a core sequence as set forth in a sequence: NTGGNAGGNA ACAGGGGNNG GGAGNNCTNC GTNCGTGGN (SEQ ID NO: 49) has a binding affinity for serotonin that is at least about 50 percent or at least about 75 percent the binding affinity of the aptamer having a sequence: CGACTGGTAG GCAACAGGGG AAGGGAGTTC TGCGTACGTG GGTCG (SEQ ID NO: 48). In certain non-limiting embodiments, a serotonin-binding aptamer includes a core sequence as set forth in a sequence: NTGGNAGGNA ACAGGGGNNG GGAGNNCTNC GTNCGTGGN (SEQ ID NO: 49) competes with aptamer having a sequence: CGACTGGTAG GCAACAGGGG AAGGGAGTTC TGCGTACGTG GGTCG (SEQ ID NO: 48) for serotonin binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a serotonin-binding aptamer includes a core sequence as set forth in a sequence: NTGGNAGGNA ACAGGGGNNG GGAGNNCTNC GTNCGTGGN (SEQ ID NO: 49) and further includes at least one operative sequence. In certain non-limiting embodiments, a serotonin-binding aptamer includes a core sequence as set forth in a sequence: NTGGNAGGNA ACAGGGGNNG GGAGNNCTNC GTNCGTGGN (SEQ ID NO: 49) and further includes at least one operative sequence, the operative sequence complementary to a sequence included in a sensor oligonucleotide. In certain non-limiting embodiments, a serotonin-binding aptamer includes a core sequence as set forth in a sequence: NTGGNAGGNA ACAGGGGNNG GGAG- NNCTNC GTNCGTGGN (SEQ ID NO: 49) and at least one operative sequence on either side (flanking) the core sequence. In certain non-limiting embodiments, a serotonin-binding aptamer includes a core sequence as set forth in a sequence: NTGGNAGGNA ACAGGGGNNG GGAG-NNCTNC GTNCGTGGN (SEQ ID NO: 49) and at least one operative sequence on either side (flanking) the core sequence, where two of the operative sequences contain mutually complementary portions and can form a duplex.

For example, but not by way of limitation, a serotonin-binding aptamer can include the sequence: CTC TCG GGA CGA CAG GGG CAT ATA TAG TCT AGG GTT TGG TGT GGG TAG TGT CGT CCC (SEQ ID NO: 50) or related sequence: CGACAGGGGC ATATATAGTC TAGGGTTTGG TGTGGGTAGT GTCG (SEQ ID NO: 51). In certain non-limiting embodiments, a serotonin-binding aptamer includes a core sequence as set forth in a sequence: NAGGGGCATA TATAGTCTAG GGTTTGGTGT GGGTAGTN (SEQ ID NO: 52). In certain non-limiting embodiments, a serotonin-binding aptamer includes a core sequence as set forth in a sequence: NAGGGGCATA TATAGTCTAG GGTTTGGTGT GGGTAGTN (SEQ ID NO: 52) has a binding affinity for serotonin that is at least about 50 percent or at least about 75 percent the binding affinity of the aptamer having a sequence: CGACAGGGGC ATATATAGTC TAGGGTTTGG TGTGGGTAGT GTCG (SEQ ID NO: 51). In certain non-limiting embodiments, a serotonin-binding aptamer includes a core sequence as set forth in a sequence: NAGGGGCATA TATAGTCTAG GGTTTGGTGT GGGTAGTN (SEQ ID NO: 52) competes with aptamer having a sequence: CGACAGGGGC ATATATAGTC TAGGGTTTGG TGTGGGTAGT GTCG (SEQ ID NO: 51) for serotonin binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a serotonin-binding aptamer includes a core sequence as set forth in a sequence: NAGGGGCATA TATAGTCTAG GGTTTGGTGT GGGTAGTN (SEQ ID NO: 52) and further includes at least one operative sequence. In certain non-limiting embodiments, a serotonin-binding aptamer includes a core sequence as set forth in a sequence: NAGGGGCATA TATAGTCTAG GGTTTGGTGT GGGTAGTN (SEQ ID NO: 52) and further includes at least one operative sequence, the operative sequence complementary to a sequence included in a sensor oligonucleotide. In certain non-limiting embodiments, a serotonin-binding aptamer includes a core sequence as set forth in a sequence: NAGGGGCATA TATAGTCTAG GGTTTGGTGT GGGTAGTN (SEQ ID NO: 52) and at least one operative sequence on either side (flanking) the core sequence. In certain non-limiting embodiments, a serotonin-binding aptamer includes a core sequence as set forth in a sequence: NAGGGGCATA TATAGTCTAG GGTTTGGTGT GGGTAGTN (SEQ ID NO: 52) and at least one operative sequence on either side (flanking) the core sequence, where two of the operative sequences contain mutually complementary portions and can form a duplex.

For example, but not by way of limitation, a serotonin-binding aptamer can include the sequence: CTC TCG GGA CGA CTG GTA GGC AGC AGG GGA AGT AGG CGT GTC CTC GTG GGT CGT CCC (SEQ ID NO: 53) or related sequence: CGACTGGTAG GCAGCAGGGG AAGTAGGCGT GTCCTCGTGG GTCG (SEQ ID NO: 54). In certain non-limiting embodiments, a serotonin-binding aptamer includes a core sequence as set forth in a sequence: NTGGTAGGCA GCAGGGGAAG TAGGCGTGTC CTCGTGGN (SEQ ID NO: 55). In certain non-limiting embodiments, a serotonin-binding aptamer includes a core sequence as set forth in a sequence: NTGGTAGGCA GCAGGGGAAG TAGGCGTGTC CTCGTGGN (SEQ ID NO: 55) has a binding affinity for serotonin that is at least about 50 percent or at least about 75 percent the binding affinity of the aptamer having a sequence: CGACTGGTAG GCAGCAGGGG AAGTAGGCGT GTCCTCGTGG GTCG (SEQ ID NO: 54). In certain non-limiting embodiments, a serotonin-binding aptamer includes a core sequence as set forth in a sequence: NTGGTAGGCA GCAGGGGAAG TAGGCGTGTC CTCGTGGN (SEQ ID NO: 55) competes with aptamer having a sequence: CGACTGGTAG GCAGCAGGGG AAGTAGGCGT GTCCTCGTGG GTCG (SEQ ID NO: 54) for serotonin binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a serotonin-binding aptamer includes a core sequence as set forth in a sequence: NTGGTAGGCA GCAGGGGAAG TAGGCGTGTC CTCGTGGN (SEQ ID NO: 55) and further includes at least one operative sequence. In certain non-limiting embodiments, a serotonin-binding aptamer includes a core sequence as set forth in a sequence: NTGGTAGGCA GCAGGGGAAG TAGGCGTGTC CTCGTGGN (SEQ ID NO: 55) and further includes at least one operative sequence, the operative sequence complementary to a sequence included in a sensor oligonucleotide. In certain non-limiting embodiments, a serotonin-binding aptamer includes a core sequence as set forth in a sequence: NTGGTAGGCA GCAGGGGAAG TAGGCGTGTC CTCGTGGN (SEQ ID NO: 55) and at least one operative sequence on either side (flanking) the core sequence. In certain non-limiting embodiments, a serotonin-binding aptamer includes a core sequence as set forth in a sequence: NTGGTAGGCA GCAGGGGAAG TAGGCGTGTC CTCGTGGN (SEQ ID NO: 55) and at least one operative sequence on either side (flanking) the core sequence, where two of the operative sequences contain mutually complementary portions and can form a duplex.

For example, but not by way of limitation, a serotonin-binding aptamer can include the sequence: CTC TCG GGA CGA CCA GTA GGG GAT CCA CAG TGA GGG GTT TGT ATG GGT GGT CGT CCC (SEQ ID NO: 56) or related sequence: GACCAGTAGG GGATCCACAG TGAGGGGTTT GTATGGGTGG TC (SEQ ID NO: 57). In certain non-limiting embodiments, a serotonin-binding aptamer includes a core sequence as set forth in a sequence: NAGTAGGGGA NNNNCAGTGA GGGGTTTGTA NNNNTN (SEQ ID NO: 58). In certain non-limiting embodiments, a serotonin-binding aptamer includes a core sequence as set forth in a sequence: NAGTAGGGGA NNNNCAGTGA GGGGTTTGTA NNNNTN (SEQ ID NO: 58) has a binding affinity for serotonin that is at least about 50 percent or at least about 75 percent the binding affinity of the aptamer having a sequence: GACCAGTAGG GGATC-CACAG TGAGGGGTTT GTATGGGTGG TC (SEQ ID NO: 57). In certain non-limiting embodiments, a serotonin-binding aptamer includes a core sequence as set forth in a sequence: NAGTAGGGGA NNNNCAGTGA GGGGTTTGTA NNNNTN (SEQ ID NO: 58) competes with aptamer having a sequence: GACCAGTAGG GGATC-CACAG TGAGGGGTTT GTATGGGTGG TC (SEQ ID NO: 57) for serotonin binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a serotonin-binding aptamer includes a core sequence as set forth in sequence: NAGTAGGGGA NNNNCAGTGA GGGGTTTGTA NNNNTN (SEQ ID NO: 58) and further includes at least one operative sequence. In certain non-limiting embodiments, a serotonin-binding aptamer includes a core sequence as set forth in a sequence: NAGTAGGGGA NNNNCAGTGA GGGGTTTGTA NNNNTN (SEQ ID NO: 58) and further includes at least one operative sequence, the operative sequence complementary to a sequence included in a sensor oligonucleotide. In certain non-limiting embodiments, a serotonin-binding aptamer includes a core sequence as set forth in a sequence: NAGTAGGGGA NNNNCAGTGA GGGGTTTGTA NNNNTN (SEQ ID NO: 58) and at least one operative sequence on either side (flanking) the core sequence. In certain non-limiting embodiments, a serotonin-binding aptamer includes a core sequence as set forth in a sequence: NAGTAGGGGA NNNNCAGTGA GGGGTTTGTA NNNNTN (SEQ ID NO: 58) and at least one operative sequence on either side (flanking) the core sequence, where two of the operative sequences contain mutually complementary portions and can form a duplex.

For example, but not by way of limitation, a serotonin-binding aptamer can include the sequence: CTC TCG GGA CGA CGG AGG TGG TGT CTT GGA CAG TGG TAT TCG CAG TTG CGT CGT CCC (SEQ ID NO: 59) or related sequence: CGACGGAGGT GGTGTCTTGG ACAGTGGTAT TCGCAGTTGC GTCG (SEQ ID NO: 60). In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61). In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61) has a binding affinity for serotonin that is at least about 50 percent or at least about 75 percent the binding affinity of the aptamer having a sequence: CGACGGAGGT GGTGTCTTGG ACAGTGGTAT TCGCAGTTGC GTCG (SEQ ID NO: 60). In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61) competes with aptamer having a sequence: CGACGGAGGT GGTGTCTTGG ACAGTGGTAT TCGCAGTTGC GTCG (SEQ ID NO: 60) for serotonin binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61) and further includes at least one operative sequence. In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61) and further includes at least one operative sequence, the operative sequence complementary to a sequence included in a sensor oligonucleotide. In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61) and at least one operative sequence on either side (flanking) the core sequence. In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61) and at least one operative sequence on either side (flanking) the core sequence, where two of the operative sequences contain mutually complementary portions and can form a duplex.

For example, but not by way of limitation, a serotonin-binding aptamer can include the sequence: CTC TCG GGA CGA CAG AGA CGG GGT GCT TAC TTG GTT CAG GGG AGT CGA CGT CGT CCC (SEQ ID NO: 62) or related sequence: ACGACAGAGA CGGGGTGCTT ACTTGGTTCA GGGGAGTCGA CGTCGT (SEQ ID NO: 63). In certain non-limiting embodiments, a serotonin-binding aptamer includes a core sequence as set forth in a sequence: NNAGANNNGG GGTGCTTACT TGGTTCAGGG GANNNGACNN (SEQ ID NO: 64). In certain non-limiting embodiments, a serotonin-binding aptamer includes a core sequence as set forth in a sequence: NNAGANNNGG GGTGCTTACT TGGTTCAGGG GANNNGACNN (SEQ ID NO: 64) has a binding affinity for serotonin that is at least about 50 percent or at least about 75 percent the binding affinity of the aptamer having a sequence: ACGACAGAGA CGGGGTGCTT ACTTGGTTCA GGGGAGTCGA CGTCGT (SEQ ID NO: 63). In certain non-limiting embodiments, a serotonin-binding aptamer includes a core sequence as set forth in a sequence: NNAGANNNGG GGTGCTTACT TGGTTCAGGG GANNNGACNN (SEQ ID NO: 64) competes with aptamer having a sequence: ACGACAGAGA CGGGGTGCTT ACTTGGTTCA GGGGAGTCGA CGTCGT (SEQ ID NO: 63) for serotonin binding. In non-limiting embodiments, the aptamer has a length of between about 30 and about 100 nucleotides, or between about 30 and 80 nucleotides, or between about 30 and 70 nucleotides, or between about 30 and 60 nucleotides. In certain non-limiting embodiments, a serotonin-binding aptamer includes a core sequence as set forth in a sequence: NNAGANNNGG GGTGCTTACT TGGTTCAGGG GANNNGACNN (SEQ ID NO: 64) and further includes at least one operative sequence. In certain non-limiting embodiments, a serotonin-binding aptamer includes a core sequence as set forth in a sequence: NNAGANNNGG GGTGCTTACT TGGTTCAGGG GANNNGACNN (SEQ ID NO: 64) and further includes at least one operative sequence, the operative sequence complementary to a sequence included in a sensor oligonucleotide. In certain non-limiting embodiments, a serotonin-binding aptamer includes a core sequence as set forth in a sequence: NNAGANNNGG GGTGCTTACT TGGTTCAGGG GANNNGACNN (SEQ ID NO: 64) and at least one operative sequence on either side (flanking) the core sequence. In certain non-limiting embodiments, a serotonin-binding aptamer includes a core sequence as set forth in a sequence: NGGAGGTGGN NNNNNNNNNN GTGGTATTCG CAGTTGCN (SEQ ID NO: 61) and at least one operative sequence on either side (flanking) the core sequence, where two of the operative sequences contain mutually complementary portions and can form a duplex.

In certain non-limiting embodiments, isolated serotonin-binding aptamers include the nucleotide sequence of CTCTCGGGAC GACTGGTAGG CAGATAGGGG AAGCTGATTC GATGCGTGGG TCGTCCC (SEQ ID NO: 44), CGACTGGTAG GCAGATAGGG GAAGCT-GATT CGATGCGTGG GTCG (SEQ ID NO: 45), CTCTCGGGAC GACTGGTAGG CAACAGGGGA AGG-GAGTTCT GCGTACGTGG GTCGTCCC (SEQ ID NO: 47), CGACTGGTAG GCAACAGGGG AAGGGAGTTC TGCGTACGTG GGTCG (SEQ ID NO: 48), CTCTCGGGAC GACAGGGGCA TATATAGTCT AGGGTTTGGT GTGGGTAGTG TCGTCCC (SEQ ID NO: 50), CGACAGGGGC ATATATAGTC TAGGGTTTGG TGTGGGTAGT GTCG (SEQ ID NO: 51), CTCTCGGGAC GACTGGTAGG CAGCAGGGGA AGTAGGCGTG TCCTCGTGGG TCGTCCC (SEQ ID NO: 53), CGACTGGTAG GCAGCAGGGG AAGTAGGCGT GTCCTCGTGG GTCG (SEQ ID NO: 54), CTCTCGGGAC GACCAGTAGG GGATCCACAG TGAGGGGTTT GTATGGGTGG TCGTCCC (SEQ ID NO: 56), GACCAGTAGG GGATCCACAG TGAGGGGTTT GTATGGGTGG TC (SEQ ID NO: 57), CTCTCGGGAC GACGGAGGTG GTGTCTTGGA CAGTGGTATT CGCAGTTGCG TCGTCCC (SEQ ID NO: 59), CGACG-GAGGT GGTGTCTTGG ACAGTGGTAT TCGCAGTTGC GTCG (SEQ ID NO: 60), CTCTCGGGAC GACAGAGACG GGGTGCTTAC TTGGTTCAGG GGAGTCGACG TCGTCCC (SEQ ID NO: 62), ACGACAGAGA CGGGGTGCTT ACTTGGTTCA GGG-GAGTCGA CGTCGT (SEQ ID NO: 63), or variants of these sequences having at least about 80 percent, or at least about 85 percent, or at least about 90 percent, or at least about 95 percent, or at least about 98 percent homology to the original sequence, for example obtained by substitutions, deletions, and insertions of Watson-Crick base pairs or by mutations at non-conserved positions. Percent homology can be determined using standard software such as BLAST or FASTA. In certain non-limiting embodiments, isolated serotonin-binding aptamers include the nucleotide sequence of CTCTCGGGAC GACTGGTAGG CAGATAGGGG AAGCTGATTC GATGCGTGGG TCGTCCC (SEQ ID NO: 44), CGACTGGTAG GCAGATAGGG GAAGCT-GATT CGATGCGTGG GTCG (SEQ ID NO: 45), CTCTCGGGAC GACTGGTAGG CAACAGGGGA AGG-GAGTTCT GCGTACGTGG GTCGTCCC (SEQ ID NO: 47), CGACTGGTAG GCAACAGGGG AAGGGAGTTC TGCGTACGTG GGTCG (SEQ ID NO: 48), CTCTCGGGAC GACAGGGGCA TATATAGTCT AGGGTTTGGT GTGGGTAGTG TCGTCCC (SEQ ID NO: 50), CGACAGGGGC ATATATAGTC TAGGGTTTGG TGTGGGTAGT GTCG (SEQ ID NO: 51), CTCTCGGGAC GACTGGTAGG CAGCAGGGGA AGTAGGCGTG TCCTCGTGGG TCGTCCC (SEQ ID NO: 53), CGACTGGTAG GCAGCAGGGG AAGTAGGCGT GTCCTCGTGG GTCG (SEQ ID NO: 54), CTCTCGGGAC GACCAGTAGG GGATCCACAG TGAGGGGTTT GTATGGGTGG TCGTCCC (SEQ ID NO: 56), GACCAGTAGG GGATCCACAG TGAGGGGTTT GTATGGGTGG TC (SEQ ID NO: 57), CTCTCGGGAC GACGGAGGTG GTGTCTTGGA CAGTGGTATT CGCAGTTGCG TCGTCCC (SEQ ID NO: 59), CGACG-GAGGT GGTGTCTTGG ACAGTGGTAT TCGCAGTTGC GTCG (SEQ ID NO: 60), CTCTCGGGAC GACAGAGACG GGGTGCTTAC TTGGTTCAGG GGAGTCGACG TCGTCCC (SEQ ID NO: 62), or ACGACAGAGA CGGGGTGCTT ACTTGGTTCA GGG-GAGTCGA CGTCGT (SEQ ID NO: 63). The aptamers can bind to serotonin and in their structure-switching formats they can respond by an increase in fluorescence, or by changes in a FET response, or by other spectroscopic signal changes (e.g., circular dichroism spectral changes, Raman spectral changes, or surface-enhanced Raman spectral changes).

Creatinine-Binding Aptamers

In certain non-limiting embodiments, the aptamer binds to creatinine in an aqueous solution at room temperature or 25° C. with a dissociation constant of less than $10^{-2}$ M and binds selectively with creatinine versus creatine or urea.

In certain non-limiting embodiments, a creatinine-binding aptamer includes the sequences GGTGGCCT and AGGGGTG or a variant of any of these sequences that differs in one or two bases by substitution, deletion, insertion or extension, where the aptamer binds to creatinine in an aqueous solution at room temperature or 25° C. with a dissociation constant of less than $10^2$ M and binds to creatinine selectively versus creatine or urea. In certain non-limiting embodiments, a creatinine-binding aptamer includes the sequences GGTGGCCT and AGGGGTG or a variant thereof and further includes at least one operative sequence. In certain non-limiting embodiments, a creatinine-binding aptamer includes the sequences GGTGGCCT and AGGGGTG or a variant thereof, and further includes at least one operative sequence, the operative sequence complementary to a sequence included in a sensor oligonucleotide. In certain non-limiting embodiments, a creatinine-binding aptamer includes the sequences GGTGGCCT and AGGGGTG, or a variant thereof, and at least one operative sequence on either side (flanking) these two sequences. In certain non-limiting embodiments, a creatinine-binding aptamer includes the sequences GGTGGCCT and AGGGGTG or a variant thereof, and at least one operative sequence on either side (flanking) these two sequences, where two of the operative sequences contain mutually complementary portions and can form a duplex.

For example, but not by way of limitation, a creatinine-binding aptamer can include the sequence: GA CGA CGGTGGCCTTAATAGATAGATGATATTCTTAT ATGTG TGAGGGGTG GT CGT C (SEQ ID NO: 65).

For example, but not by way of limitation, a creatinine-binding aptamer can include the sequence: GA CGA C GGTGGCCTATATTGGTATGTATGAA GAATAGAACT-ATTAGGGGGT GT C (SEQ ID NO: 66).

For example, but not by way of limitation, a creatinine-binding aptamer can include the sequence: CGA C GGTGGCCTATTAAATAGCTTTAGTT TAAGAAAAGTAATAGGGGGT GT CG (SEQ ID NO: 67).

For example, but not by way of limitation, a creatinine-binding aptamer can include the sequence: CTC TCG GGA CGA C GGTGGCCTATTAAGTAGCTTTA GTT-CAAGAAAAGTAATAGGGGGT GT CGT CCC (SEQ ID NO: 68).

In certain non-limiting embodiments, isolated creatinine-binding aptamers include the nucleotide sequence of GACGACGGTG GCCTTAATAG ATAGATGATA TTCT-TATATG TGTGAGGGGT GGTCGTC (SEQ ID NO: 65), GACGGTGGCC TATATTGGTA TGTATGAAGA ATAGAACTAT TAGGGGGTGT C (SEQ ID NO: 69), CGACGGTGGC CTATTAAATA GCTTTAGTTT AAGAAAAGTA ATAGGGGGTG TCG (SEQ ID NO: 67), CGACGGTGGC CTATTAAGTA GCTTTAGTTC AAGAAAAGTA ATAGGGGGTG TCG (SEQ ID NO: 70) or variants of these sequences having at least about 80 percent, or at least about 85 percent, or at least about 90 percent, or at least about 95 percent, or at least about 98 percent homology to the original sequence, for example obtained by substitutions, deletions, and insertions of Watson-Crick base pairs or by mutations at non-conserved positions. Percent homology can be determined using standard software such as BLAST or FASTA. In certain non-limiting embodiments, isolated creatinine-binding aptamers include the nucleotide sequence of GACGACGGTG GCCT-TAATAG ATAGATGATA TTCTTATATG TGTGAGGGGT GGTCGTC (SEQ ID NO: 65), GACGGTGGCC TATAT-TGGTA TGTATGAAGA ATAGAACTAT TAGGGGGTGT C (SEQ ID NO: 69), CGACGGTGGC CTATTAAATA GCTTTAGTTT AAGAAAAGTA ATAGGGGGTG TCG (SEQ ID NO: 67), OR CGACGGTGGC CTATTAAGTA GCTTTAGTTC AAGAAAAGTA ATAGGGGGTG TCG (SEQ ID NO: 70). The aptamers can bind to creatinine and in their structure-switching formats they can respond by an increase in fluorescence, or by changes in a FET response, or by other spectroscopic signal changes (e.g., circular dichroism spectral changes, Raman spectral changes, or surface-enhanced Raman spectral changes).

The disclosed subject matter provides for a field-effect-transistor with an attached stem-loop aptamer for sensing charged or electroneutral targets, including serotonin, dopamine, glucose, sphingosine-1-phosphate, and phenylalanine. The stem-loop aptamers can have target-induced conformational changes of negatively charged aptamer phosphodiester backbones in close proximity to semiconductor channels to gate conductance, resulting in sensitive target detection. The disclosed FET with the stem-loop aptamers can allow detection of the target analytes with few or no charges within or near the Debye length under high ionic strength conditions, (i.e., small Debye length, for example, less than 1 nanometer). In some embodiments, the disclosed FET is a quasi-two-dimensional FET.

In certain embodiments, the disclosed subject matter provides methods for detecting or measuring the presence or amount of a target molecule in a sample. An example method can include contacting at least a portion of a sample with effective amounts of an aptamer on a surface of a field-effect transistor and detecting a conductance change of the field-effect transistor. The term "effective amount", as used herein, refers to that portion of an aptamer needed to detect a target molecule and to induce a conductance change on the surface of the field-effect transistor. The term can encompass an amount that improves overall target detection, or reduces or avoids unwanted effects.

The stem region of the aptamer can adopt a second conformation when the capture region of the aptamer binds to the target molecule. In some embodiments, the aptamer can include a stem and at least one loop. The at least one loop can include a capture region and the stem can include a stem region. The aptamer can selectively detect the target molecule and allow a direct measurement of the target molecule without dilution of the sample. In non-limiting embodiments, the aptamer can include more than one loop which can form a target binding pocket.

In certain embodiments, the method for detecting or measuring the presence or amount of a target molecule in a sample can further include performing a solution-phase selection of the aptamer. In some embodiments, the method can also include immobilizing the aptamer on the surface of a field-effect transistor. In non-limiting embodiments, the method can include adjusting the sensitivity of an aptamer by modifying a length of the stem region.

In certain embodiments, the disclosed subject matter provides exemplary DNA aptamers for phenylalanine (Phe). The Phe aptamers can be fluorescent sensors and can be incorporated with field-effect transistor sensors. For example, the direct-binding phenylalanine aptamers can be integrated with thin-film metal-oxide field-effect transistors (FETs). The aptamer-field-effect transistor sensors can detect phenylalanine over a wide range of concentrations yet differentiate small changes in phenylalanine levels expected in patients. For example, the disclosed sensors can differentiate serum phenylalanine levels and can be specific for phenylalanine. The disclosed sensor can selectively detect phenylalanine in the presence of structurally related naturally occurring amino acids and enzyme inhibitors. In non-limiting embodiments, the disclosed sensor can be used to determine and detect any symptoms caused by excess or inadequate phenylalanine. For example, the disclosed sensor can be used for detecting phenylketonuria and hyperphenylalanemias. Aptamers with improved selectivity can be integrated into field-effect transistors and can allow rapid, electronic, and label-free phenylalanine sensing.

Example 1—Aptamer-Field-Effect Transistors Overcome Debye Length Limitations to Enable Small-Molecule Sensing This example illustrates the use of aptamer-field-effect transistors for sensing serotonin, dopamine, glucose, and sphingosine-1-phosphate using target specific stem-loop aptamers.

Materials and Method

All chemicals were purchased from Sigma-Aldrich Co. (St. Louis, MO), unless otherwise noted below. Oligonucleotides were obtained from Integrated DNA Technologies (Coralville, IA). The SYLGARD 184 for fabricating polydimethylsiloxane (PDMS) wells was from Dow Corning Corporation (Midland, MI). Water was deionized before use (18.2 MΩ) via a Milli-Q system (Millipore, Billerica, MA). Other sources are available and can be used for such components.

Aptamer Selection

Solution-phase selection of aptamers was carried out using the following procedures, with modifications in oligonucleotides and PCR conditions as follows. (1) Random ($N_{30}$) library 5'-GGA GGC TCT CGG GAC GAC-($N_{30}$)-GTC GTC CCG ATG CTG CAA TCG TAA-3' (SEQ ID NO: 71), (2) Random ($N_{36}$) library 5'-GGA GGC TCT CGG GAC GAC-($N_{36}$)-GTC GTC CCG CCT TTA GGA TTT ACA G-3' (SEQ ID NO: 72), (3) forward-primer: 5'-GGA GGC TCT CGG GAC GAC-3' (SEQ ID NO: 73), (4) reverse-primer for $N_{30}$ TTA CGA TTG CAG CAT CGG GAC G (SEQ ID NO: 74), (5) biotinylated reverse-primer for $N_{30}$ 5'-biotin-TTA CGA TTG CAG CAT CGG GAC G-3' (SEQ ID NO: 74), (6) reverse-primer for $N_{36}$ 5'-CTG TAA ATC CTA AAG GCG GGA CGA C-3' (SEQ ID NO: 75), (7) biotinylated reverse-primer for $N_{36}$ 5'-biotin-CTG TAA ATC CTA AAG GCG GGA CGA C-3' (SEQ ID NO: 75), and (5) biotinylated column-immobilizing capture strand 5'-GTC GTC CCG AGA GCC ATA-BioTEG-3' (SEQ ID NO: 76).

Standard desalted oligonucleotides were used for the libraries, primers, and complementary strands. Modified oligonucleotides, e.g., biotinylated, fluorophore-conjugated, were purified by reverse-phase HPLC. All oligonucleotides were dissolved in nuclease-free water and stored at −20° C. The PCR reactions were run with one cycle at 95° C. for 2 min, N cycles of [95° C., 15 s→60° C., 30 s→72° C., 45 s], and one cycle at 72° C. for 2 min. Specific selection/counter-selection conditions are described below (Tables 1 and 2).

TABLE 1

List of selection conditions for dopamine and serotonin aptamers.

| | Round | Target concentrations (no. of elutions) | Counter-target concentrations (no. of elutions) |
|---|---|---|---|
| Dopamine | 1-2 | 100 μM (3) | No counter-SELEX |
| SELEX with | 3-4 | 100 μM (3) | Serotonin 100 μM (8) |
| $N_{38}$ library | 5 | 100 μM (3) | No counter-SELEX |
| PBS + | 6 | 100 μM (3) | Serotonin 200 μM (8) |
| 2 mM $MgCl_2$ | 7 | 100 μM (3) | Serotonin 200 μM (16) |
| | 8 | 100 μM (3) | Tyrosine 100 μM (16) |
| | 9 | 100 μM (3) | Tyrosine 200 μM (16) |
| | 10 | 100 μM (3) | Tryptophan 200 μM (16) |
| | 11 | 50 μM (3) | L-DOPA 200 μM (8) |
| | 12 | 50 uM (3) | L-DOPA 200 μM (16) |
| | 13 | 20 μM (3) | No counter-SELEX |
| | 14-17 | 20 μM (3) | Serotonin 100 μM (16) |
| | 18 | 20 μM (3) | Serotonin 20 μM (20) |
| Serotonin | 1-4 | 100 μM (3) | No counter-SELEX |
| SELEX with | 5-6 | 100 μM (3) | Tryptophan 100 μM (8) |
| $N_{36}$ library | 7 | 100 μM (3) | Tryptophan 100 μM (16) |
| HEPES | 8-9 | 50 μM (3) | No counter-SELEX |
| | 10 | 50 μM (3) | Tryptophan 100 μM (8) |
| | 11-12 | 50 μM (3) | Tryptophan 100 μM (16) |
| | 13 | 25 μM (3) | No counter-SELEX |
| | 14 | 25 μM (3) | Proline 100 μM (8) |
| | 15 | 25 μM (3) | 5-HIAA 50 μM (16) |
| | 16-17 | 20 μM (3) | Melatonin 100 μM (16) |
| | 18 | 20 μM (3) | Melatonin 100 μM (10) 5-HIAA 100 μM (10) |
| | 19 | 10 μM (3) | Melatonin 200 μM (16) |
| | 20 | 5 μM (3) | No counter-SELEX |

The SELEX/counter-SELEX processes can be used to identify the dopamine and serotonin aptamers. Numbers of rounds of SELEX are determined empirically. Each elution was with 250 μL selection buffer.

TABLE 2

List of selection conditions for glucose and sphingosine-1-phosphate (S1P) aptamers.

| | SELEX/Counter-SELEX | | |
|---|---|---|---|
| Target | Round | Target concentrations (no. of elutions) | Counter-target concentrations (no. of elutions) |
| Glucose | 1-5 | 100 mM (3) | No counter-SELEX |
| SELEX with | 6-7 | 50 mM (3) | Fructose, 100 mM (8) |
| $N_{30}$ library | 8-9 | 25 mM (3) | Galactose, 100 mM (8) |
| HEPES | 10 | 25 mM (3) | Mixture of 100 mM fructose and 100 mM galactose (8) |
| | 11-13 | 25 mM (3) | No counter-SELEX |
| | 14 | 25 mM (3) | Fructose 100 mM (16) Galactose 100 mM (16) |
| | 15 | 25 mM (3) | No counter-SELEX |
| S1P | 1-2 | 50 μM S1P-50 μM CpRh (3) | No counter-SELEX |
| SELEX with | | | |
| $N_{36}$ library | 3 | 25 μM S1P-50 μM CpRh (3) | No counter-SELEX |
| HEPES | | | |
| | 4 | 25 μM S1P-50 μM CpRh (3) | CpRh, 50 μM (6) |
| | 5 | 25 μM SIP-50 μM CpRh (3) | CpRh, 100 μM (6) |
| | 6 | 25 μM SIP-50 μM CpRh (3) | No counter-SELEX |
| | 7-11 | 25 μM SIP-50 μM CpRh (3) | No counter-SELEX |
| | 12-14 | 25 μM SIP-50 μM CpRh (3) | CpRh, 100 μM (16) |

TABLE 2-continued

List of selection conditions for glucose and sphingosine-1-phosphate (S1P) aptamers.

| | SELEX/Counter-SELEX | | |
|---|---|---|---|
| Target | Round | Target concentrations (no. of elutions) | Counter-target concentrations (no. of elutions) |
| | 15-16 | 50 μM SIP-50 μM CpRh (3) | CpRh, 100 μM (16) |
| | 17-18 | 50 μM SIP-50 μM CpRh (3) | CpRh, 100 μM (24) |
| | 19-20 | 50 μM SIP-50 μM CpRh (3) | CpRh, 100 μM (16) |

Note:
The original intended target was S1P-pentamethylcylopentadienylrhodium(III) chloride (CpRh) complex to develop a better epitope for the target. After isolating and characterizing the S1P aptamer, this aptamer was determined to be selective for S1P and not the complex.

The SELEX/counter-SELEX processes can be used to identify the glucose and sphingosine-1I-phosphate (SIP) aptamers. Numbers of rounds of SELEX are determined empirically. Each elution was with 250 μL selection buffer. Aptamers for serotonin, glucose, and S1P were selected in HEPES buffer at pH 7.5 (Table 3). The full names of oligonucleotide modification codes are as follows: /i6-FAMK/: internal fluorescein modification, /36-TAMTSp/: 5-carboxytetramethylrhodamine modification at the 3'-end.

| | |
|---|---|
| Glucose FRET sensor | (5'→3') GACTGGTAGGCAGATAGGGGAAGCTGAT/ 16-FAMK/TCGATGCGTGGGTC/36-TAMTSp/ |
| Serotonin FRET sensor | (5'→3'): CGACCGTGTGTGTA/16-FAMK/ TTCTATACAGTGTCCATTGTCG/36-TAMTSp/ |

Table 3. Sequences of glucose and serotonin aptamers (SEQ ID NOS 77 and 78, respectively) modified for Forster resonance energy transfer (FRET).

After adjusting the pH, HEPES buffer was filtered under vacuum using 0.22 μm filters (EMD Millipore Corp., Billerica, MA). The dopamine aptamer was selected in phosphate-buffered saline (PBS) purchased from Corning Inc. (Corning, NY), pH 7.4, with 2 mM $MgCl_2$ added.

For SELEX, the length of the oligonucleotides in the initial library is an important parameter that influences the outcome. However, the choice of the random region length can be made in a relatively arbitrary fashion. Longer randomized regions support the formation of more complex structures and presumably, allow formation of more intricate tertiary interactions. However, they also tend to misfold and to aggregate, whereas shorter sequences are sufficient to yield simpler motifs. In addition, there is not necessarily a statistically significant difference after analyzing the correlation between library length and affinity. For practical reasons, many in vitro selections have been carried out with pools of up to ~$10^{16}$ nominal library oligonucleotide elements.

Figure 7:
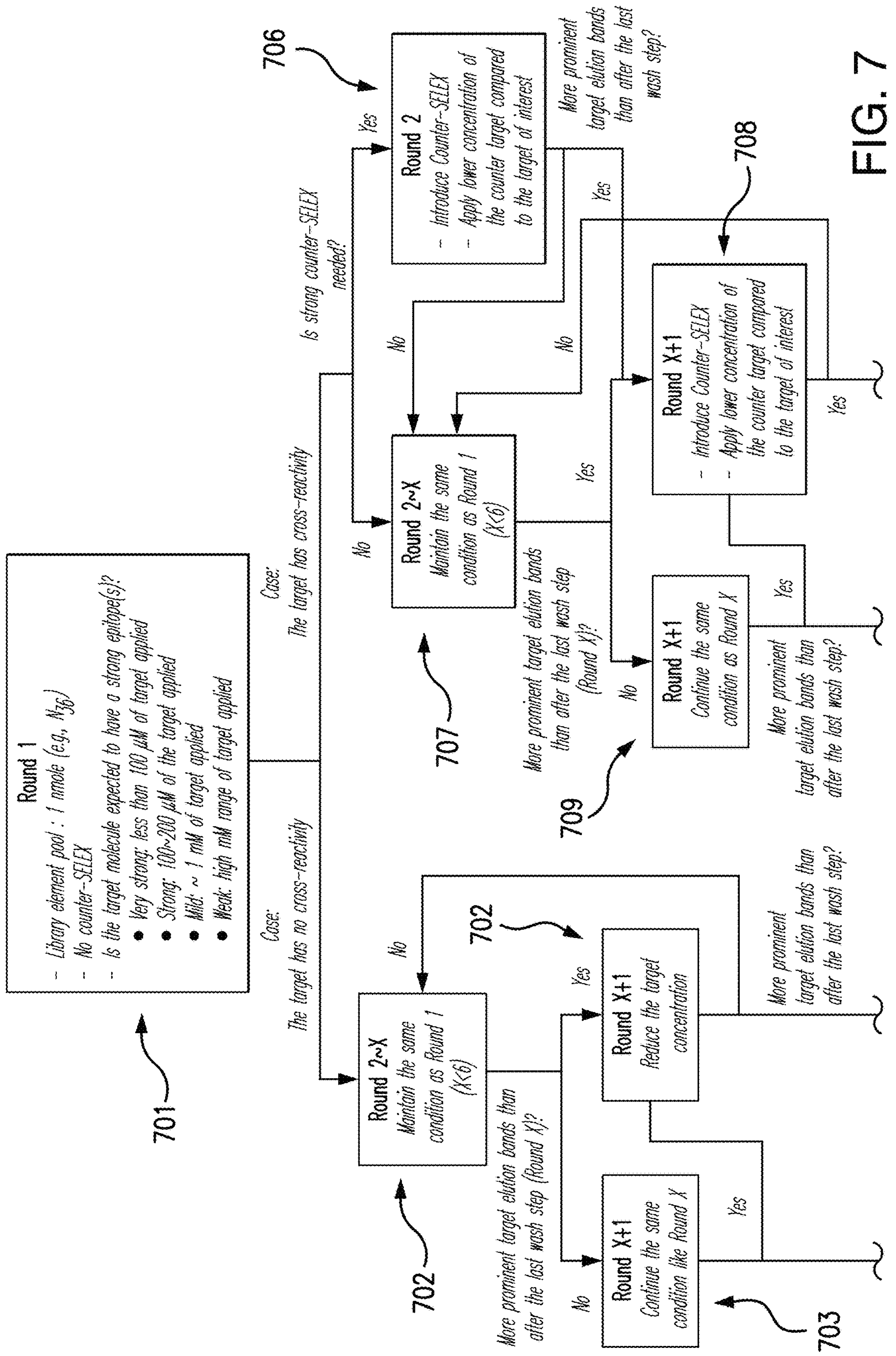
FIG. 7 provides an exemplary flow chart of SELEX and counter SELEX optimization strategies.
Figure 7:
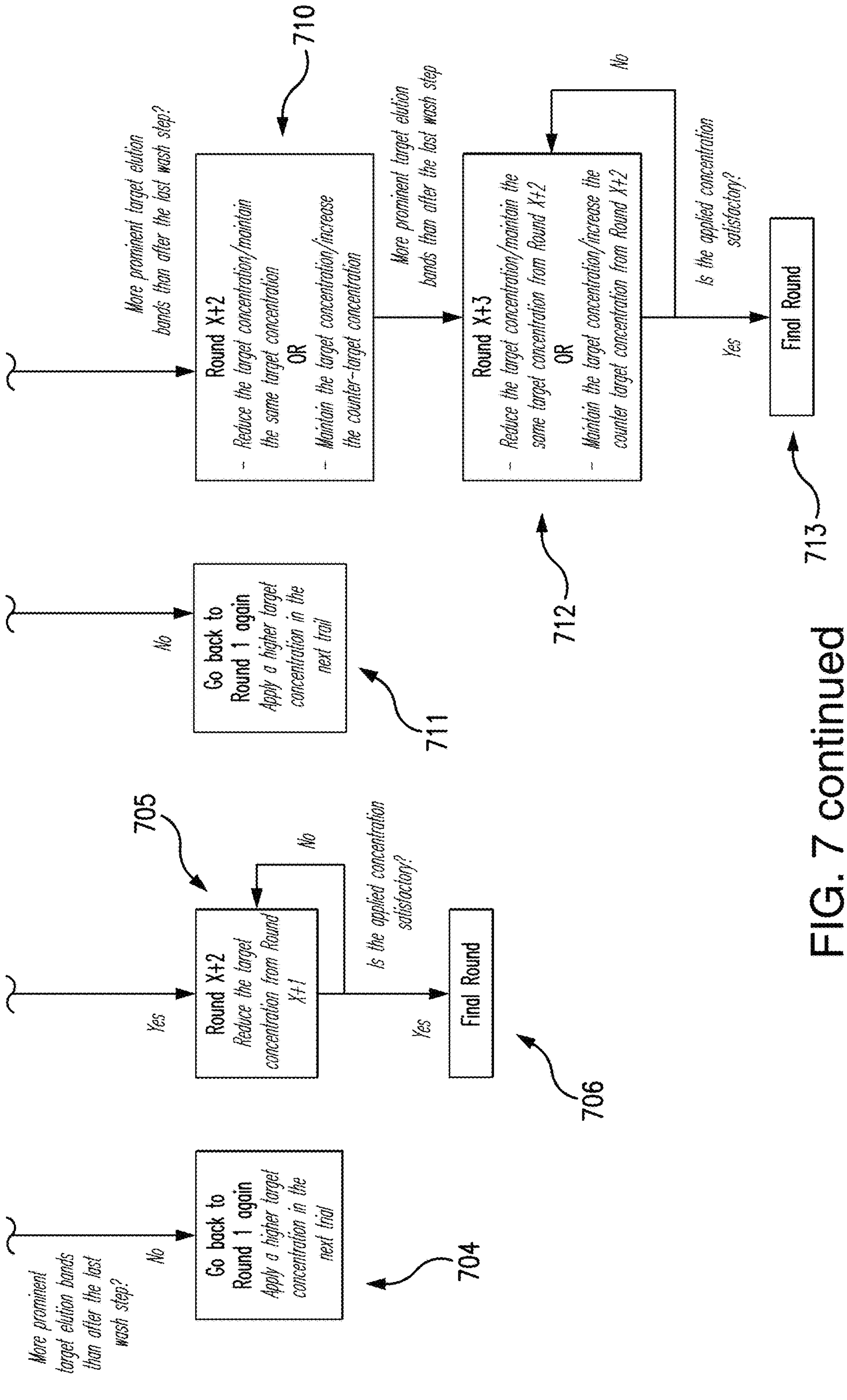

Counter-SELEX, which is an aspect of the selection process, can be largely trial and error. It is not straightforward to generalize counter-SELEX conditions against diverse targets due to the large numbers of variables involved in SELEX. An example decision making flowchart is shown in FIG. 7, which arises from empiricism.

Figure 8A:
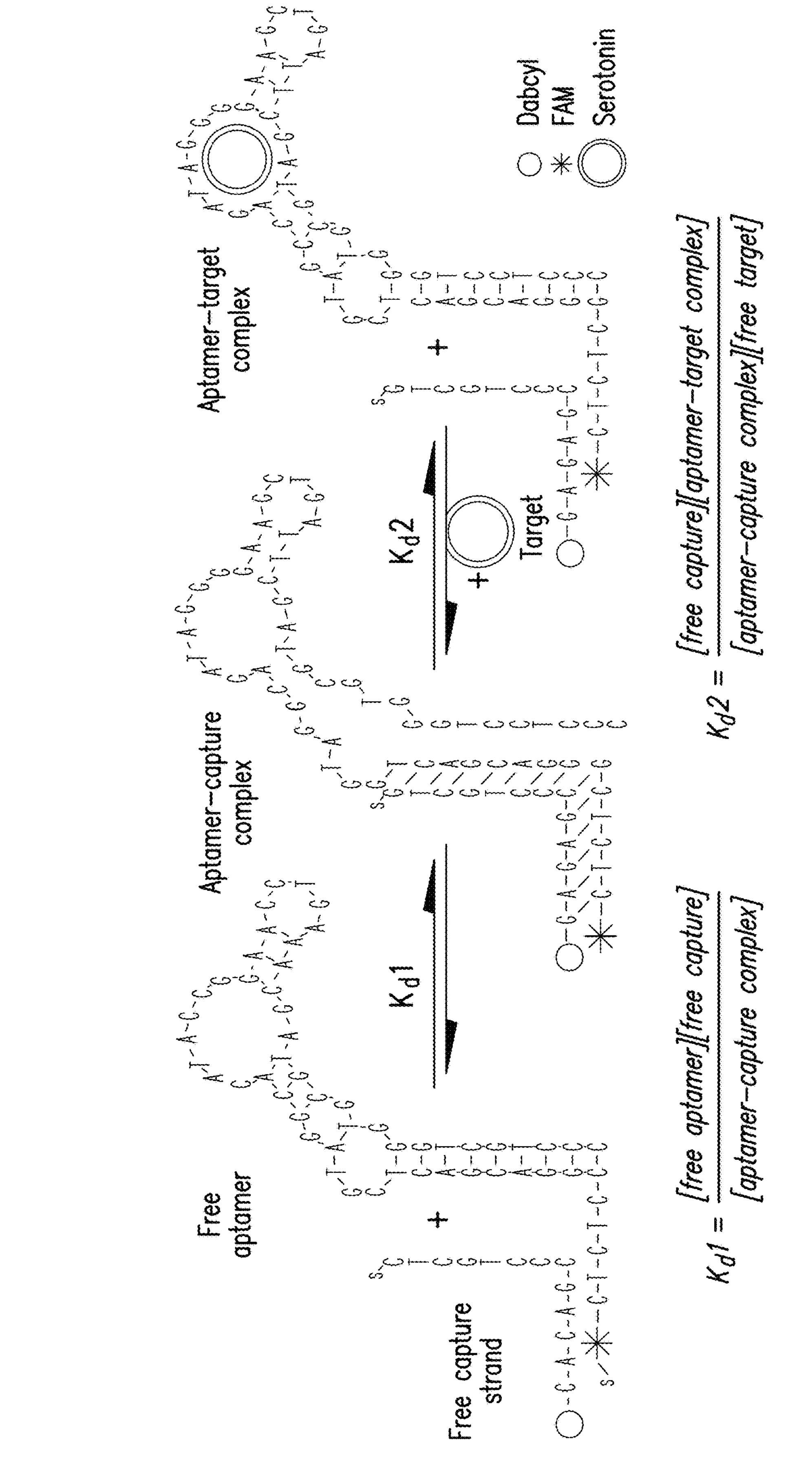
FIG. 8A provides schematic illustrations of an exemplary fluorescence assay mechanism. Figure discloses SEQ ID NOS 80, 44, 80, 44, 80, and 44, respectively, in order of appearance.

Aptamer candidates were modified with fluorescein at their 5' ends (FIG. 8A). Complementary strands were modified with dabcyl for quenching at their 3' ends. The concentrations of aptamers and complementary strands (Table 4) were determined empirically.

| Aptamer | Strand | Sequence (5'→3' | Concentration | Buffer |
|---|---|---|---|---|
| Dopamine | Sensor | /56-FAM/CTC TCG GGA CGA CGC CAG TTT GAA GGT TCG TTC GCA GGT GTG GAG TGA CGT CGT CCC | 50 nM | PBS |
| | Capture | CGT CGT CCC GAG AG/3Dab/ | 250 nM | |
| Serotonin | Sensor | /56-FAM/CTC TCG GGA CGA CTG GTA GGC AGA TAG GGG AAG CTG ATT CGA TGC GTG GGT CGT CCC | 50 nM | HEPES |
| | Capture | GTC GTC CCG AGA G/3Dab/ | 500 nM | |
| Glucose | Sensor | /56-FAM/CTC TCG GGA CGA CCG TGT GTG TTG CTC TGT AAC AGT GTC CAT TGT CGT CCC | 50 nM | HEPES |
| | Capture | GGT CGT CCC GAG AG/3Dab/ | 250 nM | |
| S1P | Sensor | /56-FAM/CTC TCG GGA CGA CGT GGT GTG GGA GAA AGA ATT TTC ATT GGG GTA GGG GGT CGT CCC | 50 nM | HEPES |
| | Capture | GTC GTC CCG AGA C/3Dab/ | 150 nM | |

Table 4. Sequences of aptamers and complementary (capture) strands (SEQ ID NOS 42, 79, 44, 80, 6, 81, 24, and 80, respectively, in order of appearance), and concentrations and buffers for fluorescence assay.

Aptamers were incubated with increasing concentrations of complementary (capture) strands. Apparent dissociation constants ($K_d$) can be calculated as the ratio of $K_d1/K_d2$. Fluorescence quenching can be used to determine $K_d1$. $K_d1$ can be calculated using equation 1.

$$K_d1=([\text{free aptamer}][\text{free capture}])/[\text{aptamer-capture complex}]) \quad (1)$$

Upon target binding, aptamers were folded inducing conformational changes that lead to dissociation from capture strands. Fluorescence in the presence of increasing concentrations of targets was used to determine $K_d2$. $K_d1$ can be calculated using equation 2.

$$K_d2=([\text{freecapture}][\text{aptamer-target complex}])/([\text{aptamer-capture complex}][\text{free target}]) \quad (2)$$

Figure 8B:
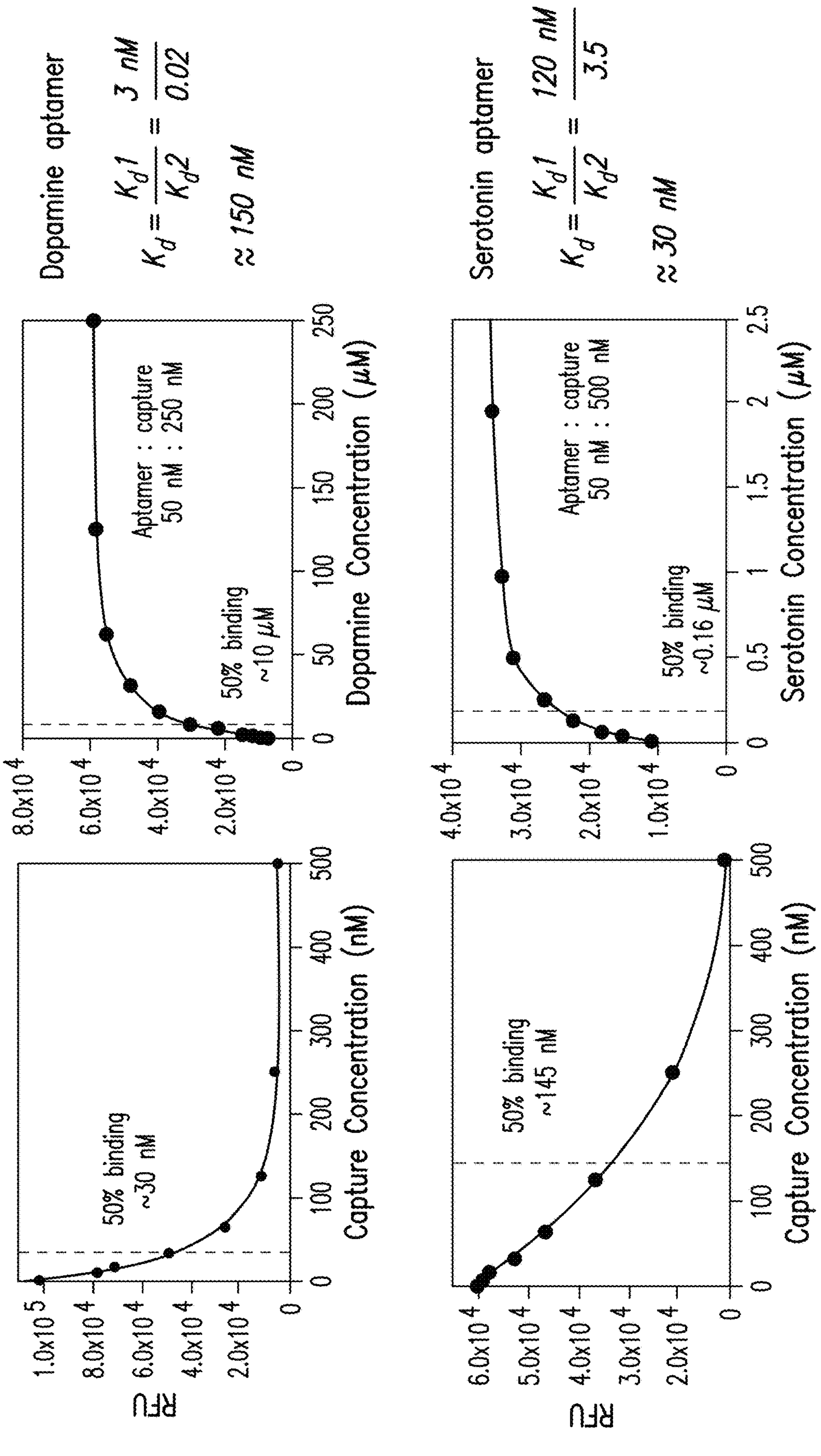
FIG. 8B provides fluorescence curves and apparent dissociation constants ($K_d$) for dopamine, serotonin, glucose, and S1P aptamers.
Figure 8B:
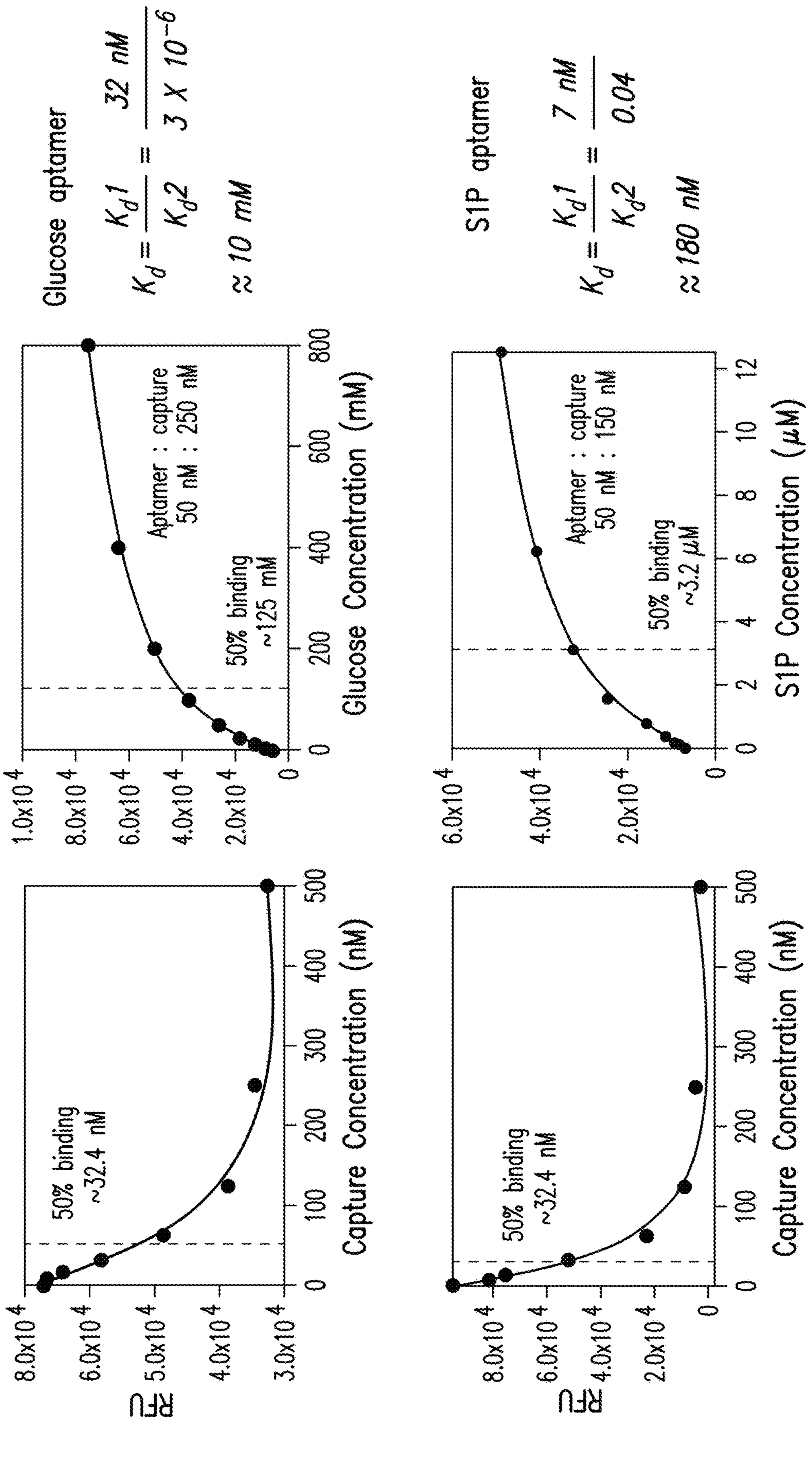

FIG. 8B provides fluorescence curves and dissociation constants ($K_d$) for dopamine, serotonin, glucose, and S1P aptamers. Dotted lines indicate half-maximal responses.

Figure 18:
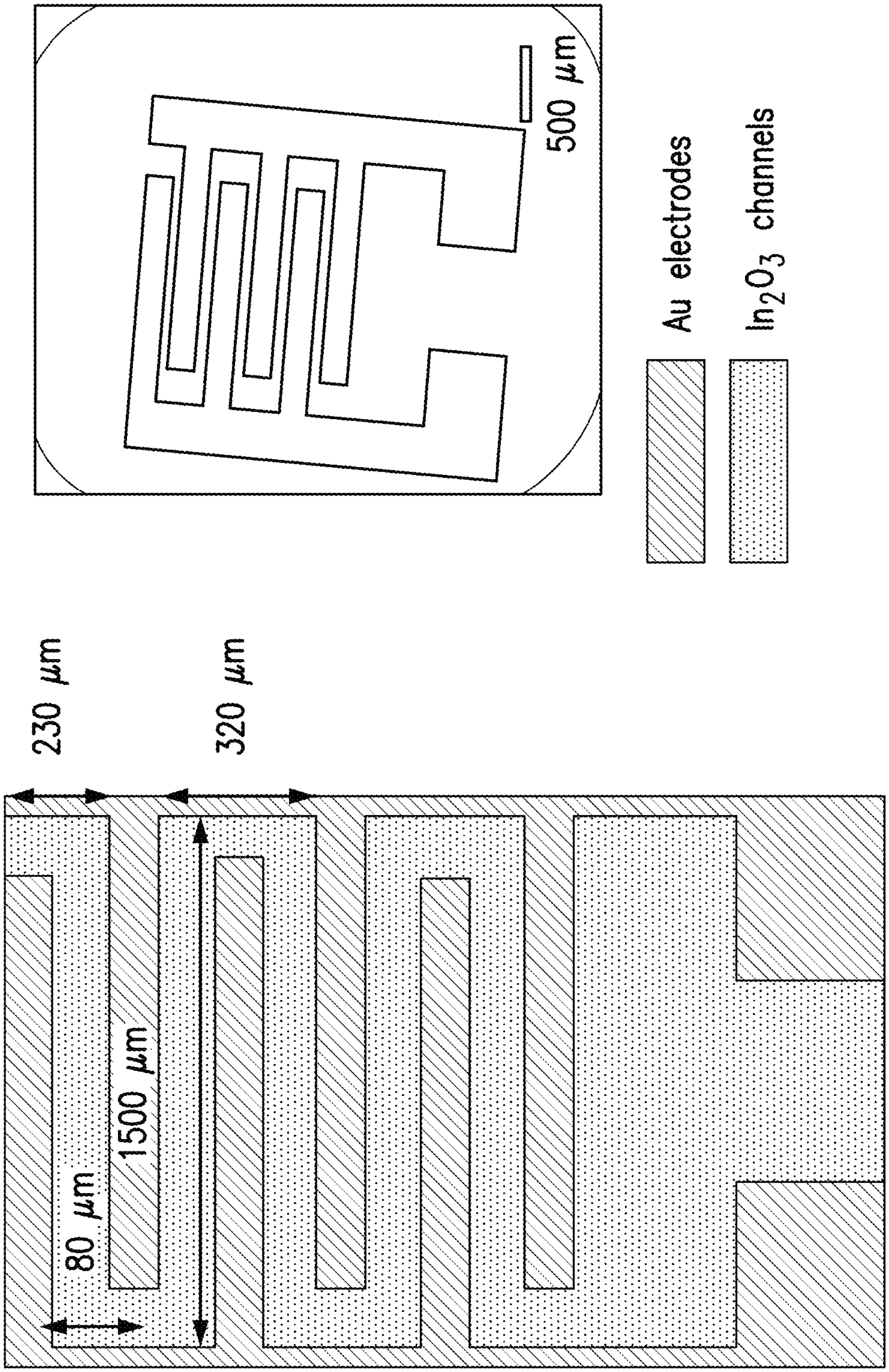
FIG. 18 provides a schematic illustration of an example of field-effect-transistor channel dimensions measured via scanning electron microscopy (SEM).

To enhance channel surface-to-volume ratios, field-effect transistors (FETs) were fabricated with ultrathin (~4 nm) $In_2O_3$ semiconductor films. Aqueous solutions of indium (III) nitrate hydrate ($In(NO_3)_3 \cdot xH_2O$, 99.999%) were spin-coated at 3000 rpm for 30 s onto heavily doped silicon wafers (University Wafer, Boston, MA or WaferPro, San Jose, CA) each having a 100 nm-thick thermally grown $SiO_2$ layer. Substrates were prebaked at 150° C. for 10 min followed by thermal annealing at 350° C. for 3 h. Interdigitated source and drain electrodes (1500 μm length, 80 μm width, 10 nm Ti, 30 nm Au; FIG. 18) were patterned by standard photolithography and deposited by electron-beam evaporation on top of $In_2O_3$ to obtain large transconductances and uniform current distributions.

Transconductance is increased when three parameters in field-effect transistors are considered: (1) intrinsic mobility, (2) per capacitance, and (3) channel width. To achieve high intrinsic mobility, indium oxide was selected as the metal oxide semiconductor due to its high relative electron mobility compared with other materials (organic semiconductors). Operation of devices in physiological environments, which include liquids with very high dielectric constants (e.g., water dielectric constant ~80), would increase the capacitance, which is highly sensitive when the potential is changed. The channel area was increased by using interdigitated electrodes. The effects of each parameter can be assessed by the following equation 3, $$9m = \frac{four}{Vm} = (\mu)(C_{ox})\frac{(W)}{L}(V_{GS}-V_p) = \frac{21_p}{V_{GS}-V_p} \quad (3)$$

Metal oxide semiconductors (μ); Electrolyte gating ($C_{ox}$); interdigitated electrodes (W/L)

where μ represents the carrier mobility of the metal oxide semiconductors, $C_{ox}$ represents electrolyte gating, and W represents the channel width.

Figure 19:
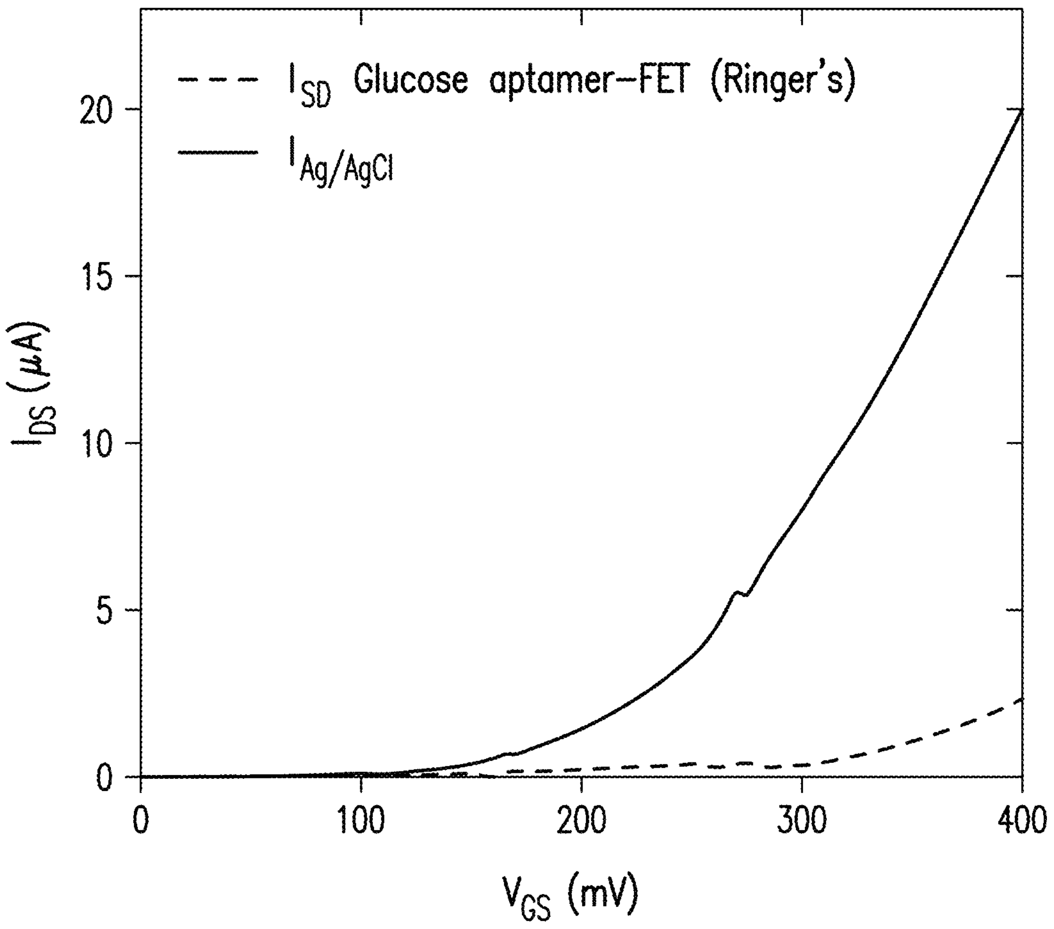
FIG. 19 provides representative transfer curves of glucose aptamer-functionalized field-effect transistors in 1×Ringer's buffer (no target). Minimal drain leakage-current from the Ag/AgCl gate electrode can be observed relative to the source-drain current.

To fabricate FET sensors, aptamers were immobilized on $In_2O_3$ exposed regions using a top-gate device configuration. This configuration has been extensively characterized in the standard dry state. Briefly, (3-aminopropyl)trimethoxysilane (APTMS) and trimethoxy(propyl)silane (PTMS) (1:9 v/v ratio) were thermally evaporated using vapor-phase deposition onto $In_2O_3$ surfaces at 40° C. for 1 h followed by incubation in 1 mM ethanolic solutions of 1-dodecanethiol for 1 h to passivate Au electrodes. In addition to electrode passivation, device-to-device cross-talk with other FETs on each substrate was prevented by isolating each device individually during measurements via PDMS cups. Furthermore, substrates have substantial inter-FET distances (~2 mm; FIG. 1B). Minimal leakage current was detected from the reference electrode (Ag/AgCl; FIG. 19).

For aptamer functionalization, substrates rinsed in ethanol and immersed in 1 mM solutions of 3-maleimidobenzoic acid N-hydroxysuccinimide ester (MBS) dissolved in a 1:9 (v/v) mixture of dimethyl sulfoxide and PBS for 30 min. The MBS crosslinks amine-terminated silane to thiolated DNA aptamers. Aptamers were prepared for attachment to substrates by heating for 5 min at 95° C. in nuclease-free water followed by rapid cooling in an ice bath. Substrates were rinsed with deionized water and immersed in 1 μM solutions of thiolated DNA aptamers for 1 h, rinsed again with deionized water, and blown dry with $N_2$ gas.

Scrambled sequences with the same numbers and types of nucleotides as correct aptamer sequences but with pseudo-random orders were designed to investigate specific aptamer-target recognition via FETs (Table 5). Scrambled sequences were selected based on modeling to adopt significantly different secondary structures compared to the correct sequences.

| | |
|---|---|
| Dopamine scram bled | 5'-/5ThioMC6-D/AGTACGTCGATGCTCGATCA GTGGGCTAGGTGCGTAGCGGTCTG-3' |
| Serotonin scram bled | 5'-/5ThioMC6-D/CCCGGGAATTCCGGAATTGG GGCAATTGATGAGGGGGTCATGGG-3' |
| Glucose scram bled | 5'-/5ThioMC6-D/TTTGAGGTCAATCCCGGTTT AGGCCCCAAGTTTGCGTTGT-3' |
| S1P scram bled | 5'-/5ThioMC6-D/GTGGGGACTTTTCGGTATAA GGGCATTGGGAAATTCGGTGGAGGGA-3' |

Table 5. a list of exemplary scrambled dopamine, serotonin, glucose and SIP aptamer sequences (SEQ ID NOS 82-85, respectively)

Surface ratios of methyl-terminated (PTMS) and amine-terminated (APTMS) silanes were altered to change the numbers of aptamers on serotonin aptamer-FETs. Specifically, ratios of 1:1, 1:19, and 1:49 (v/v) of APTMS:PTMS were vapor deposited on substrates prior to MBS coupling chemistry and subsequent aptamer tethering.

Soft-polymer PDMS wells were sealed on top of individual FETs to hold physiological buffers and targets. Phosphate-buffered saline (0.1× or 1×PBS), artificial cerebrospinal fluid (1×aCSF), HEPES buffer (1×HEPES), or Ringer's solution (1×Ringer's) were used as electrolyte solutions (Table 6).

| Salt | Concentration (mM) |
|---|---|
| 1 × PBS | |
| NaCl | 137 |
| KCl | 2.7 |
| $Na_2HPO_4$ | 10 |
| $KH_2PO_4$ | 1.8 |
| 1 × aCSF | |
| NaCl | 147 |
| KCl | 3.5 |
| $Na_2HPO_4$ | 1.0 |
| $KH_2PO_4$ | 2.5 |
| $CaCl_2$ | 1.0 |
| $MgCl_2$ | 1.2 |
| 1 × HEPES | |
| HEPES | 20 |
| NaCl | 1000 |
| $MgCl_2$ | 10 |
| KCl | 5 |
| 1 × Ringer's | |
| NaCl | 147 |
| KCl | 4 |
| $CaCl_2$ | 2.25 |

Table 6. Ionic contents for phosphate-buffered saline (PBS, pH 7.4), artificial cerebrospinal fluid (aCSF, pH 7.4), HEPES (pH 7.5), and Ringer's buffers (pH 7.4).

Commercially available Ag/AgCl reference electrodes (World Precision Instruments, Inc., Sarasota, FL) were placed in the solutions above the FETs. All FET measurements were performed on manual analytical probe stations (Signatone, Gilroy, CA) equipped with either an Agilent 4155C (Agilent Technologies, Santa Clara, CA) or a Keithley 4200A (Tektronix, Beaverton, OR) semiconductor analyzer.

Figure 20:
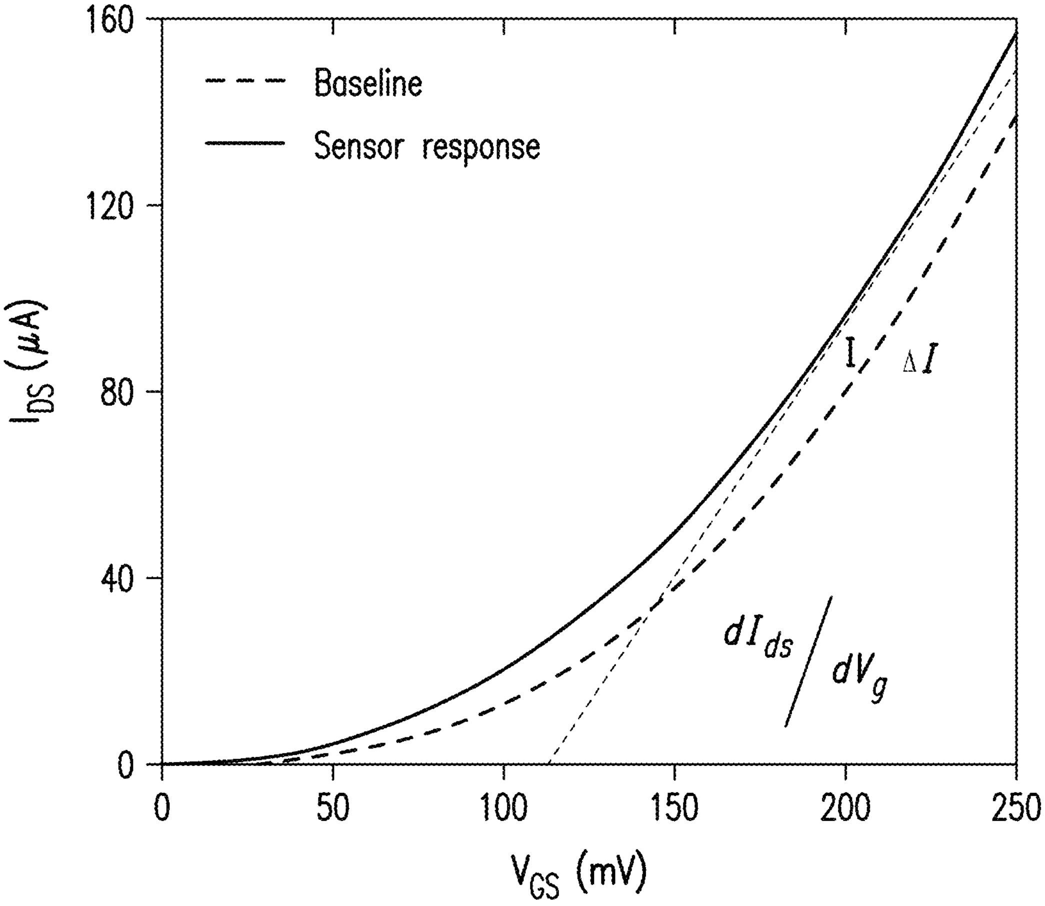
FIG. 20 provides plots illustrating how calibrated sensor responses can be calculated.

Source-drain current ($I_{DS}$) transfer curves were obtained by sweeping the gate-bias voltage ($V_{GS}$) from 0 to 400 mV while maintaining the drain voltage (VD) at 10 mV. Five consecutive sweeps were averaged for each transfer curve determined at each target or nontarget concentration. Calibrated responses were calculated to minimize device-to-device variation. The absolute sensor response (ΔI) that takes into account baseline subtraction was divided by the change in source-drain current with voltage sweep (FIG. 20). The calibrated response can be calculated to minimize device-to-device variation using equation 4:

$$\Delta I_{DS}/\Delta_{VG};\ \text{where}\ \Delta_{VG}=dI_{ds}/dV_g \quad (4)$$

The absolute sensor response (ΔI), which considers baseline subtraction, can be divided by the change in source-drain current with voltage sweep. This method can be based on a correlation between absolute sensor responses and gate dependence in liquid-gate sensing set-ups. This method relies on a correlation between absolute sensor responses and gate dependence in liquid-gate sensing set-ups. All calibrated responses were calculated at a gate-bias voltage of 100 mV. This bias voltage gave maximal current responses with minimal sweep-to-sweep variations.

Figure 21:
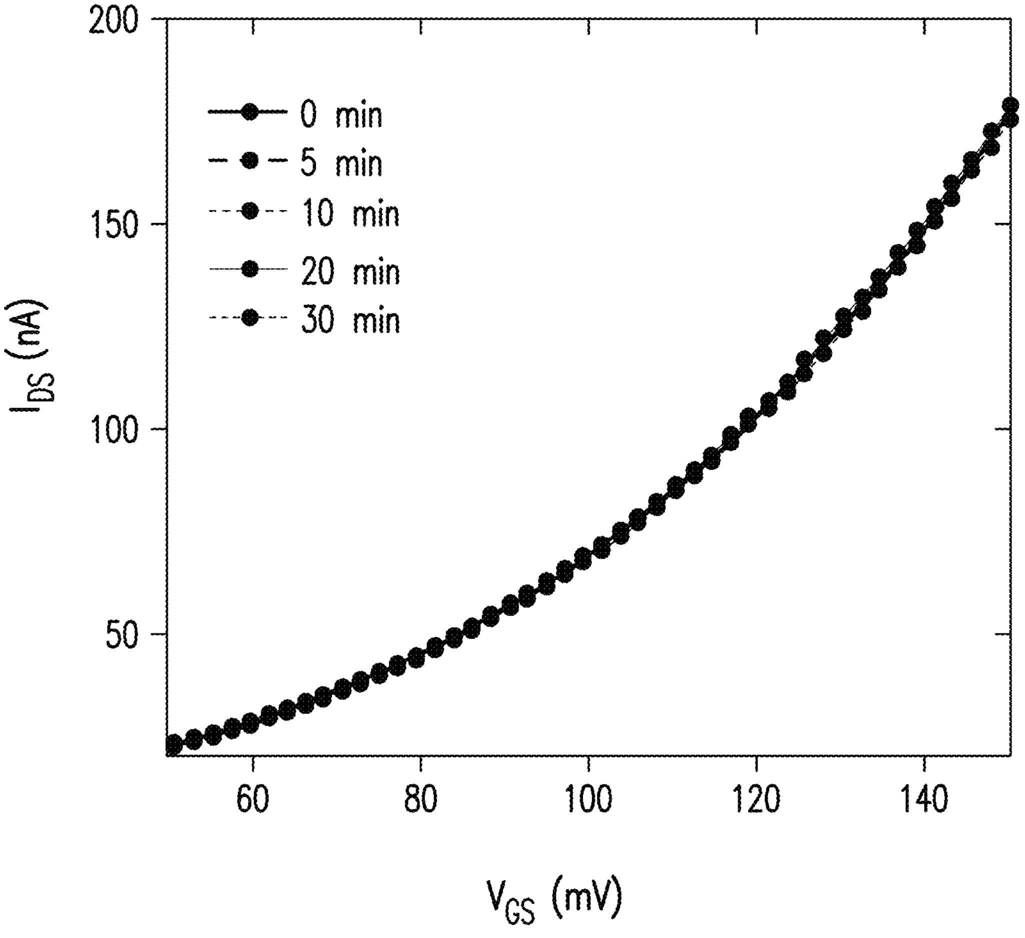
FIG. 21 provides data showing that baseline current in 1×aCSF remained stable over a 30-min period indicative of minimal perturbation of transistor signals by solution ions.

Root-mean square (RMS) noise was calculated in the absence of target with respect to target-associated current changes, as an indicator of the effects of unspecific fluctuations in aptamer conformations. Over 30 min, the baseline current in 1×aCSF minimally fluctuated, indicative of minimal perturbation of transistor signals by solution ions (FIG. 21). For serotonin aptamer-FETs in 1×aCSF, RMS noise at the lowest detectable target concentration (10 fM) was ~3% of baseline. At saturating target concentrations (100 μM), RMS noise was ~4%. Low RMS noise indicates that unspecific aptamer conformation fluctuations contribute minimally to sensor responses.

Data for ~200 individual FETs fabricated over many fabrications runs and produced during a period of 4 years are shown. To determine device yields per substrate, the numbers of transistors that showed standard behavior under solid-state conditions in terms of field-effect mobility, threshold voltage, on/off ratio, and subthreshold slope was determined. Typical device yields at this stage were ~75%.

After aptamer functionalization, the performance of each FET in buffer was tested. Approximately 30% of FETs showed poor baselines that did not stabilize after 10 min. These FETs were not used further giving an overall device yield of ~50%.

Ex Vivo Sensing in Brain Tissue

Brains lacking serotonin were from Tph2 knockout mice provided by the laboratory of Donald Kuhn (Wayne State University, Detroit, MI). All procedures involving these mice were pre-approved by the Wayne State University Institutional Animal Care and Use Committee. Mice were deeply anesthetized with pentobarbital and exsanguinated during cardiac perfusion with PBS to remove blood and thus, peripherally synthesized serotonin. Brains were rapidly removed from the skulls, frozen at −70° C., shipped to the University of California, Los Angeles on dry ice, and stored at −70° C. until use.

On the day of use, brains were thawed on ice and sectioned into quarters in the sagittal and rostrocaudal planes to facilitate homogenization. Each quarter was weighed and transferred to a 1.7-mL Eppendorf tube on ice. Ice-cold 1×aCSF was added to each tube (2 μL/mg tissue). Tissues were sonicated on ice using a VirTis Virsonic 600 ultrasonic cell disruptor (Gardiner, NY) with the microtip set at 4 and 50% duty, using 30-40 1-sec pulses. Homogenates were subdivided into aliquots (40 μL) for FET measurements. Serotonin was added to individual aliquots (10 fM-100 μM final concentrations). Aliquots were briefly vortexed prior to aptamer-FET measurements, which were carried out on six replicate samples per concentration.

To investigate the reproducibility of serotonin aptamer-FETs measurements with respect to tissue exposure, devices tested for target responses immediately after exposure to brain tissue. Substrates were then rinsed with deionized water and tested again in brain tissue for serotonin concentration responses 12 h later. To evaluate serotonin aptamer-FET stability during brain tissue measurements further, sensors were continuously incubated in brain tissue for 1, 2, 3, or 4 h prior to serotonin addition. For selectivity tests in brain tissue, 2 μM of 5-hydroxyindoleacetic acid (5-HIAA) was added to brain tissue, which also lacked endogenous 5-HIAA, prior to serotonin concentration-dependent measurements. Afterwards, a high concentration of dopamine (100 μM) was added to determine selectivity.

Glucose Sensing in Mouse Serum and Whole Blood

The University of California, Los Angeles (UCLA) is an accredited by the Association for Assessment and Accreditation of Laboratory Animal Care. The UCLA Chancellor's Research Program preapproved all procedures involving mice for blood glucose sensing. All animal care and use met the requirements of the NIH "Guide for the Care and Use of Laboratory Animals", revised 2011. Food and water were available ad libitum. The light-dark cycle (12/12 h) was set to lights on at 0600 h (ZT0).

For whole blood samples, the inside walls of 1.5-mL Eppendorf microcentrifuge tubes were pretreated with 50 μL 0.5 M EDTA (Sigma Cat #E7889), air-dried, and used within 12 h. Wildtype (see below) male and female mice were killed by cervical dislocation under deep isoflurane anesthesia. Whole blood samples were collected via an open-chest cardiac puncture procedure. Approximately 300 L of blood was withdrawn from the heart using a 23 G needle. Blood was immediately transferred to ice-cold EDTA pre-treated Eppendorf tubes. Tubes were immediately closed and gently inverted for 10 s, then placed back into ice. Whole blood samples from 3-4 mice were combined and stored at 0-4° C. for no longer than 72 h prior to FET measurements.

Glucose aptamer-FET measurements in whole blood were conducted by diluting whole blood samples with 1×Ringer's buffer (same ionic concentrations as blood) to construct a concentration-dependent curve ranging from 10 nM (limit of detection) to 5 mM (concentration of whole blood, undiluted). After incubation in undiluted whole blood (5 mM), glucose was added to obtain a final solution concentration of 1 M to determine whether FETs had reached saturation.

For serum glucose measurements, three male wildtype mice (serotonin transporter (SERT)+/+)) and three male knockout mice (SERT−/−) at 4-6 months old were studied. All mice for blood determinations were generated at UCLA from a SERT-deficient lineage on a mixed CD1×129S6/SvEv background via SERT heterozygous pairings. After weaning, mice were housed in groups of 3-5 same-sex siblings per cage before and throughout the experiment, with the exception of single-housing during the 24 h fasting period and the follow-up 25 min glucose challenge test.

Three baseline, one fasted, and one glucose challenge blood samples were collected during ZT0:10-ZT1:30 for each subject. In brief, on each testing day, a body weight measurement was taken first. Then, a small incision was made on tail to nick the tail vein. The first drop of the blood was used for a blood glucose measurement via a glucometer (Contour Next EZ Blood Glucose Monitoring System, Ascensia Diabetes Care, Parsippany, NJ). Immediately, 70-100 L blood samples were collected via Capiject tubes (Terumo Medical Corporation, Elkton MD), and stored in ice. Subjects were allowed to recover for 1-2 days before the next blood collection.

After completing three baseline collections, mice were singly housed and fasted for 24 h before undergoing glucometer glucose measurements and fasted blood collection for aptamer-FET glucose determination. Glucose (1 g/kg, i.p.) was then administrated to each mouse (Sigma Cat #D9434). After 25 min, glucose-challenged blood glucose measurements were made by glucometer and collection of a second blood sample occurred for subsequent aptamer-FET measurements.

Blood samples for aptamer-FET determinations were placed on ice for ~30 min to complete the coagulation process. Blood samples were then centrifuged at 13,000 rpm at 4° C. for 15 min. The serum fraction of each sample was transferred to fresh ice-cold Eppendorf tube. Serum samples were stored at −80° C. until FET measurements.

One experimenter carried out glucometer glucose determinations, collected blood samples, and prepared serum. A different experimenter carried out serum glucose aptamer-FET measurements. The experiment was carried out in a double-blind manner-both experimenters were unaware of mouse genotypes during the experiment. Furthermore, the second experimenter was also unaware of serum sample group (i.e., basal, fasted, or glucose challenged).

For each substrate, one FET was used to determine calibration curves for glucose in 1×Ringer's (10 fM-100 mM) to calibrate concentration-dependent transistor behavior. The other FETs on these substrates were used to measure glucose levels in serum samples. Glucose concentrations in serum ranged from 5-28 mM (determined via glucometer) and were in agreement with reported glucose concentrations. Since the second experimenter was blind to the glucose concentration in each sample, she assumed ~10 mM glucose in each serum sample and serially diluted each sample with 1×Ringer's until a theoretical concentration of ~10 μM glucose was reached. This latter concentration is within the most sensitive detection range determined from glucose calibration curves in 1×Ringer's solution. On each FET, the experimenter measured the baseline current (Ringer's buffer), then added a sample of diluted serum so that the final glucose concentration in the PDMS well was theoretically ~10 μM. Next, a standard addition of glucose (100 μM) was added to each well/FET to determine the response to be fit to the calibration curve. Concentrations of glucose in each serum sample were back-calculated from the slope of the calibration curve taking into account the dilution factor.

Surface-Enhanced Raman Spectroscopy

Localized surface-plasmon resonance, i.e., hot spots, occurring in plasmonic nanostructures, significantly enhance Raman signals from adsorbed molecules. As such, surface-enhanced Raman spectroscopy has been used to detect ultra-low target concentrations and even single molecules. Additionally, SERS is sensitive to conformational changes associated with DNA-base interactions or molecular orientations resulting in shifts in SERS spectra. Halas and co-workers reported SERS detection of target-aptamer binding by analyzing spectral reproducibility. Au nanoshells were employed as SERS substrates due to uniform and large hot spots (FIG. 13B), and high spectral reproducibility.

Figure 13A:
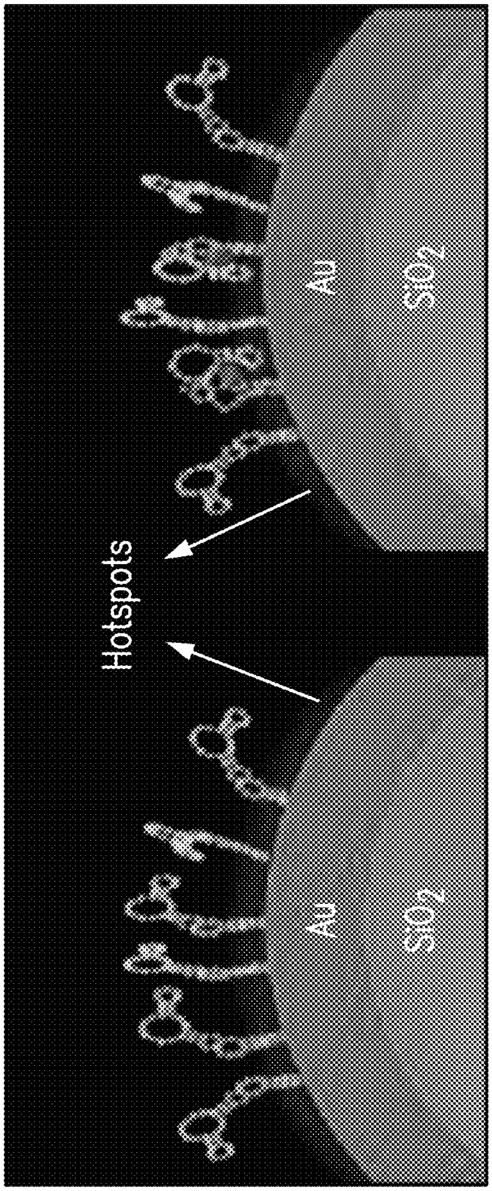
FIG. 13A provides a schematic illustration of thiolated aptamer self-assembled monolayers on Au nanoshells (Left). Conformational changes in aptamers induced by target molecule interactions can alter aptamer vibrational modes within the hot spots of the Au nanoshells (Right).
Figure 13B:
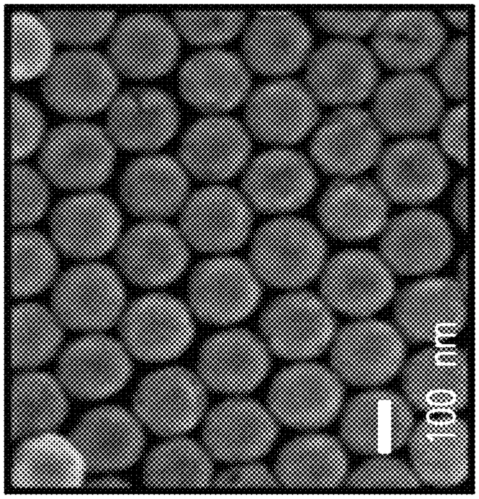
FIG. 13B provides a scanning electron microscopy image of uniformly packed Au nanoshells.

The Au nanoshells in surfactant poly(4-vinylpyridine) had silica cores with diameters 83±5 nm, Au-shell thicknesses 30±7 nm, and peak absorption at 660 nm in water, and were purchased from Nanocomposix Inc. (product number GSPN 660-25M, 0.05 mg/ml; San Diego, CA). The Au nanoshells were dispersed and centrifuged in acetone twice to remove surfactant. They were then washed with ethanol twice and re-dispersed in deionized water. Aliquots (40 μl) of Au nanoshell dispersions were drop-cast onto clean glass slides and dried on a hotplate at 40° C. to form red ring-shaped films. These "coffee" rings consisted of close-packed monolayers of Au nanoshells, as determined by scanning electron microscopy (SEM) (FIG. 13B). Images were taken using a Zeiss Supra 40VP scanning electron microscope. The SERS substrates were made conductive by sputtering several nm of Au/Pt for SEM imaging.

Thiolated aptamers (5 μM in nuclease-free water) were heated at 95° C. for 5 min and cooled to room temperature slowly to relax molecules into extended conformations. Aptamers were then incubated overnight with Au nanoshells for self-assembly of monolayers. A Renishaw in confocal Raman microscope (Wotton-under-Edge, United Kingdom) was used to collect SERS spectra. A HeNe laser operating at 632.8 nm, in resonance with the absorption peak of Au nanoshells, was used for Raman excitation. The laser intensity was set at 25 μW (0.5% of total power) to avoid damaging DNA. A 50× objective was used to collect high-resolution spectra. Each spectrum was collected using a 20-s integration time, which allowed the accumulation of 10 spectra, each with a 2 s exposure. A total of 20 spectra were collected for each sample and two replicate samples were tested for each condition.

Raman signatures of large molecules are enhanced only in close-proximity to metal surfaces due to the short range of the strongest enhancements within ~1 nm of surfaces. After dopamine, serotonin, glucose, or S1P were introduced, SERS spectra for the respective aptamer-thiol self-assembled monolayers exhibited complex and random pattern changes (FIG. 13C-F) induced by target-aptamer interactions. For all aptamers, in the absence of targets or in the presence of non-target compounds, the SERS spectra of aptamers did not exhibit changes (FIG. 13C-F). In concordance with FET transconductances, changes in SERS spectra in response to aptamer-target recognition reflected aptamer conformational changes, e.g., contractions or expansions of backbones, and/or rearrangements in the relative positions of aptamer loops in proximity to semiconductors.

Circular Dichroism Spectroscopy

Spectral circular dichroism (CD) signatures are dominated by exciton interactions induced by stacking of hydrophobic bases in asymmetric helices. Therefore, the intensities and positions of the positive and negative peaks for oligonucleotides in sigmoidal CD spectra are sensitive to the extent of base stacking and the orientations of dipole moments.

For CD experiments, aptamer and target concentrations were 2 μM in 1×PBS, 1×aCSF, or 1×HEPES. Aptamers were thermally treated as described above for SERS spectroscopy. Spectra were collected on a JASCO J-715 circular dichroism spectrophotometer (Oklahoma City, OK) at room temperature. Four scans were acquired per sample with 0.5 nm resolution, 1.0 nm bandwidth, a 4 s response time, and a 20 nm/min scan rate. Scans shown in the figures are averages of four instrumental scans and are representative of two replicates per condition. Scans in 1×PBS, 1×aCSF, or 1×HEPES without targets were subtracted as background.

Förster Resonance Energy Transfer

All Förster resonance energy transfer (FRET) measurements were performed on a Perkin Elmer LS55 spectrofluorimeter (Waltham, MA). Emission spectra were monitored in the 500-650 nm range using excitation at 470 nm for fluorescein (FAM), with 10 nm excitation and 10 nm emission slits using Perkin Elmer luminescence spectroscopy cells containing 120 μL of solution. Oligonucleotides modified with donor and acceptor fluorophores and purified by HPLC were purchased from Integrated DNA Technologies.

aptamers for suitable fluorophore positions for FRET signaling were screened, with 5-carboxytetramethylrhodamine (TAMRA) at the 3' ends and internal FAM locations. FRET sensors that did not have clean isosbestic points and where fluorescein was sensitive to its environment were eliminated, as these would not lead to straightforward observations of changes upon target binding.

Figure 17A:
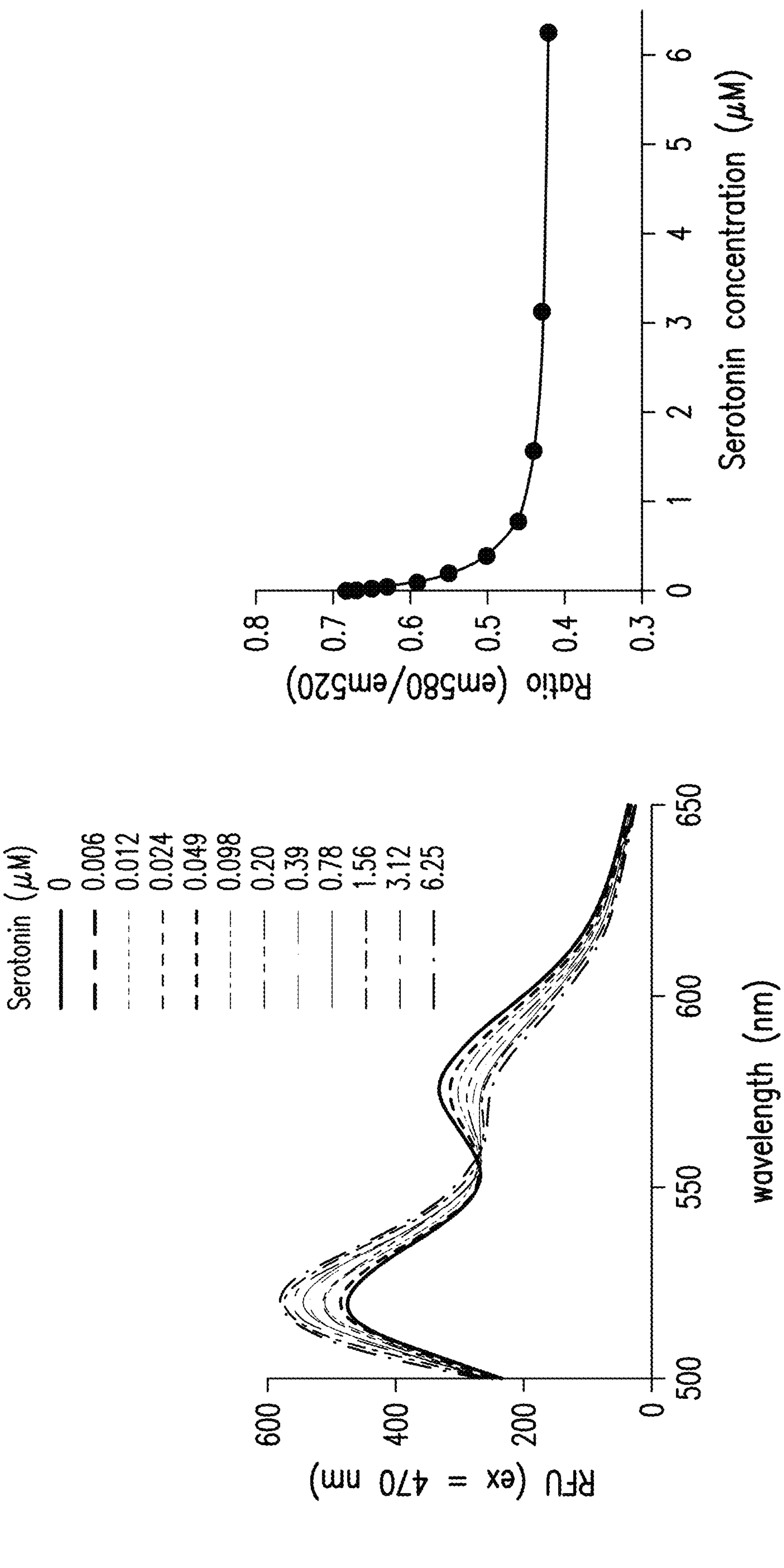
FIGS. 17A-B provide plots of Forster resonance energy transfer (FRET) between donor, fluorescein (FAM), excited at 470 nm, and acceptor, 5-carboxytetramethylrhodamine (TAMRA) with respect to increasing target concentrations for (17A) serotonin and (17B) glucose aptamers, corresponding to FIG. 6B.
Figure 17B:
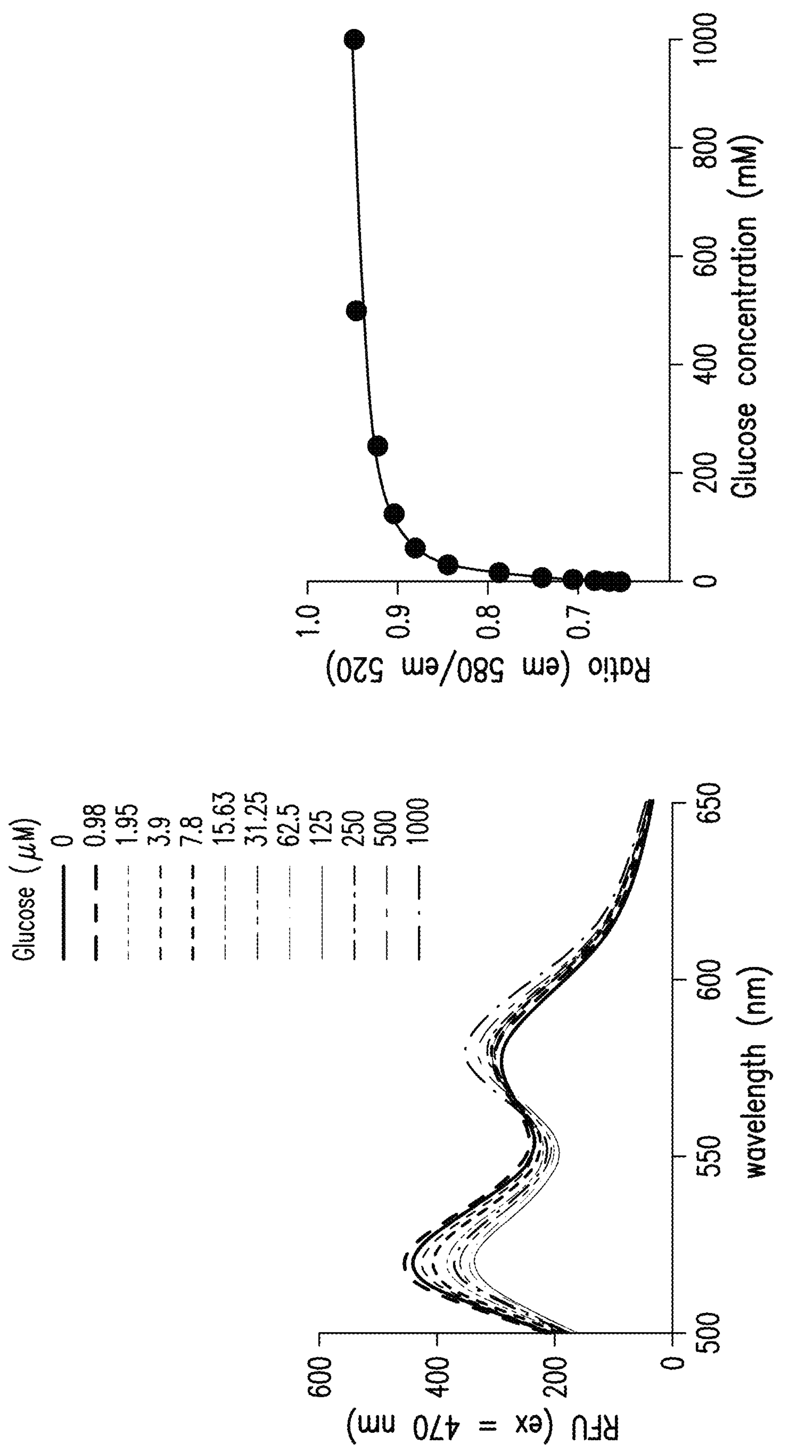

For glucose, samples contained 200 nM fluorescent oligonucleotide in buffer (20 mM HEPES, 1 M NaCl, 10 mM $MgCl_2$, 5 mM KCl, pH 7.5). Samples were heated at 95° C. for 5 min and cooled to room temperature. The aptamer solution was then mixed with an equivalent volume of 400 nM glucose solution. Samples were incubated for 40 min at room temperature prior to collection of spectra. For serotonin, all conditions were identical expect the buffer was PBS including 2 mM $MgCl_2$ (pH 7.4). All FRET measurements were performed in duplicate. The FRET efficiencies, defined as the portion of the donor (FAM) fluorescence that was transferred to the acceptor (TAMRA), were evaluated using the ratio of the fluorescence intensity of TAMRA to that for FAM (ratio=emission 580/emission 520; FIGS. 17A and 17B).

Statistics

Figures 11A, 11B, 11C:
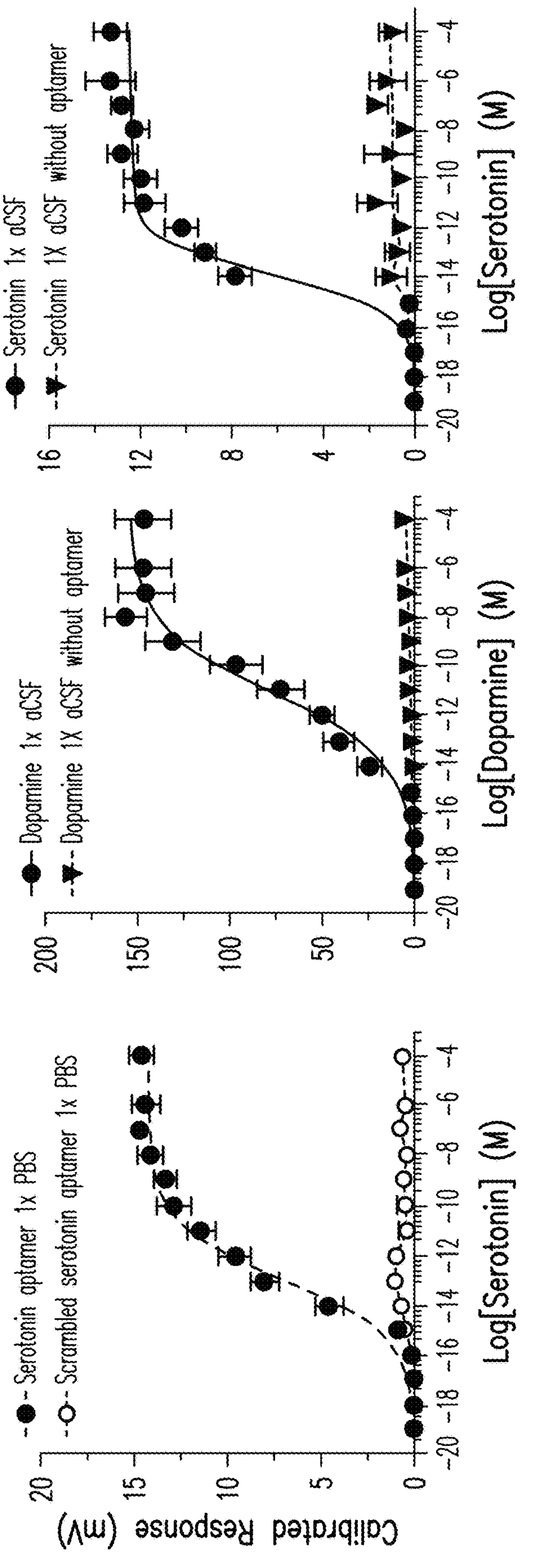
FIG. 11A provides response plots of serotonin-aptamer-field-effect transistors (FETs) in 1×phosphate-buffered saline.
FIG. 11B provides response plots of dopamine-aptamer-field-effect transistors (FETs) in 1×aCSF with/without dopamine aptamers.
FIG. 11C provides response plots of serotonin-aptamer-field-effect transistors (FETs) in 1×aCSF with/without serotonin aptamers.

Data for fluorescence assays and FET calibrated responses are reported as means standard deviations and were analyzed using GraphPad Prism 7.0 (GraphPad Software Inc., San Diego, CA). Concentration-dependent FET responses were analyzed by two-way analysis of variance (ANOVA) with concentration (repeated measure) and buffer/target condition as the independent variables (FIG. 11A-C). Statistics are shown in Table 7.

| FIG. | Interaction term | Condition | Concentration |
| --- | --- | --- | --- |
| 2A | $F(28, 210) = 14806$ | $F(2, 15) = 17614$ | $F(14, 210) = 16949$ |
| | $P < 0.001$ | $P < 0.001$ | $P < 0.001$ |
| 2B | $F(28, 210) = 942$ | $F(2, 15) = 670$ | $F(14, 210) = 1343$ |
| | $P < 0.001$ | $P < 0.001$ | $P < 0.001$ |
| 2C | $F(28, 210) = 736$ | $F(2, 15) = 727$ | $F(14, 210) = 3378$ |
| | $P < 0.001$ | $P < 0.001$ | $P < 0.001$ |
| 2H | $F(10,100) = 10694$ | $F(1, 10) = 864$ | $F(10, 100) = 16679$ |
| | $P < 0.001$ | $P < 0.001$ | $P < 0.001$ |
| 2I | $F(40, 250) = 949$ | $F(4, 25) = 408$ | $F(10, 250) = 3916$ |
| | $P < 0.001$ | $P < 0.001$ | $P < 0.001$ |
| S5A | $F(10, 44) = 198$ | $F(10, 44) = 1295$ | $F(1, 44) = 2067$ |
| | $P < 0.001$ | $P < 0.001$ | $P < 0.001$ |

Table 7 concentration-dependent field-effect transistor data that can be analyzed by two-way analysis of variance with concentration (repeated measure) and buffer/target condition as the independent variables.

Figure 12A:
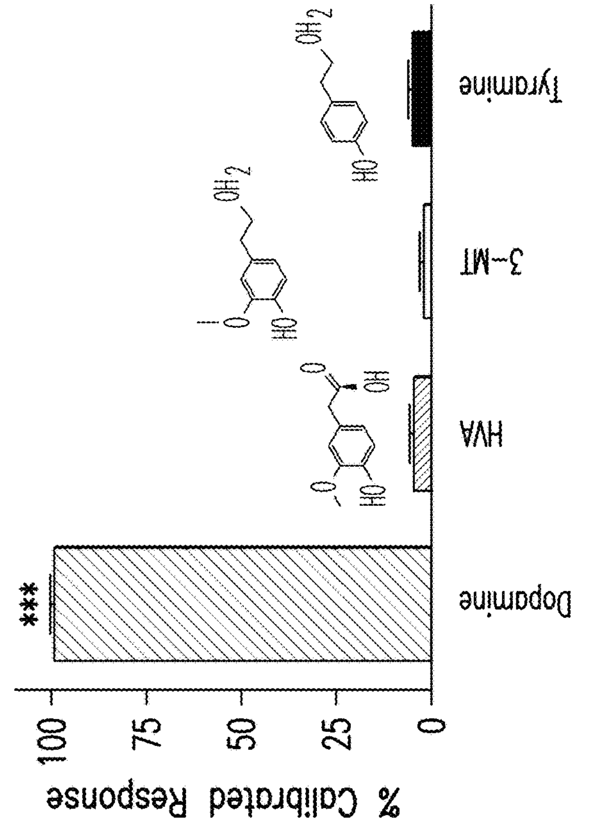
FIG. 12A provides response graphs of dopamine-aptamer-FETs, which can distinguish dopamine from homovanillic acid (HVA), 3-methoxytyramine (3-MT), or tyramine.
Figure 12B:
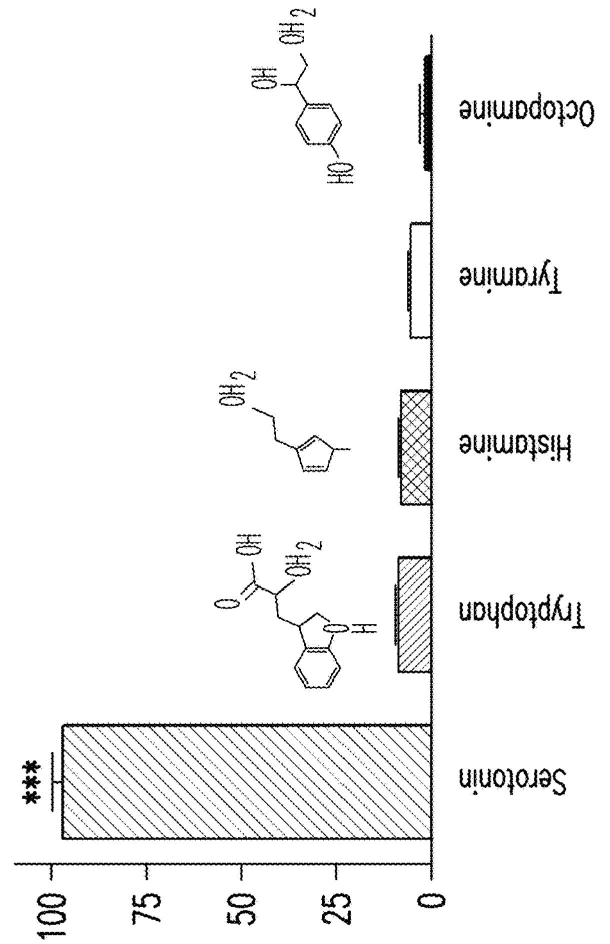
FIG. 12B provides response graphs of serotonin-aptamer-FETs, which can distinguish serotonin from other monoamine neurotransmitters.

Data for counter-target selectivity were normalized to mean responses for correct targets and are reported as % calibrated responses (FIGS. 12A and 12B). These data were analyzed by one-way ANOVA with omnibus statistics reported in Table 8. Post hoc comparisons were by Tukey's multiple comparisons. In all cases, $P<0.05$ was considered statistically significant.

| FIG. | Target |
| --- | --- |
| 3B Left | $F(4, 10) = 16622$; $P < 0.001$ |
| 3B Right | $F(4, 10) = 3148$; $P < 0.001$ |
| 17 A | $F(3, 8) = 19491$; $P < 0.001$ |
| 17 B | $F(4, 10) = 4830$; $P < 0.001$ |

Table 8. Dopamine- and serotonin-aptamer-field-effect transistor responses to targets or counter-targets. A general solution to direct electronic detection of small molecules under physiological high ionic-strength conditions are provided herein. Ultrathin metal-oxide field-effect transistor arrays with deoxyribonucleotide aptamers selected to bind their targets adaptively were used. Target-induced conformational changes of negatively charged aptamer phosphodiester backbones in close proximity to semiconductor channels gate conductance, resulting in highly sensitive detection. Field-effect-transistor-based sensing of charged and electroneutral targets, including serotonin, dopamine, glucose, and sphinghosine-1-phosphate is enabled by newly isolated aptameric stem-loop receptors. This approach overcomes the fundamental limitation of shielding of recognition events on semiconductor surfaces by electrical double layers ('Debye length' limitation) and is broadly applicable to a wide range of important yet difficult targets.

Field-effect transistors (FETs) modified with target-specific receptors potentially provide for direct electronic target detection. Signal transduction and amplification in FET-based sensors is based on electrostatic gating of thin-film semiconductor channels by target-receptor interactions such that even low receptor occupancy significantly and measurably affects transconductance. Two fundamental limitations have prevented the widespread adoption of receptor-modified FETs. First, the electrical double layer in solutions containing ions shields semiconductor charge carriers, limiting gating in response to recognition events. The extent of shielding, i.e., the effective sensing distance, is characterized by the Debye length, which is <1 nm in physiological fluids. The Debye length can be calculated using the following equation 5.

$$\lambda_D = \sqrt{\frac{\varepsilon_0 \varepsilon_r K_B T}{2 N_a e^2 I}} \tag{5}$$

where $\lambda_D$ is the Debye length, $\varepsilon_0$ is the permittivity of tree space, $\varepsilon_r$ is the dielectric constant, $K_B$ is Boltzmann's constant, T is temperature (in Kelvin), $N_a$ is Avogadro's number, e is elementary charge, and I is the electrolyte ionic strength. Debye lengths and ionic strengths in various buffers are listed in Table 9.

| Buffer | Ionic strength (mM) | Debye length (nm) |
| --- | --- | --- |
| 0.01 × PBS | 1.627 | 7.53 |
| 0.1 × PBS | 16.27 | 2.38 |
| 1.0 × PBS | 162.7 | 0.75 |
| 1.0 × aCSF | 159.5 | 0.74 |

Table 9. List of Debye lengths and ionic strengths in various buffers.

Second, small target molecules with few or no charges have minimal impact on semiconductor transconductance, unless they trigger conformational changes in charged receptors within or near the Debye length, or otherwise affect surface potentials.

Both were overcome by combining sensitive FETs with a specific type of oligonucleotide stem-loop receptor selected for adaptive target recognition (FIG. TA). Nanometer-thin $In_2O_3$ FETs (FIG. 1B) are produced by methods that facilitate micro- and nanoscale patterning and are readily scalable with respect to fabrication at high densities and for large numbers of devices. Sensing via FETs is inherently nonlinear, enabling target detection over larger and lower concentration ranges compared to equilibrium-based sensors. The combination of ligand-induced stem-loop conformational rearrangements involving negatively charged phosphodiester backbones, together with associated counterions in close proximity to the surfaces of quasi-two-dimensional FETs, can enable signal transduction and amplification under biologically relevant conditions and for low-charge and neutral targets.

A multiplicity of FET sensors can be used for multiplexed detection of multiple analytes and/or to cover a broader range of concentrations than might be possible with a single sensor element. An array of sensors can also be used to provide spatial or spatiotemporal information, e.g., for in vivo measurements.

Solution-phase selection that circumvents tethering small-molecule targets and is based on stem-loop closing was used to isolate receptors (FIG. 2A), with appropriate counter-selection against interferents. This approach yields aptamers characterized by adaptive-loop binding. The strategies and details of the selection and counter-selection processes are given in (FIG. 7). Original receptors for dopamine, serotonin, glucose, and sphingosine-1-phosphate (S1P) (FIG. 2B-E) were isolated. In addition, FET devices were constructed using a previously reported dopamine aptamer that uses dilute ion concentrations for sensing, leading to the targeting of dopamine. Serotonin was pursued as an important neurotransmitter target having no aptamers with publicly reported sequences. For comparison, glucose was selected as an example of an important small, neutral target. Aptamers interacting directly with glucose have not been reported (although cf. aptamers for glucose sensors). The relatively soluble lipid, S1P (critical micellar concentration <10 μM), which prevents chemotherapy-associated apoptosis, was chosen as an example of a zwitterionic target.

Figure 9:
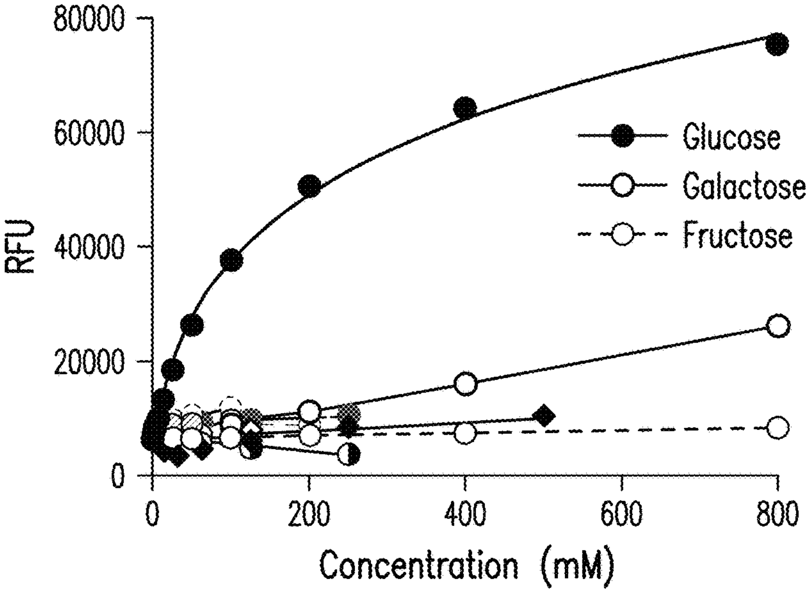
FIG. 9 provides fluorescence response plots of a glucose aptamer in the presence of target (glucose) or similarly structured non-targets.
Figure 9:
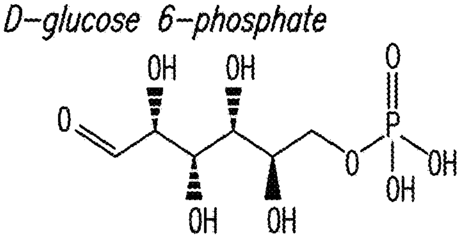
Figure 9:
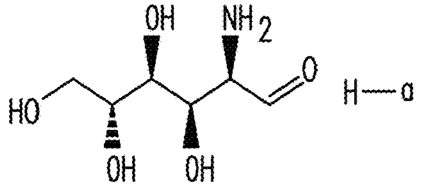
Figure 9:
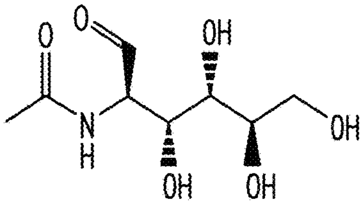
Figure 9:
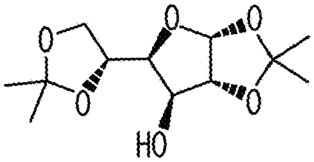
Figure 9:
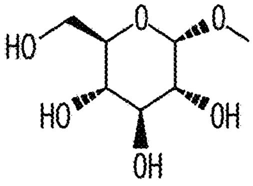
Figure 9:
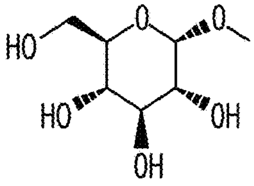
Figure 9:
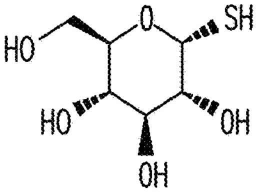
Figure 9:
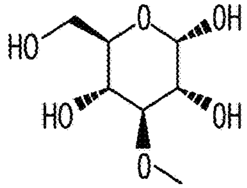

Fluorescence assays were used to characterize aptamer-target dissociation constants ($K_d$) (FIG. 8A). Selection led to high-affinity aptamers for dopamine (150 nM) and serotonin (30 nM) (FIGS. 8B and 8C). Counter-selection eliminated interactions with other monoamine neurotransmitters and metabolites (FIGS. 8B and 8C), critical for sensing in the presence of high concentrations of similarly structured counter-targets in vivo. Notably, our dopamine aptamer does not recognize norepinephrine, in contrast to cross-reactivity plaguing a previously reported dopamine aptamer. Poor selectivity is also problematic for fast-scan cyclic voltammetry, the most common method for sensing dopamine. The affinity of the glucose aptamer (~10 mM) (FIG. 8B) and selectivity with respect to analogs (FIGS. 8D and 9) were consistent with the receptor recognizing hydrophobic surfaces of glucose. FIG. 9 provides fluorescence concentration curves that were obtained via competition with complementary strands and be the result of triplicate measurements with standard deviations too small to be visualized on the plots shown. The affinity of the S1P aptamer was 180 nM (FIGS. 2E and 8B), which was not as high as a reported spiegelmer (4 nM).

Figure 10:
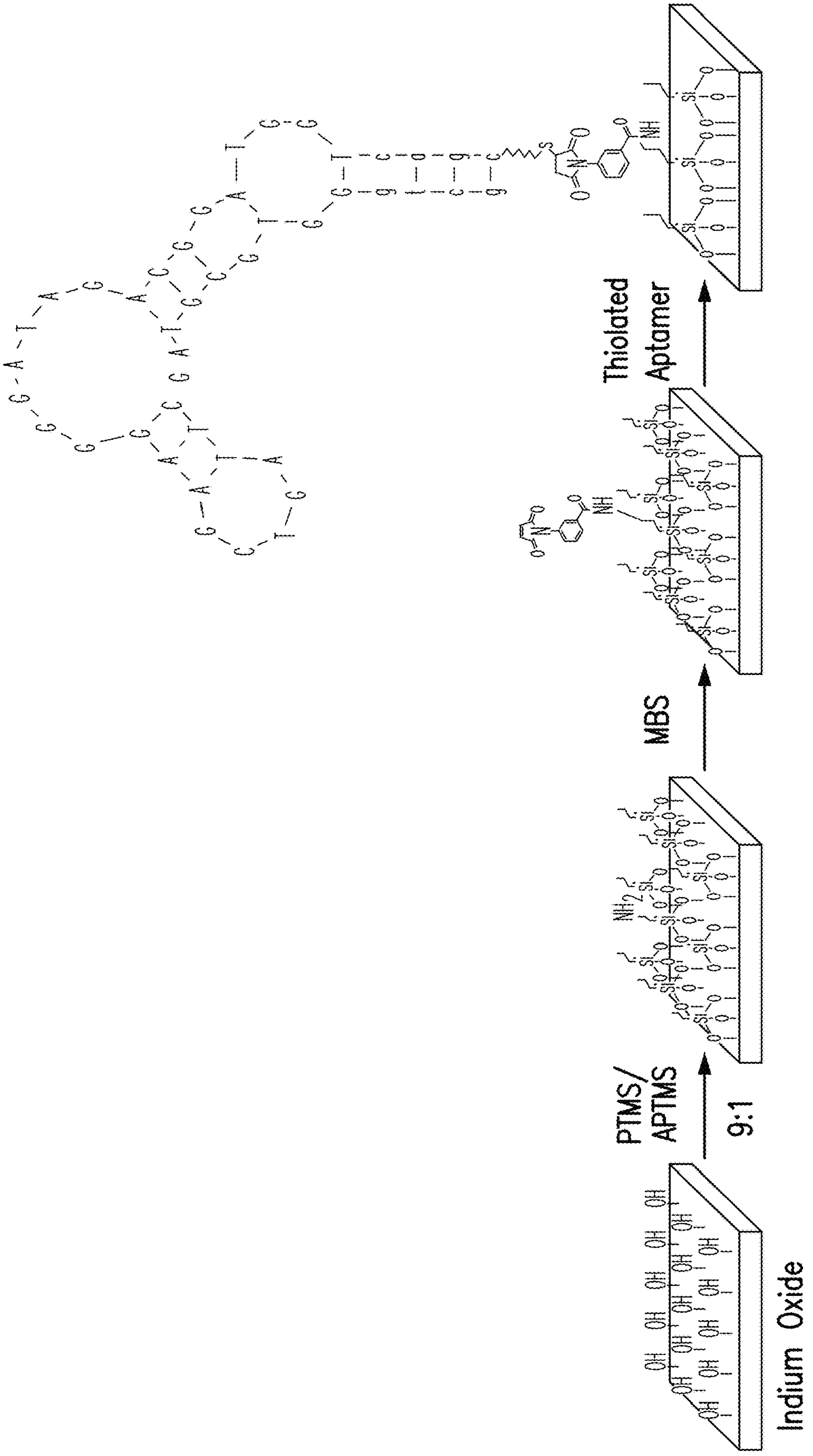
FIG. 10 provides a schematic flow of surface functionalization chemistry for tethering thiolated DNA aptamers to amine-terminated silanes with methyl-terminated background matrix molecules (1:9 ratio). Figure discloses SEQ ID NO: 45.

Thin-film $In_2O_3$ FETs were covalently modified with dopamine or serotonin aptamers via silane chemistry (FIG. 10) to investigate electronic small-molecule detection (FIG. 1A). Despite sub-nanometer Debye screening lengths, aptamer-FETs responded to wide ranges of target concentrations ($10^{-14}$-$10^{-9}$ M) in undiluted, i.e., physiological, phosphate-buffered saline (PBS) (FIG. 3A) or artificial cerebrospinal fluid (aCSF) (FIG. 3A). Scrambled aptamer sequences (Table 5) produced negligible responses (FIGS. 3A and 15A), as did FETs lacking aptamers. FIG. 11 shows that field-effect transistors without dopamine or serotonin aptamers functionalized to semiconducting channels can show negligible sensor responses in the presence of targets. Even at physiological ion concentrations and hence, significantly reduced Debye lengths, FET responses for our dopamine aptamer were more than three orders of magnitude greater than those of the previously reported dopamine aptamer in PBS diluted tenfold (FIG. 3A), due to by-design positioning of recognition regions capable of adaptive conformational changes.

Figure 13C:
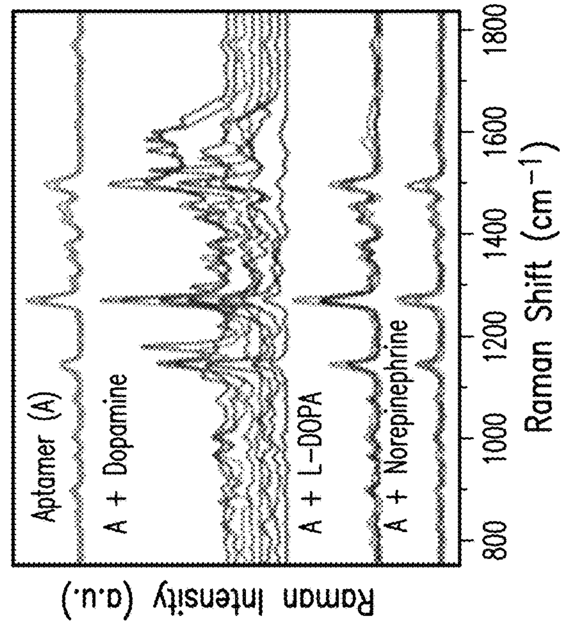
Figure 13D:
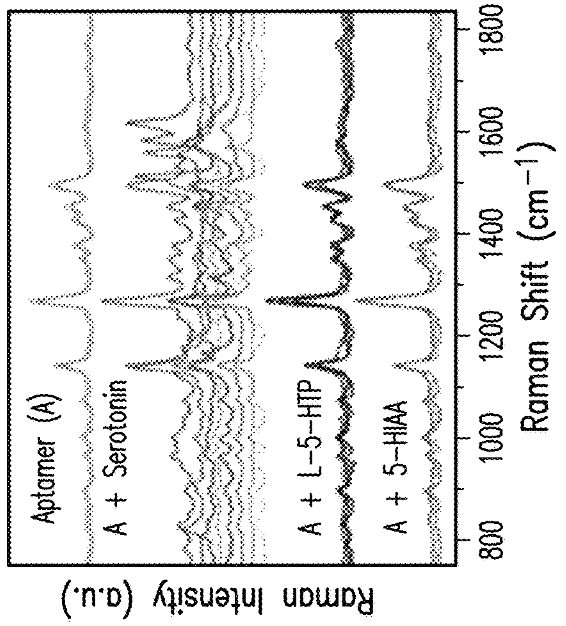

Dopamine-aptamer-FETs were selective for dopamine vs. serotonin, norepinephrine, tyramine, and dopamine metabolites (FIG. 3B and Table 5). Serotonin-aptamer-FETs were selective for serotonin vs. dopamine, norepinephrine, histamine, and other biogenic amines and indole metabolites (FIG. 3B). Aptamer-FET target selectivity was further investigated via surface-enhanced Raman spectroscopy (SERS; FIGS. 13A and 13B). Raman signatures are enhanced only in close proximity to metal surfaces due to the short range of evanescent fields, with the strongest enhancement within ~1 nm of surfaces (similar to the physiological Debye length). After dopamine or serotonin were introduced, SERS spectra for the respective aptamer-thiol self-assembled monolayers exhibited complex pattern changes that were not evident with nontarget compounds (FIGS. 13C and 13D).

Figure 14A:
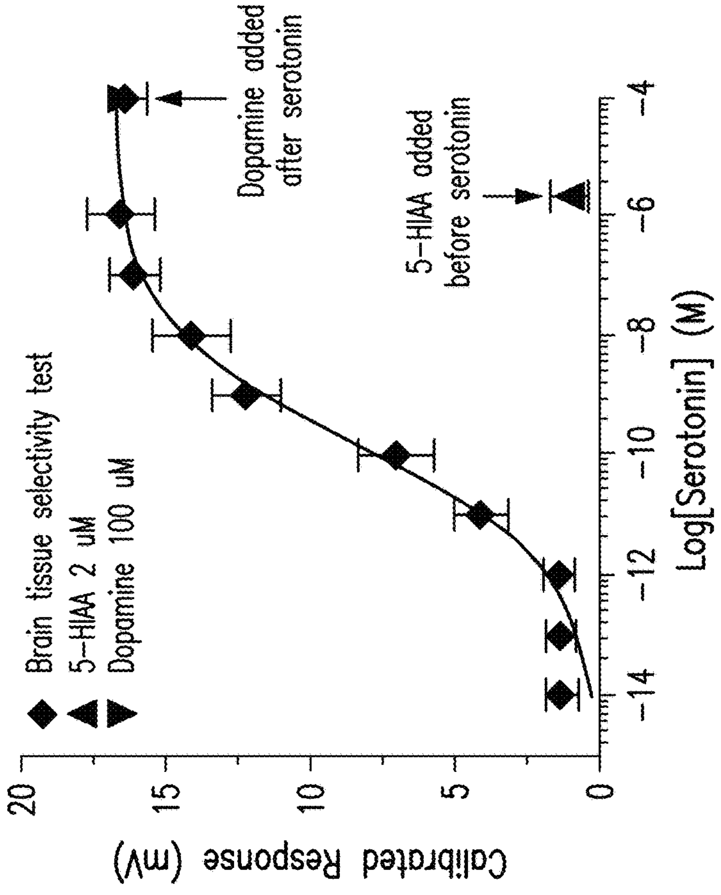
FIG. 14A provides a plot showing selectivity of serotonin-aptamer-field-effect transistors (FETs) in brain tissue.
Figure 14B:
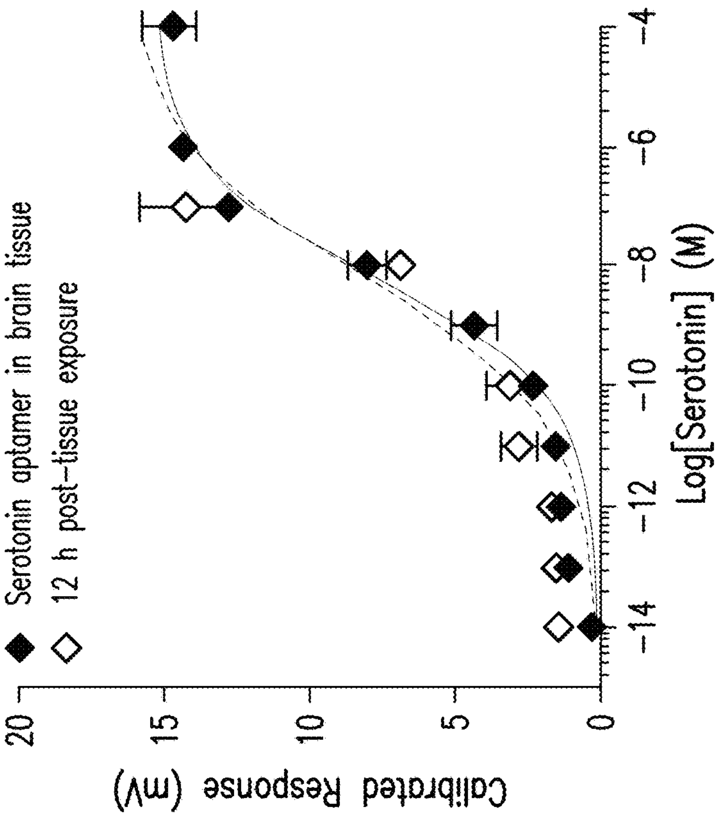
FIG. 14B provides a plot of concentration-dependent responses for serotonin-aptamer-functionalized FETs after initial exposure to brain tissue and the reproduction of these responses 12 h later in brain tissue.

To evaluate sensing in native environments, serotonin was added to brain tissue from mice lacking neuronal serotonin, i.e., Tph2 null mice. Electronic FET responses differentiated physiologically relevant serotonin concentrations (10 pM-100 nM). Sensor responses to dopamine or the major serotonin metabolite, 5-hydroxyindoleacetic acid in tissue were negligible (FIG. 14A). The serotonin metabolite, 5-hydroxyindoleacetic acid (5-HIAA; 2 μM) was added prior to serotonin at increasing concentrations to account for an ambient background of 5-HIAA. Dopamine (100 μM) was added after the highest concentration of serotonin to test cross-reactivity in tissue. Both nonspecific targets minimally perturb the sensor response. The initial high sensitivity of aptamer-FETs offsets losses often encountered in biological environments and sensitivity for modest changes in target concentrations was observed despite large concentration sensing ranges. Moreover, concentration sensitivity ranges can be "tuned" by altering the numbers of serotonin aptamers on FET surfaces (FIG. 4A). Sensor performance retested in tissue after 12 h suggested stable device performance (FIG. 14B). Continuous exposure of serotonin-aptamer FETs to brain tissue for 1-4 h resulted in reproducible concentration-dependent conductance responses further indicating sensor stability (FIG. 4B).

Figure 13E:
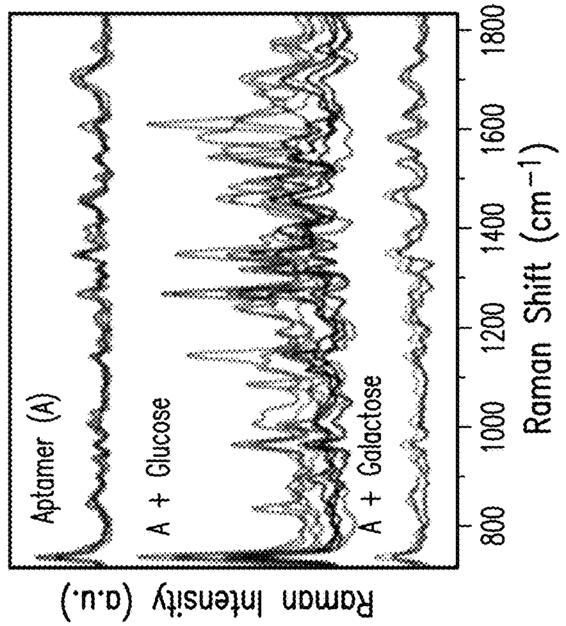
Figure 13F:
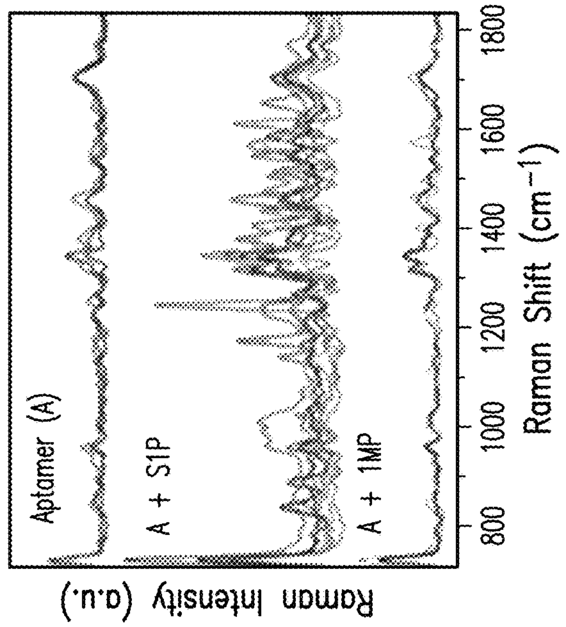

Aptamer-FET responses to the zwitterionic lipid S1P were from 10 pM-100 nM, with negligible responses to a non-target lipid (1-myristoyl-2-hydroxy-sn-glycero-3-phosphoethanolamine) having similar epitopes (FIG. 4C). A scrambled S1P sequence (Table 5) also showed negligible responses. Glucose-aptamer-FETs exhibited concentration-dependent responses to glucose (10 pM-10 nM). In control experiments, the FET responses to other monosaccharides, e.g., galactose and fructose, were minimal, as were responses when a scrambled glucose sequence was used (FIG. 4D). Experiments with SERS further corroborated target-specific recognition in close proximity to substrates for S1P and glucose aptamers (FIGS. 13E and 13F).

Figure 15:
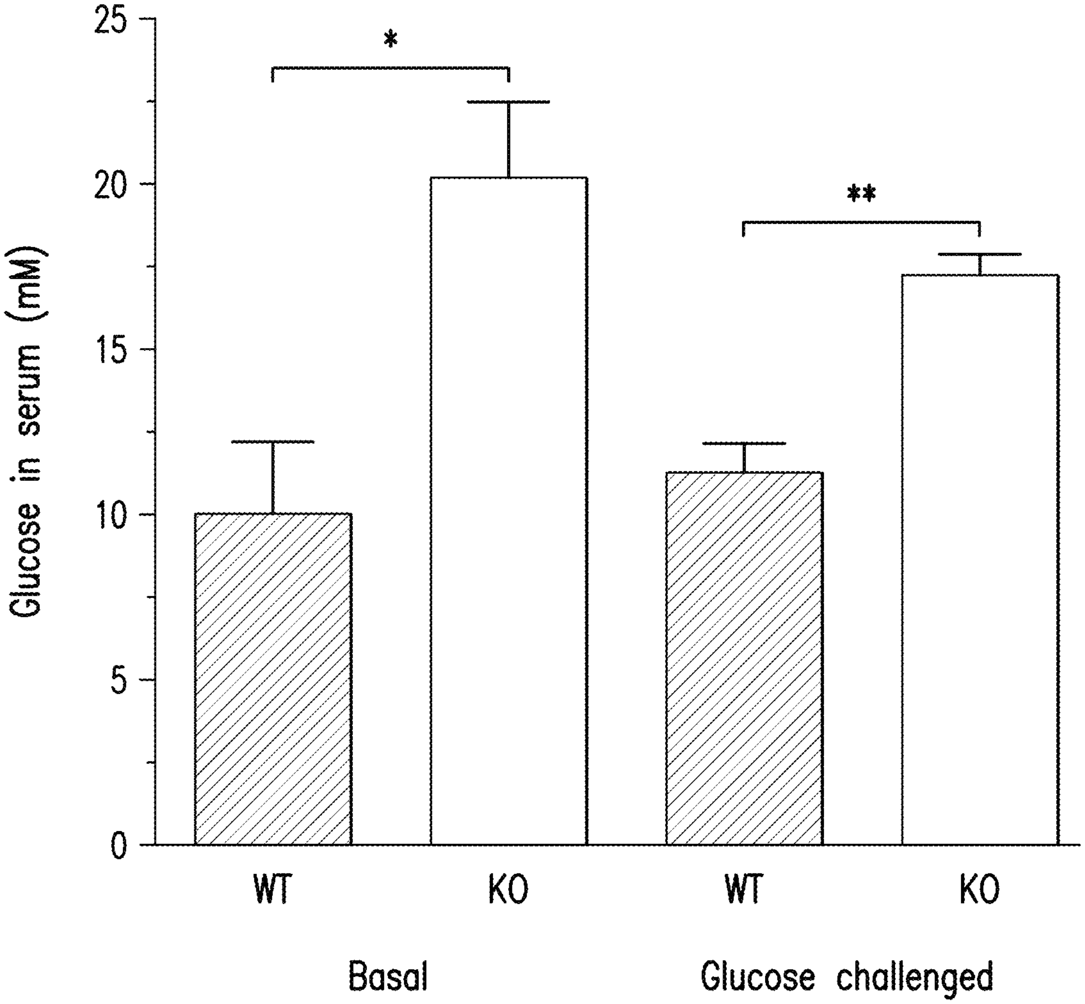
FIG. 15 provides glucometer measurements of glucose in whole blood at baseline (basal) and after glucose challenge. Hyperglycemia in serotonin transporter knockout mice and wildtype (normal) serum glucose levels can be measured and compared to glucose-aptamer-FET responses (FIG. 4F).

Glucose was detected in whole blood diluted with Ringer's buffer (10 μM-1 mM; FIG. 4E). Glucose levels were also measured in diluted serum from mice lacking serotonin transporter expression characterized by hyperglycemia. Elevations in serum glucose in basal and glucose-challenged states were observed using glucose-aptamer-FETs (FIG. 4F); glucose concentrations were similar to those determined in whole blood using a glucometer (FIG. 15). These findings demonstrate use of aptamer-FET sensing in diluted yet full ionic strength blood/serum and the ability to differentiate modest yet physiologically relevant differences in neutral target concentrations.

Aptamer-FET sensing enabled observations indicative of mechanism. In addition to FET behavior at a single sub-threshold-regime gate voltage, the characteristics of FET transfer-curves, i.e., source-drain currents ($I_{DS}$) vs. source-gate voltage sweeps ($V_{GS}$), were exampled. Transfer curves for increasing target concentrations diverged for dopamine- and glucose-aptamer-FETs vs. serotonin- and S1P-aptamer-FETs (FIG. 5A). Dopamine and serotonin each have a single positive charge at physiological pH. The observation of transfer curve divergence for these molecules alone suffices to conclude that signal transduction mechanisms based exclusively on target charge, as has been proposed, are incorrect and preclude detecting neutral targets. The divergence of curves suggests different conformational changes upon target binding. For dopamine and glucose, transfer curves are consistent with aptamer reorientations occurring such that a significant portion of the negatively charged backbone moves closer to the semiconductor channels, increasing electrostatic repulsion of charge carriers and decreasing transconductance, measured as target-related current responses (FIG. 5B). In contrast, serotonin and S1P aptamers move predominantly away from channel surfaces upon target capture increasing transconductance (FIG. 5C).

Figure 16B:
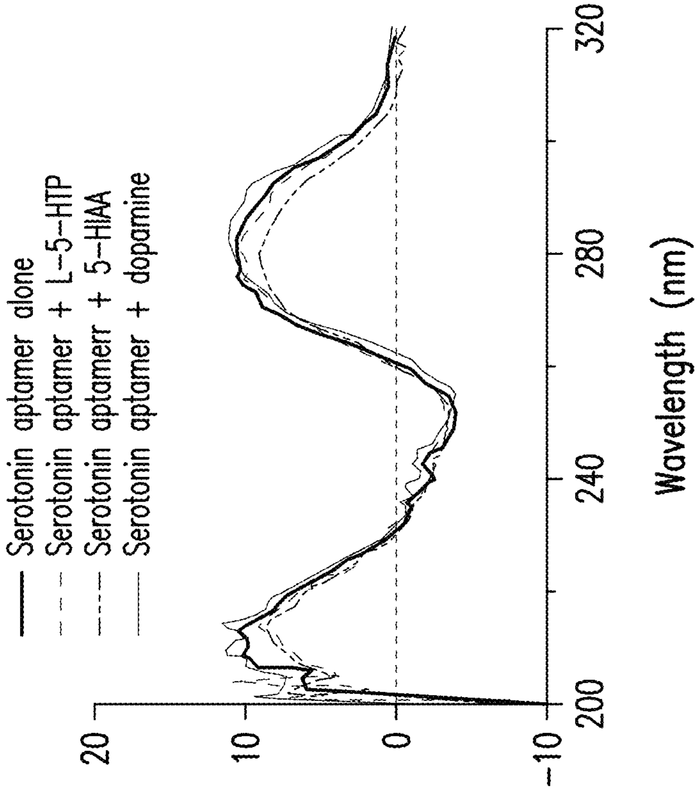
FIGS. 16A-B provides circular dichroism (CD) spectra showing minimal changes of the aptamer responses in the presence of nonspecific targets for (16A) dopamine aptamer and (16B) serotonin aptamer.
Figure 16A:
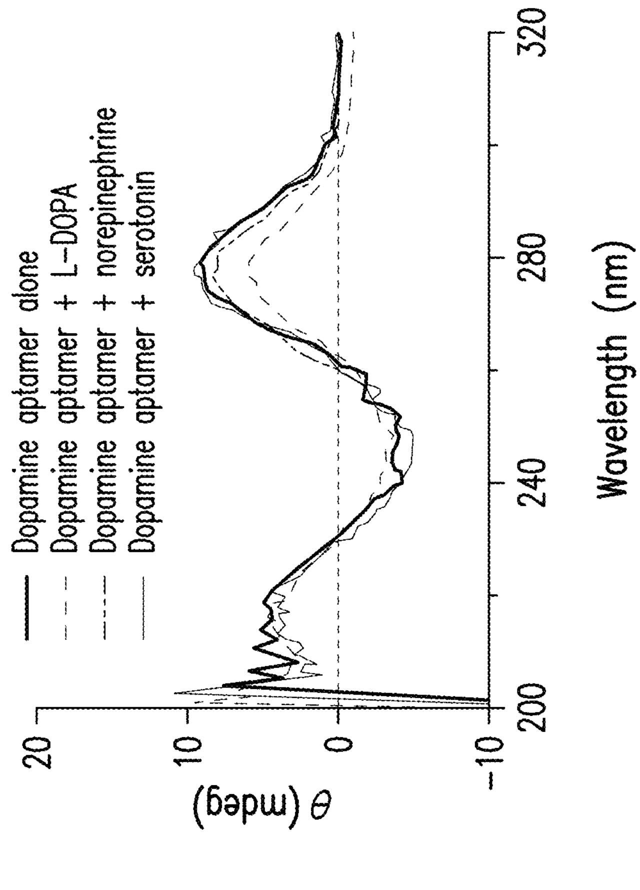
Figure 16C:
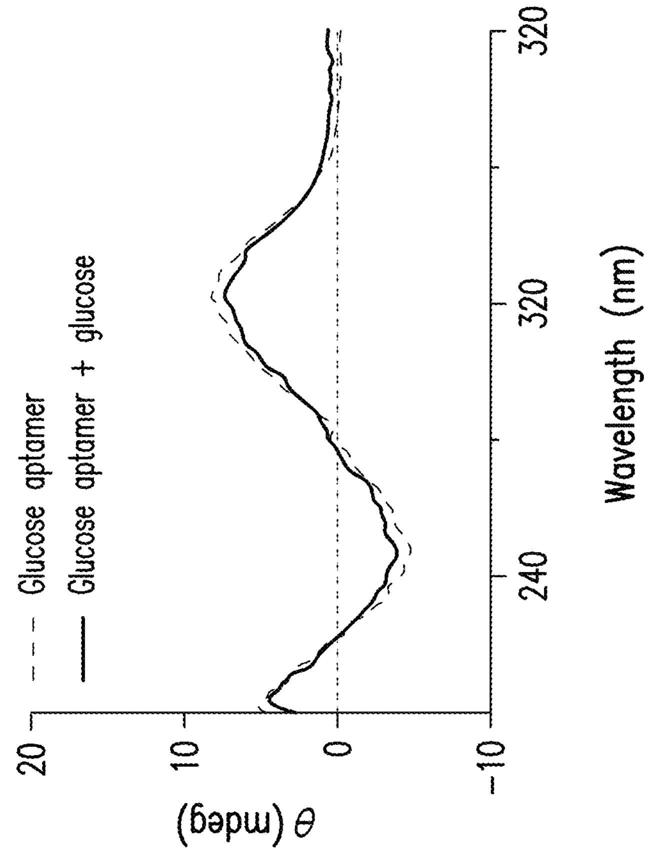
FIGS. 16C-D provides unchanged CD spectra upon correct target exposure for (16C) glucose aptamers and (16D) S1P aptamers, indicating that for certain aptamer types, secondary structural motifs can be preformed prior to target exposure and are not dependent on the presence of targets for formation.
Figure 16D:
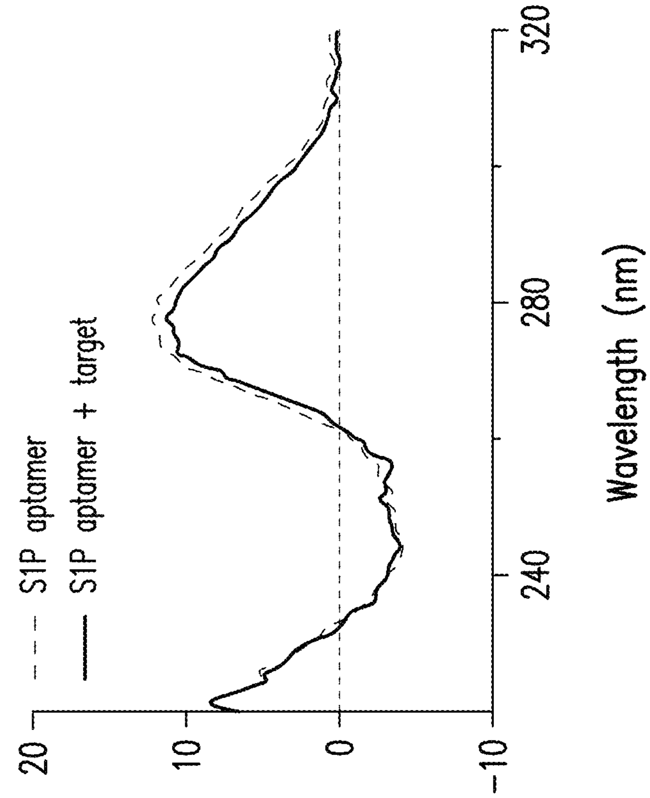

To gain additional mechanistic insight, circular dichroism (CD) spectroscopy was used. For dopamine and serotonin, large changes in CD peak positions and relative intensities indicated shifts away from predominant duplex signals (maxima at ~280 nm) and formation of new target-induced structural motifs. A parallel (or mixed) G-quadruplex (maximum shifted to 260 nm) was indicated for dopamine- (FIG. 6A) and an antiparallel G-quadruplex (maximum shifted to 290 nm) for serotonin-aptamer complexes (FIG. 6A). As with FET and SERS data, CD spectra indicated selectivity of dopamine and serotonin aptamers for their targets vs. similarly structured counter-targets (FIGS. 16A and 16B). While FET and SERS findings specified target recognition for glucose and S1P aptamers, changes in CD spectra were not observed for these aptamers (FIGS. 16C and 16D). Thus, for glucose and S1P aptamers, all major DNA domains, i.e., G-quartets, helices, and single-stranded regions, are formed prior to target binding and adaptive binding likely occurs through spatial rearrangement of existing secondary structures and companion ions.

Forester resonance energy transfer (FRET) was used to investigate changes in aptamer backbone distances during target-induced conformational changes. FRET sensors for serotonin and glucose were identified (Table 3). For serotonin, the decrease in FRET (FIGS. 6B and 17A) is consistent with a significant portion of the longest loop in the G-quadruplex moving away from the semiconductor surface, and hence, upward shifts in FET transfer curves (FIG. 5A). For glucose, FRET results (FIGS. 6B and 17B) unambiguously support movement of the second stem in the aptamer towards the semiconductor surface, consistent with downward shifts in FET transfer curves (FIG. 5A). For the glucose aptamer, the stem lengths for attachment to FET surfaces were increased (FIG. 6C). Conductance responses decreased with additional base pairs (FIG. 6D), indicating that recognition occurred further away from FETs as the attachment stems became longer. This strategy can also be used to tune sensitivity ranges of sensor array elements and thereby to extend the range of the array.

Together, all mechanistic findings are consistent with small-molecule-FETs enabling sensing under physiological conditions and without added aptamer labeling or surface chemistries. Because of the aptamer selection strategy, significant target-specific aptamer reorientations occur in close proximity to semiconductor surfaces, in some cases, even in the absence of formation of new secondary structural motifs. General reorientation can be inferred from FET gate-voltage sweeps. Unlike large protein receptors (e.g., antibodies), highly selective, chemically synthesized, compact nucleic acid receptors are identified through in vitro selection, and are amenable to affinity tuning and targeting of a wide variety of small (and large) molecules for electronic sensing.

Example 2—Monitoring Phenylalanine with Aptamer-Field-Effect Transistor Sensors This example illustrates the use of aptamer-field-effect transistors for sensing phenylalanine using target specific stem-loop aptamers.

Introduction

Figure 22A:
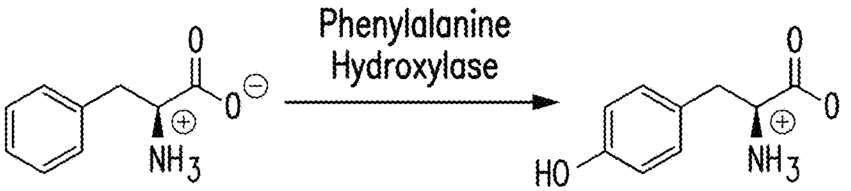
FIGS. 22A-E provide schematic illustrations and diagrams showing (22A) structure of phenylalanine (Phe) in human and mouse, (22B) structures of para-chlorophenylalanine (PCPA) and para-ethynylphenylalanine (PEPA), (22C) structure of phenylalanine-specific aptamer 1 (SEQ ID NO: 18) and its concentration-dependent response, (22D) structure of phenylalanine-specific aptamer 2 (SEQ ID NO: 16) and its concentration-dependent response, and (22E) structure of phenylalanine-specific aptamer 3 (SEQ ID NO: 22) and its concentration-dependent response.

Phenylketonuria (PKU) is an autosomal recessive genetic disorder involving mutations in the gene that encodes phenylalanine hydroxylase (PAH), which converts the essential amino acid phenylalanine to tyrosine (FIG. 22A). PKU can occur in one in 10,000-15,000 babies yearly. This so-called inborn error of metabolism can lead to hyperphenylalaninemia in the blood and brain. Elevated phenylalanine can cause abnormalities in brain development associated with permanent intellectual impairment. Screening newborns for PKU can involve laboratory testing by a bacterial inhibition assay, for example and without limitation, the Guthrie test, or more recently, tandem mass spectrometry. Although sufficient for diagnosis, these methods can have turnaround times of at least days to provide information to patients, families, and treatment providers.

Phenylketonuria is primarily managed through strict avoidance of phenylalanine-containing foods. Early-life dietary management can prevent the damaging effects of PKU on brain development. However, even modestly uncontrolled blood phenylalanine levels in children and adults can be correlated with neurocognitive and psychiatric sequelae. PKU treatment guidelines can provide for blood phenylalanine levels to be maintained between 120 to 360 μM; phenylalanine concentrations in healthy individuals can be 60±30 μM. Moderate hyperphenylalaninemia can be associated with blood levels ranging from 360 to 600 μM, while untreated PKU can be characterized by phenylalanine levels >1000 μM (with concentrations >3000 μM having been reported).

Emerging treatments for PKU can be based on enzyme substitution with pegylated versions of bacterial phenylalanine ammonia lyase. Enzyme substitution, for example and without limitation using an enzyme substitution therapy, such as pegvaliase (Palynziq™), can decrease phenylalanine levels in patients with PKU and reduce the need for dietary restrictions, which can be difficult to maintain over a lifetime. As such, real-time phenylalanine monitoring can provide insights into the pharmacokinetics and efficacy of current and future PKU treatment strategies. Allowing patients to determine their blood phenylalanine levels, including hypophenylalaninemia associated with enzyme replacement therapies, can be advantageous for long-term PKU management. Point-of-care or at-home options for measuring blood phenylalanine can thus effectively improve diabetes management and patient agency.

Field-effect transistors (FETs) can be modified with protein receptors. Receptor recognition of charged targets and/or target-induced receptor reorientation can gate the semiconductor channels to modulate transconductance. Certain BioFETs based on protein receptors or antibodies can be unsuitable for direct sensing in biological fluids at least in part because these large receptors (e.g., ~10 nm) can be too far away from the semiconductor channel relative to the screening length. At physiological ion concentrations, this so-called Debye length can be on the order of 1 nm. Aptamer-FETs can provide sensitive and selective detection of small molecules, included neutral targets, in physiological buffers and fluids, and complex biological matrices.

In this example, previously unreported phenylalanine aptamers were coupled with nanometer-thin $In_2O_3$ FETs. Phenylalanine was detected over many orders of magnitude (fM mM) in physiological solution. Selectivity for phenylalanine over closely structured endogenous and exogenous (FIG. 22B) aromatic amino acid analogs and metabolites was improved, including for one of the phenylalanine aptamers. Phenylalanine sensing was carried out in serum from mice with induced hyperphenylalaninemia, demonstrating the ability of aptamer-FETs to detect biologically important differences in phenylalanine concentrations. In this manner, as embodied herein, aptamer-functionalized FETs can be used in devices for point-of-care phenylalanine monitoring in PKU patients and other relevant populations.

Materials and Method

The amino acids used throughout were the L-forms, e.g., L-phenylalanine, L-tyrosine, and L-tryptophan. Oligonucleotides were obtained from Integrated DNA Technologies. The SYLGARD 184 used to make polydimethylsiloxane (PDMS) wells was from Dow Corning Corporation. Water was deionized before use (18.2 MΩ) with a Milli-Q system. para-Ethynylphenylalanine (PEPA) was synthesized. Trimethylsilyl acetylene was coupled under palladium catalysis to to N acetyl 4 iodophenylalanine methyl ester, followed by deprotection and purification. The nuclear magnetic resonance spectroscopy (NMR) data matched spectra reported in the literature (Figure S9).

Phenylalanine Aptamer Selection

Figure 25B:
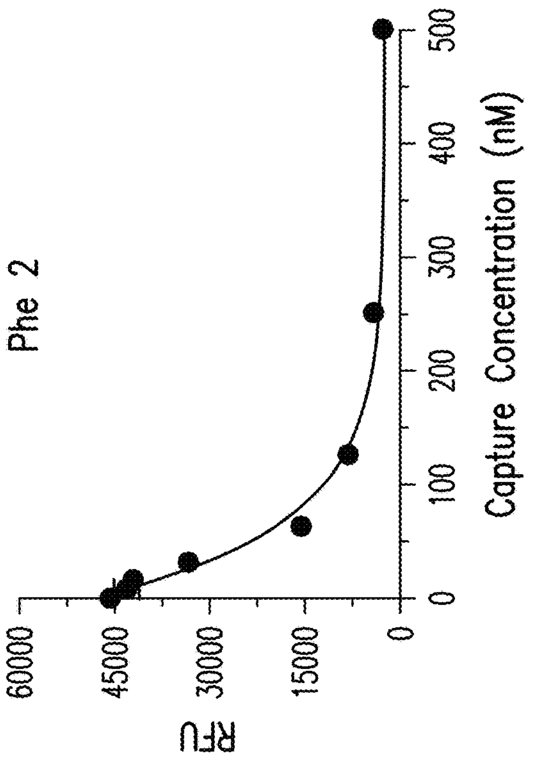
FIGS. 25A-C provide diagrams illustrating example fluorescence quenching curves of (25A) the Phe 1 aptamer, (25B) the Phe 2 aptamer, and (25C) the Phe 3 aptamer.
Figure 25A:
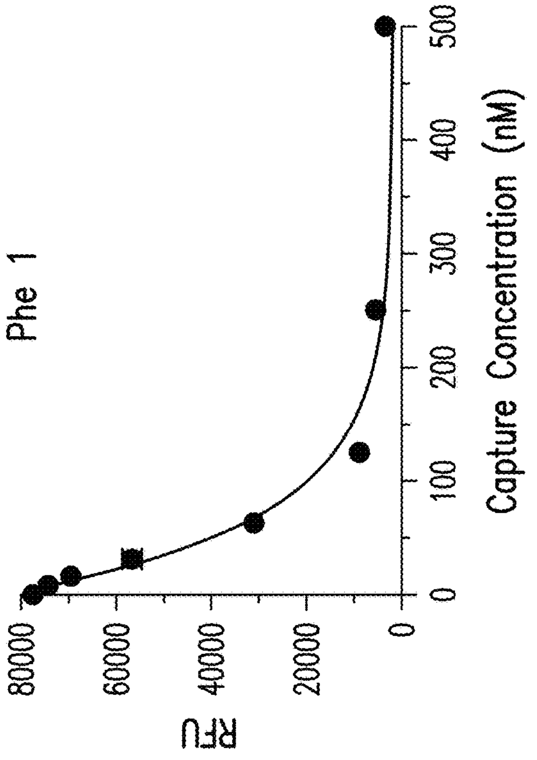
Figure 25C:
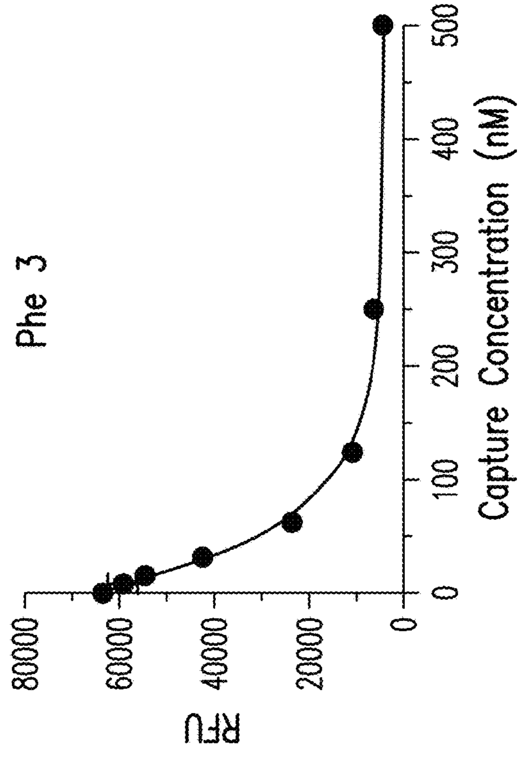
Figure 26A:
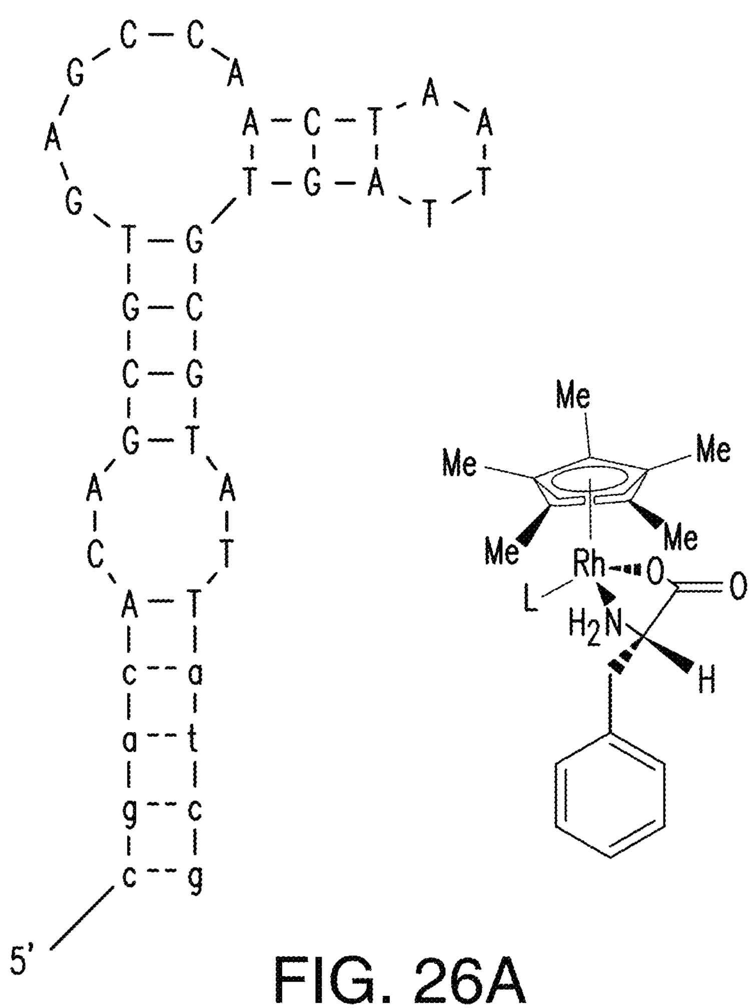
FIGS. 26A-D provide diagrams illustrating (26A) an example aptamer sequence (SEQ ID NO: 98) isolated for specificity for Phe-Cp*Rh, (26B) an example quenching curve for Phe-Cp*Rh 2, (26C) fluorescence concentration curves of Phe-Cp*Rh, Trp-Cp*Rh, and Tyr-Cp*Rh, and (26D) calibrated responses of the disclosed field-effect transistor sensing device using Phe-Cp*Rh 2.
Figure 26B:
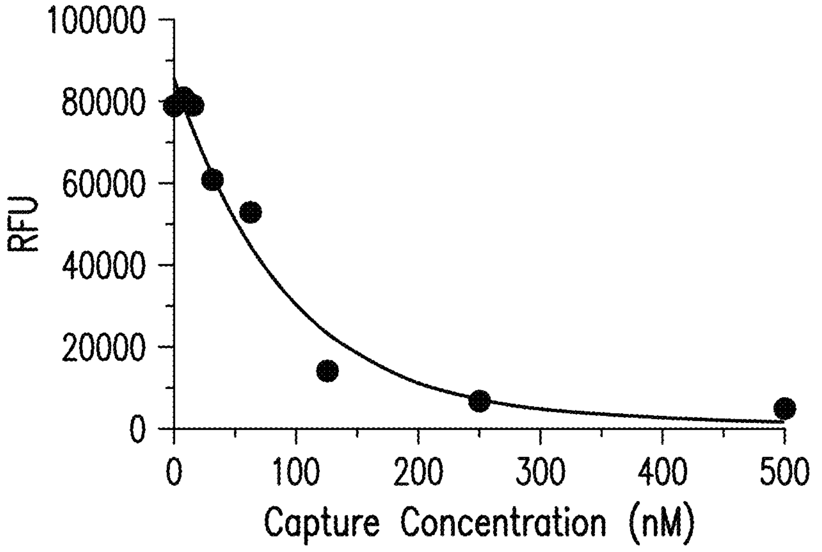
Figure 26D:
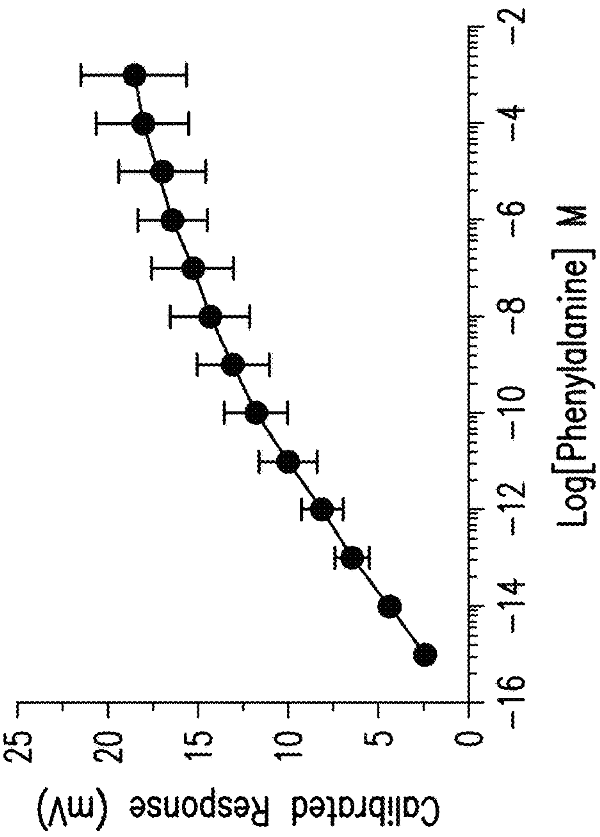
Figure 26C:
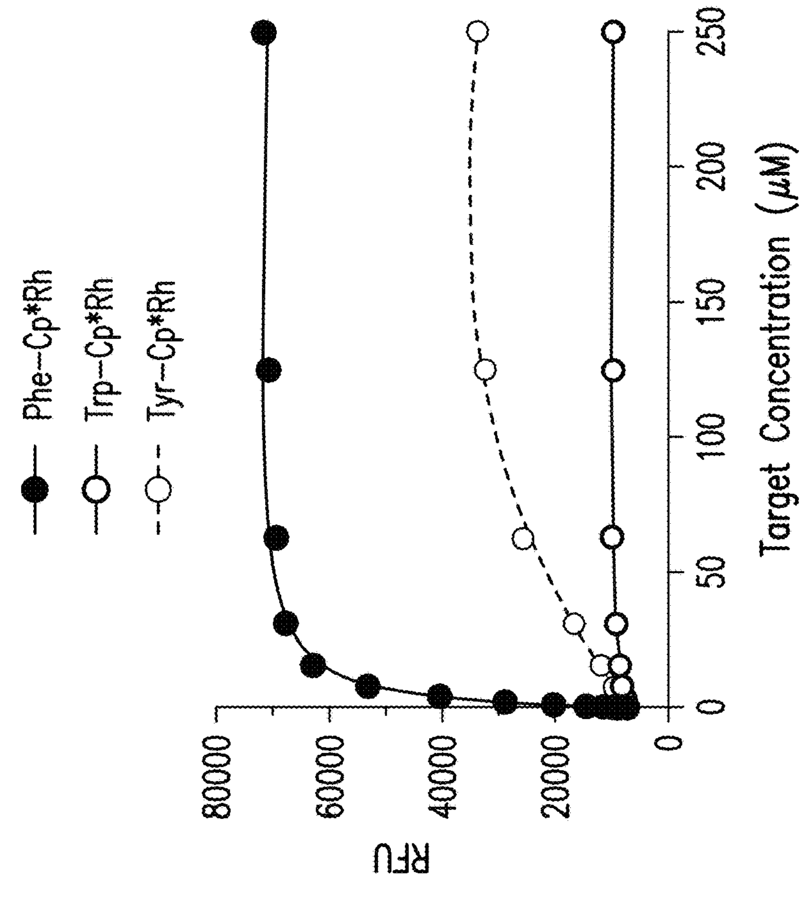

Phenylalanine aptamer selection was performed. Initial selection resulted in isolation of an aptamer for phenylalanine complexed with pentamethylcyclopentadienyl rhodium (III) (Cp*Rh). This aptamer, which was designated Phe-Cp*Rh 1, showed cross-reactivity with the analogous tryptophan-Cp*Rh complex (Trp-Cp*Rh). To reduce cross-reactivity, additional selections for Phe-Cp*Rh were performed with Trp-Cp*Rh counter-selection, which resulted in the isolation of two new Phe-Cp*Rh aptamers, which were designated Phe-Cp*Rh 2 and Phe-Cp*Rh 3 (Table 10). These Phe-Cp*Rh aptamers were not cross-reactive with Trp-Cp*Rh (FIGS. 25 and 26). However, Phe-Cp*Rh 2 showed cross reactivity with Tyr-Cp*Rh (FIG. 26C).

Figure 34:
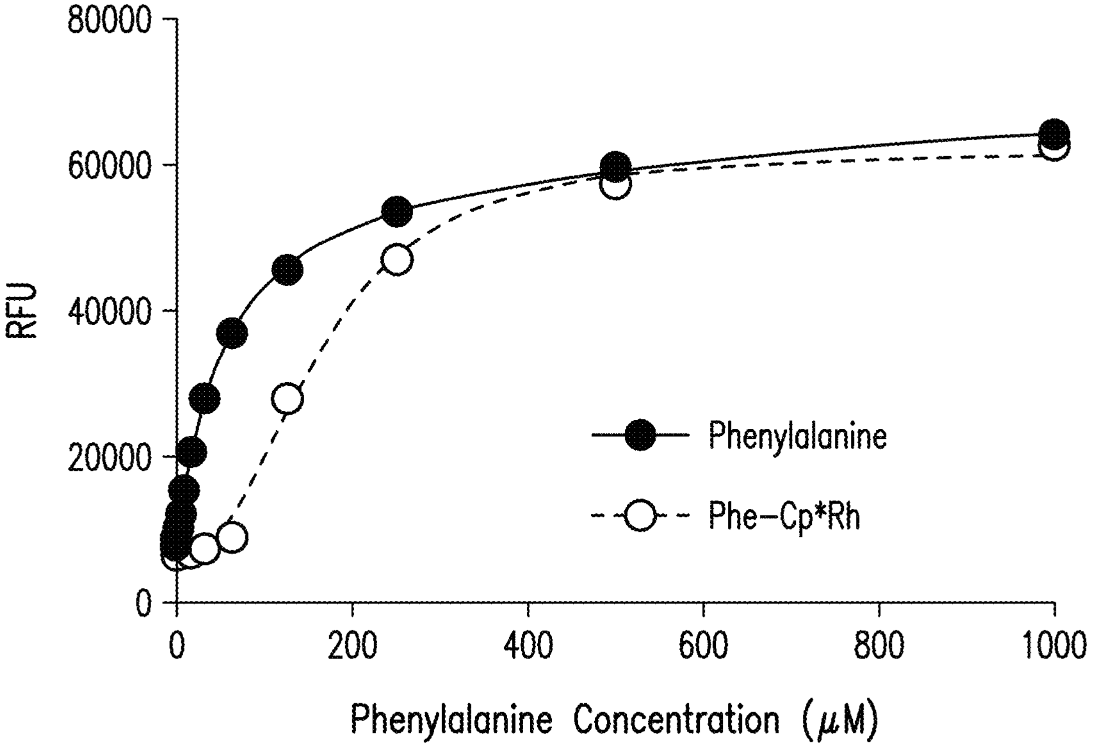
FIG. 34 provides a diagram illustrating competitive fluorescence curves of Phe 1 upon exposure to free phenylalanine vs. coincubation with an excess of phenylalanine in combination with the organometallic complex (Cp*Rh) to form Phe-Cp*Rh+free phenylalanine.

As byproducts of the selections for additional Phe-Cp*Rh aptamers, three aptamers that recognize phenylalanine, rather than the Phe-Cp*Rh complex, were obtained. These direct-binding aptamers were designated Phe 1, Phe 2, and Phe 3 (Table 10). An excess of phenylalanine (1 mM) was used in the selection procedures to produce the Phe-Cp*Rh complex such that the Cp*Rh was consumed. Under these conditions, a large excess of free phenylalanine, which also interacted with the oligonucleotide sequences, was present along with the Phe-Cp*Rh complex in the target solutions. The responses of Phe 1 were compared to phenylalanine with and without Cp*Rh (FIG. 34). In the presence of Cp*Rh, phenylalanine prefers to complex with Cp*Rh, however the remaining free phenylalanine in solution was detected by Phe 1.

Fluorescence assays were carried out in 20 mM HEPES, 1 M NaCl, 10 nM $MgCl_2$, and 5 mM KCl (pH 7.5). Each aptamer sequence was modified with fluorescein at the 5' end. Complementary strands were 3'-modified with dabcyl for solution quenching determination of dissociation constants (Kd) (Table 10) and for selectivity testing. Concentrations of aptamers and complementary strands were empirically determined and aptamer Kd values were calculated.

TABLE 10

Sequences of aptamers and associated complementary (capture) strands used for competitive fluorescence assays.

| Aptamer | Strand | Sequence (5'→3') |
|---|---|---|
| Phe 1 | Sensor | /56-FAM/CTC TCG GGA CGA CCG CGT TTC CCA AGA AAG CAA GTA TTG GTT GGT CGT CCC (SEQ ID NO: 13) |
| | Capture | GGT CGT CCC GAG AG/3Dab/ (SEQ ID NO: 81) |
| Phe 2 | Sensor | /56-FAM/CTC TCG GGA CGA CCG GTG GGG GTT CTT TTT CAG GGG AGG TAC GGT CGT CCC (SEQ ID NO: 14) |
| | Capture | GTC GTC CCG AGA G/3Dab/ (SEQ ID NO: 80) |
| Phe 3 | Sensor | /56-FAM/CTC TCG GGA CGA CGA GGC TGG ATG CAT TCG CCG GAT GTT CGA TGT CGT CCC (SEQ ID NO: 15) |
| | Capture | GTC GTC CCG AGA G/3Dab/ (SEQ ID NO: 80) |
| Phe-Cp*Rh 2 | Sensor | /56-FAM/CTC TCG GGA CGA CAC AGC GTG AGC CAA CTA ATT AGT GCG TAT TGT TCG TCC C (SEQ ID NO: 86) |
| | Capture | TGT CGT CCC GAG AG/3Dab/ (SEQ ID NO: 87) |
| Phe-Cp*Rh 3 | Sensor | /56-FAM/CTC TCG GGA CGA CCA CGG GAT ATC TTC AGG ATG GTG GTA ACT GGT CGT CCC (SEQ ID NO: 88) |
| | Capture | GGT CGT CCC GAG AG/3Dab/ (SEQ ID NO: 81) |

Aptamer-Functionalized Field-Effect Transistors

Field-effect transistors were fabricated using about 4 nm $In_2O_3$ semiconductor films as channel materials with high surface-to-volume ratios. Aqueous solutions (0.1 M) of indium(III) nitrate hydrate ($In(NO_3)_3 x \cdot H_2O$, 99.999%) were spin-coated at 3000 rpm for 30 s onto heavily doped silicon wafers with 100-nm thermally grown oxide layers. After coating, substrates were pre-heated at 150° C. for 10 min followed by 3 h of annealing at 350° C. Source and drain electrodes (10 nm Ti/30 nm Au) were deposited by electron-beam evaporation and patterned via standard photolithography.

To functionalize thin-film FETs with thiolated phenylalanine aptamers, mixed monolayers of (3 aminopropyl)trimethoxysilane and trimethoxy(propyl)silane (1:9 v/v ratio) using vapor-phase deposition on $In_2O_3$ surfaces were self-assembled at 40° C. for 1 h. Substrates were then incubated with a 1 mM ethanolic solution of 1 dodecanethiol for 1 h to passivate Au electrodes via alkanethiol monolayer formation. After rinsing with ethanol, substrates were incubated with a 1 mM solution of 3 maleimidobenzoic acid N hydroxysuccinimide ester (MBS) in 1:9 (v/v) dimethyl sulfoxide and phosphate-buffered saline (1×PBS, pH 7.4) for 30 min. Thiolated DNA aptamers (Table 11) were diluted to 1 pM in nuclease-free water and heated for 5 min at 95° C. followed by rapid cooling in an ice bath. Substrates were then immersed in aptamer solutions for 24 h, rinsed with deionized water, and dried under N2 gas.

A scrambled aptamer sequence for Phe 3 was designed using mfold to have a secondary structure that was predicted to differ from the correct phenylalanine aptamer sequence, while maintaining the same numbers and types of nucleotides (Table 11).

Field-Effect Transistor Measurements:

TABLE 11

Sequences of thiolated, shortened aptamers used for field-effect transistor measurements.

| Aptamer | Strand | Sequence (5'→3') |
|---|---|---|
| Phe 1 | Short | /5ThioMC6-D/GA CCG CGT TTC CCA AGA AAG CAA GTA TTG GTT GGT C (SEQ ID NO: 18) |
| Phe 2 | Short | /5ThioMC6-D/GA CCG GTG GGG GTT CTT TTT CAG GGG AGG TAC GGT C (SEQ ID NO: 16) |
| Phe 3 | Short | /5ThioMC6-D/CGA CGA GGC TGG ATG CAT TCG CCG GAT GTT CGA TGT CG (SEQ ID NO: 22) |
| | Scrambled | /5ThioMC6-D/ATT GCT ATT CAC CGG CGC GGG GCT GGG GCA TCG GTA AT (SEQ ID NO: 89) |
| Phe-Cp*Rh 2 | Short | /5ThioMC6-D/CGA CAC AGC GTG AGC CAA CTA ATT AGT GCG TAT TGT CG (SEQ ID NO: 90) |

Figure 35:
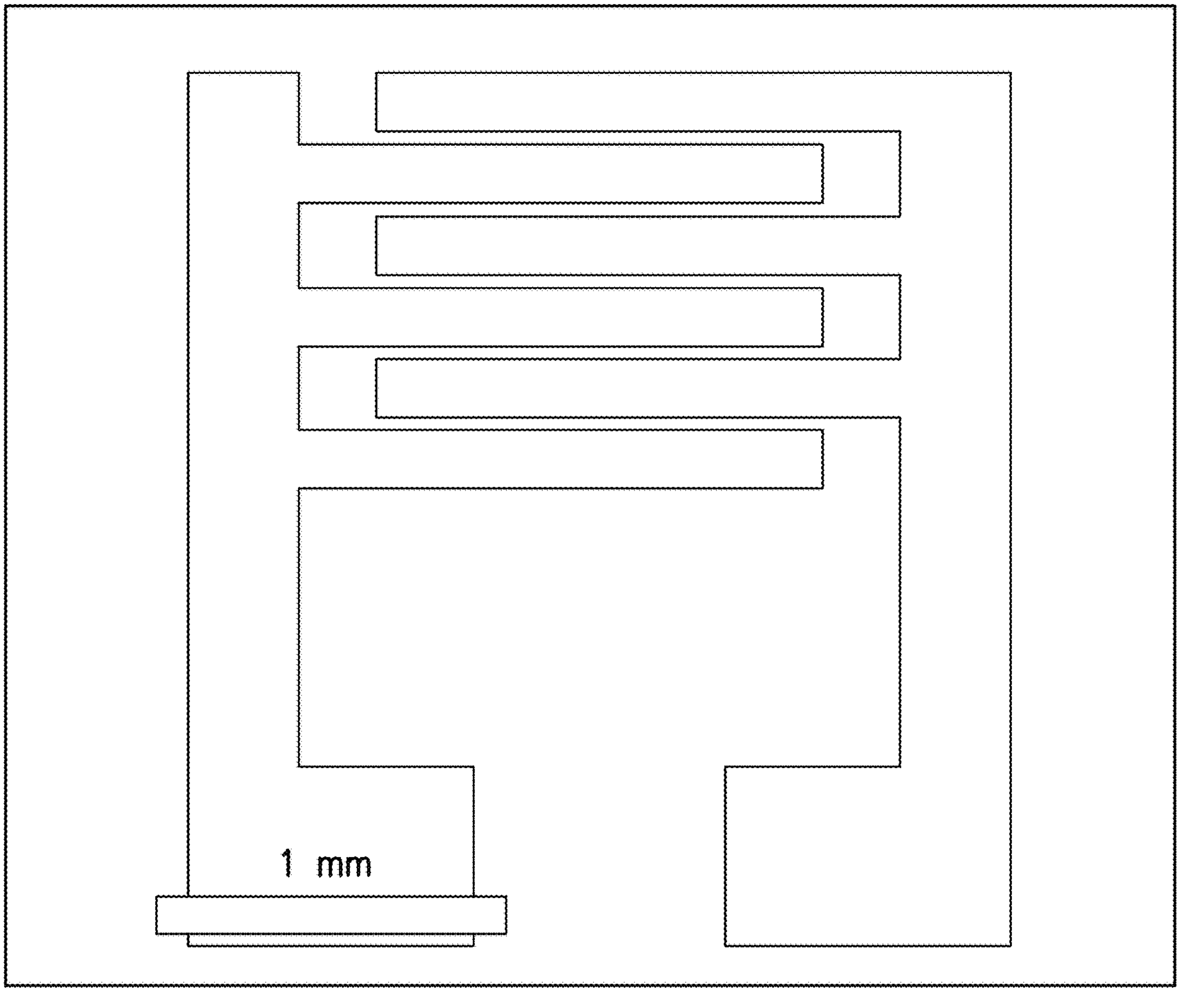
FIG. 35 provides an example optical microscopy image of a field-effect transistor (FET).

Polydimethylsiloxane wells were sealed on individual FETs to hold sensing solutions. Substrates had inter-FET distances (for example and without limitation, about 2 mm) large enough to allow isolation of single FET devices within the PDMS wells (FIG. 35). Ringer's solution (NaCl 147 mM, KCl 4 mM, $CaCl_2$ 2.25 mM) was used as the electrolyte solution. The Ag/AgCl reference electrodes were placed in sensing solutions in a top-gate (solution-gate) device configuration. Measurements here were performed using a manual analytical probe station equipped with a Keithley 4200A-SCS semiconductor parameter analyzer.

Source-drain current ($I_{DS}$) transfer curves were obtained by varying gate voltages ($V_{GS}$) from 0 to 400 mV with a step voltage of 5 mV. The drain voltage (VD) was held at 10 mV throughout. Five sweeps were averaged for each transfer curve. Calibrated responses were calculated by dividing the absolute sensor response (ΔI), which takes into account baseline subtraction, by the change in source-drain current with voltage sweep ($\Delta I_{DS}/\Delta_{VG}$). 89 Aptamer-FET responses at VG=375 mV were used to calculate mean calibrated responses.

Mouse Serum

Mice were generated from a core colony of a serotonin transporter (SERT)-deficient lineage maintained on a mixed CD1×129S6/SvEv background via heterozygous SERT-deficient (SERT+/−) pairings. In this example, three pairs of SERT wildtype (SERT+/+) mice from the core colony were bred to produce 18 wildtype pups. All mice were maintained on a 12-h light/dark cycle (lights on at 0600 h) with ad libitum food and water.

For postnatal treatment, pups from each litter were randomly assigned to one of three groups: (1) Saline (vehicle control); (2) 100 mg/kg para-chlorophenylalanine; or (3) 10 mg/kg para-ethynylphenylalanine. Doses were calculated based on the free base form of each compound. The pH values of PEPA and PCPA saline were adjusted to pH 7.4 prior to injection. Each litter contained all treatment groups. Each pup received a subcutaneous injection of the assigned treatment daily during ZT 6-8 on postnatal days (P)4 21. The injection volume was 10 mL/kg during P4-11, and 5 mL/kg during P12-21. A total of three of the 18 pups were excluded from this study: ⅙ saline-treated and ⅙ PCPA-treated subjects died during the postnatal period. In addition, ⅙ PEPA-treated subjects stopped receiving injections at P17 due to body weight loss for more than two continuous days. The data from the remaining N=5 mice per treatment group are reported.

Pups were weaned after the last injection on P21 and housed with their siblings. Two hours after the last injection, subjects were euthanized by decapitation under deep anesthesia with isoflurane. Whole blood samples were collected via cardiac puncture and placed in microcentrifuge tubes pre-chilled on ice for 30, 60 min. Following coagulation, blood samples were centrifuged at 16,000 g for 15 min at 4° C. twice. After each centrifugation, supernatants were removed and transferred to clean microcentrifuge tubes on ice. Serum samples were aliquoted and stored at 80° C. until analysis. Aptamer-FET and high-performance liquid chromatography (HPLC) measurements were carried out by investigators blind to the treatment group identification of each sample. Serum samples for aptamer-FET measurements were diluted to about 10 μM phenylalanine in 1×Ringer's buffer based on average phenylalanine concentrations determined by HPLC.

Circular Dichroism Spectroscopy

Intensities and positions of positive and negative peaks for oligonucleotides in circular dichroism (CD) spectra correspond to exciton interactions induced by stacking of hydrophobic bases in asymmetric helices. Aptamer and target concentrations were 2 μM in 1×Ringer's buffer. Thiolated aptamers were heated at 95° C. for 5 min and cooled to room temperature slowly to relax DNA molecules into extended conformations. Spectra were collected using a JASCO J 715 circular dichroism spectrophotometer. Four scans with 0.5-nm resolution, 1.0-nm bandwidth, a 4-s response time, and a 20 nm/min scan rate were acquired per sample. Scans of 1×Ringers solution were subtracted as background.

High-Performance Liquid Chromatography

A modified o-phthalaldehyde-sulfite (OPA-S) method was used to analyze phenylalanine in serum samples. On the day of analysis, 0.1 M perchloric acid was freshly prepared, protected from light, and stored on ice. A series of 11 phenylalanine standards (0-50 μM) were prepared in 0.1 M perchloric acid to establish standard curves. Solutions for phenylalanine analysis via the OPA-S method included neutralization solution (0.4 M boric acid (Sigma #31144), pH 10.4 10.5) and derivatization solution (14.9 mM phthaldialdehyde (OPA), 47.6 mM sodium sulfite, and 5% methanol in 0.36 M boric acid, pH 10.4 10.5), which were prepared the day of analysis about 1 h before use and protected from light.

Serum samples were removed from a −80° C. freezer and thawed on wet ice. 168 μL of ice-cold 0.1 M perchloric acid solution was added to 7 μL of each serum sample. Samples were briefly vortexed and centrifuged at 16,000 g at 4° C. for 15 min two times. After each centrifugation, supernatants were removed and transferred to clean microcentrifuge tubes on ice.

For derivatization, 50 μL each of the phenylalanine standard solutions and serum samples were neutralized with 50 μL of neutralization solution at room temperature in black microcentrifuge tubes, followed by addition of 50 μL of derivatization solution. The derivatization reaction was allowed to proceed for 10 min in the dark. Derivatization was stopped by adding 500 μL of the mobile phase (0.2 M phosphate buffer, pH 4.8, with 0.13 mM EDTA in 25% MeOH in deionized water) to each sample. Derivatized samples and standards were immediately analyzed by HPLC with electrochemical detection. The instrument was an Eicom integrated HPLC system (HTEC 500) that included an Insight Autosampler. Electrochemical detection occurred at a pure graphite working electrode (WE PG) at an optimized applied potential of +650 mV vs. Ag/AgCl. The stationary phase was a Phenomenex Kinetex column (2.6 μm particle size, 3.0 mm ID×10 mm). Separation occurred at a flow rate of 350 μL/min. The column temperature was maintained at 30° C. The retention time of phenylalanine was about 22 min.

Statistics

In this example, data for fluorescence assays and FET calibrated responses are reported as means±standard errors of the means and were analyzed using GraphPad Prism 7.04 via one-way analysis of variance followed by Tukey's multiple comparisons post hoc tests. Cross-validation data for phenylalanine levels were analyzed by linear regression analysis, and $P<0.05$ was considered statistically significant.

Results and Discussion

Figure 22B:
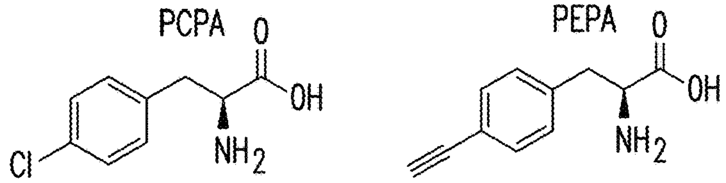
Figure 22C:
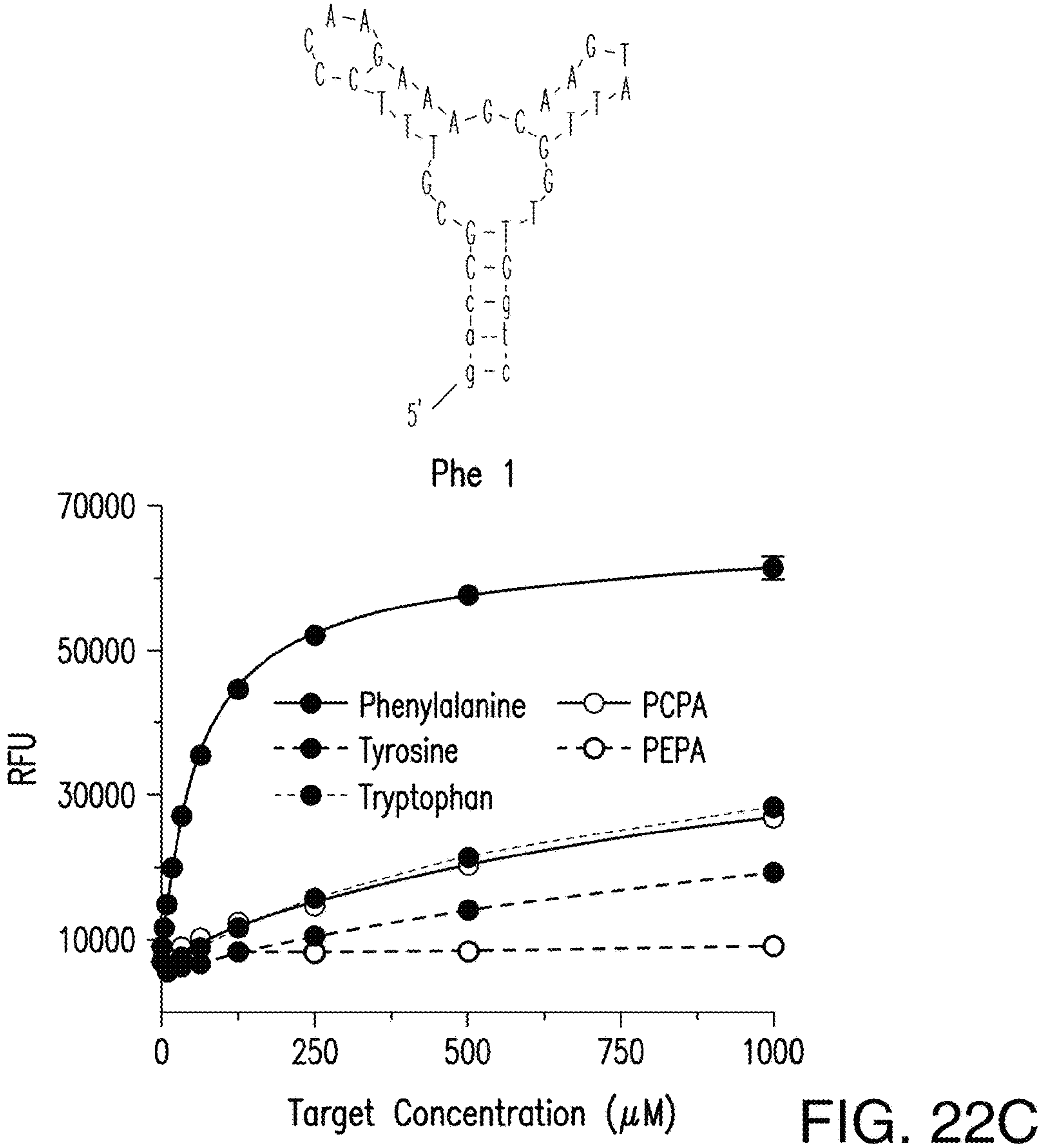
Figure 22D:
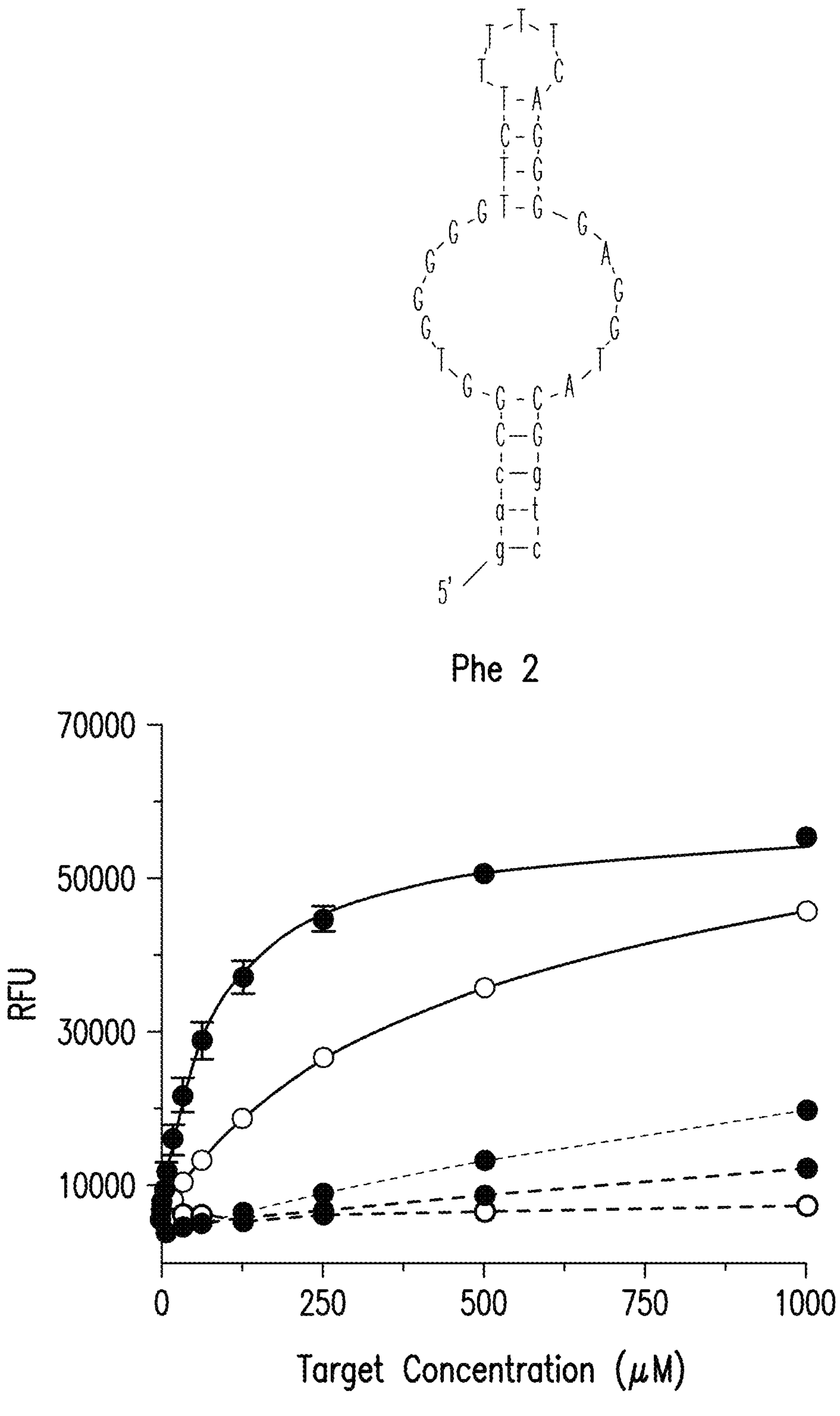
Figure 22E:
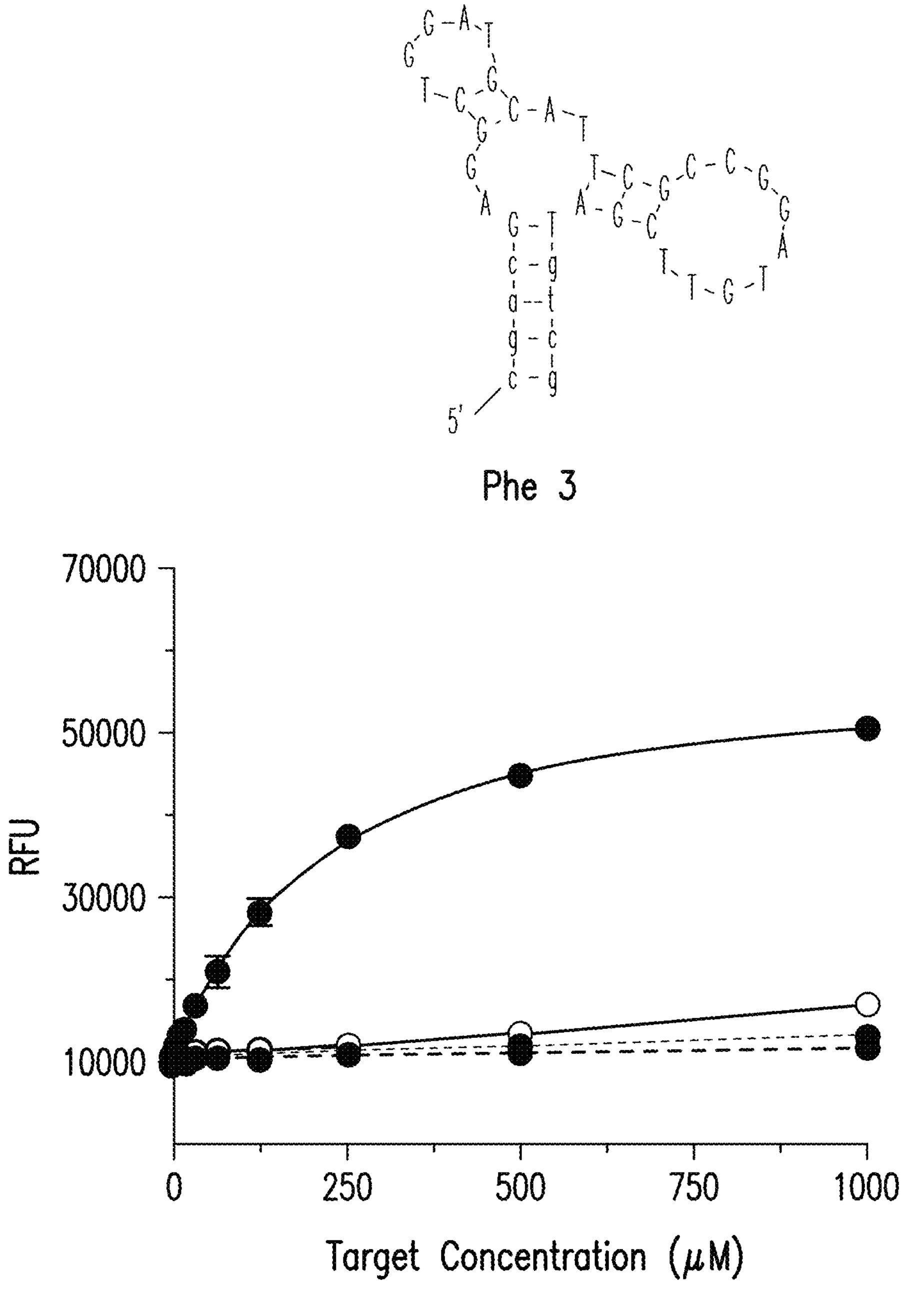

Three DNA aptamer sequences that recognize the amino acid phenylalanine were identified via solution-phase, in vitro systematic evolution of ligands by exponential enrichment (SELEX) (as shown for example in FIG. 22C-E and described herein). Dissociation constants were determined using competitive fluorescence assays. Quencher-labeled complementary sequences were displaced from fluorescently labeled aptamer sequences upon phenylalanine binding resulting in increases in fluorescence intensities, as shown for example in FIGS. 22C-E and 25. Solution dissociation constants (Kd) were 10 pM, 7 μM, and 16 μM for Phe 1, Phe 2, and Phe 3, respectively.

Figure 27:
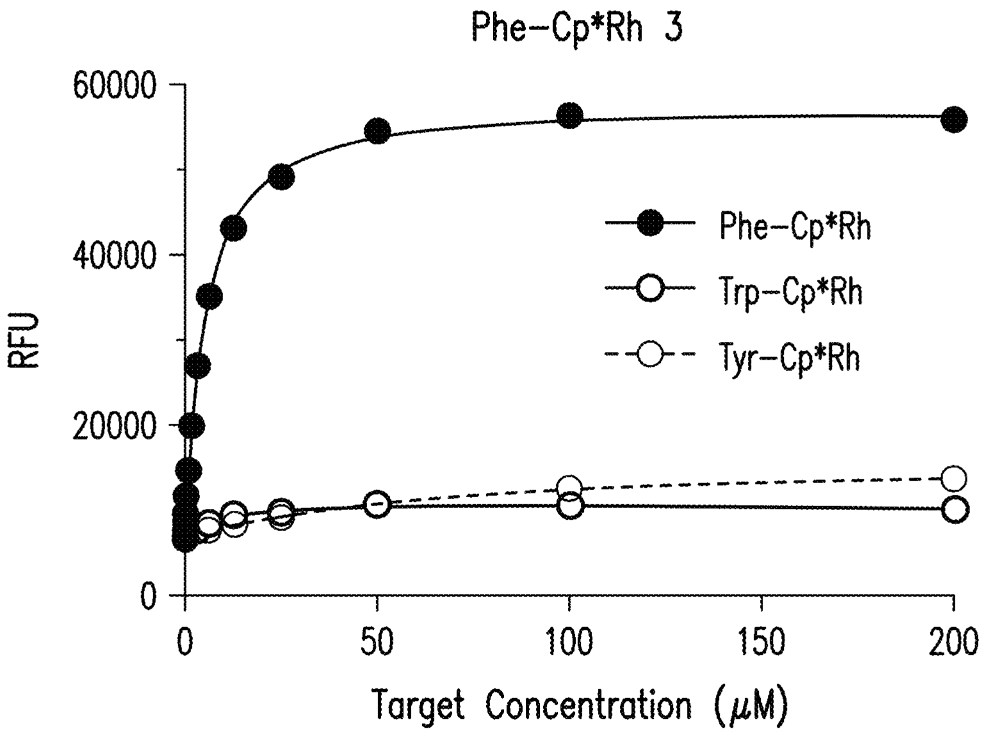
FIG. 27 provides a diagram illustrating competitive fluorescence curves of Phe-Cp*Rh, Trp-Cp*Rh, and Tyr-Cp*Rh.

Selections initially had been carried out using a strategy to increase aptamer selectivity towards low epitope targets by associating targets with metal complexes. In addition to a previously reported aptamer sequence recognizing phenylalanine complexed with pentamethylcyclopentadienyl rhodium(III) (Cp*Rh) (sequence herein referred to as Phe-Cp*Rh 1), two previously unreported sequences, Phe-Cp*Rh 2 and Phe-Cp*Rh 3, were also characterized (FIGS. 26 and 27). FIG. 26A shows an aptamer sequence (left) isolated for specificity for Phe-Cp*Rh (right). FIG. 26B shows quenching curve for Phe-Cp*Rh 2. FIG. 27C shows results of competitive fluorescence assay to investigate selectivity of Phe-Cp*Rh 2. A solution Kd of ~0.8 μM was determined from the fluorescence concentration curve. FIG. 27D shows results of field-effect transistor sensing using Phe-Cp*Rh 2 demonstrated responses over a wide range of concentrations (fM mM). For B, C, and D, N=3 with error bars representing standard errors of the means, which are smaller than the data points shown in B and C; RFU is relative fluorescence units.

Figures 28A, 28B, 28C:
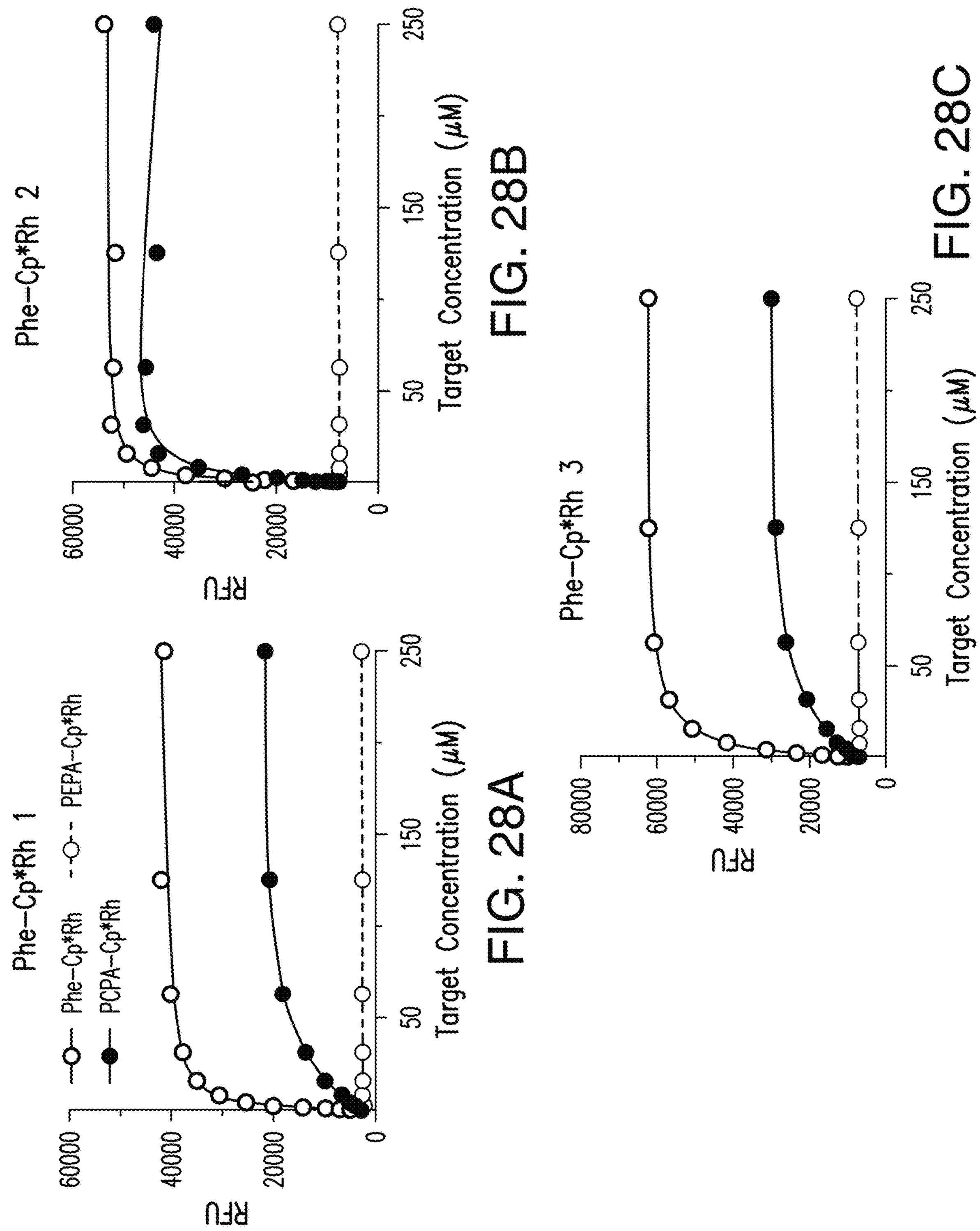
FIGS. 28A-C provide diagrams illustrating selectivity data for (28A) Phe-Cp*Rh 1, (28B) Phe-Cp*Rh 2, and (28C) Phe-Cp*Rh 3 aptamers via competitive fluorescence assays towards para-chlorophenylalanine (PCPA) or para-ethynylphenylalanine (PEPA).

Selectivity testing for the three direct-detection phenylalanine aptamers using competitive florescence assays showed reduced (Phe 1 and Phe 2) or negligible (Phe 3) responses towards the endogenous aromatic amino acids tyrosine and tryptophan (FIG. 22C-E). Selectivity of phenylalanine aptamers for two phenylalanine analogs, para-chlorophenylalanine (PCPA) and para-ethynylphenylalanine (PEPA) was studied (FIG. 22B), which potentially induce hyperphenylalaninemia in animal models. The Phe 3 aptamer showed minimal responses to PCPA or PEPA via competitive fluorescence assays (FIG. 22E), in contrast to Phe 1, Phe 2, and the Phe-Cp*Rh aptamers, which all had appreciable responses to PCPA (FIGS. 22C-D and 28). All three aptamers showed varying degrees of cross-reactivity with PCPA and minimal responses to PEPA. For A-C, N=3 with error bars representing standard errors of the means, which are smaller than the data points shown; RFU is relative fluorescence units.

As shown in FIG. 22A, in humans and mice, phenylalanine is para-hydroxylated to form tyrosine by the liver enzyme phenylalanine hydroxylase (PAH). The genetic disorder phenylketonuria can be caused by mutations in the PAH gene, which can result in high blood and brain levels of phenylalanine. FIG. 22B shows phenylalanine analogs para-chlorophenylalanine (PCPA) and para-ethynylphenylalanine (PEPA). FIGS. 22C-D show three phenylalanine-specific aptamer sequences (Phe 1, Phe 2, and Phe 3) that were isolated for sensor development. All three aptamers showed concentration-dependent responses towards phenylalanine determined via competitive fluorescence assays. Responses were measured for other aromatic amino acids (tyrosine and tryptophan) and the phenylalanine analogs (PCPA and PEPA). Fluorescence concentration curves enabled determination of solution dissociation constants (Kd) for Phe 1 (10 μM), Phe 2 (7 μM), and Phe 3 (16 μM). As embodied herein, N=6 for each phenylalanine concentration; N=3 for each nonspecific target concentration. Standard errors of the means for each datum were too small to be displayed in some cases; RFU is relative fluorescence units.

Figure 23A:
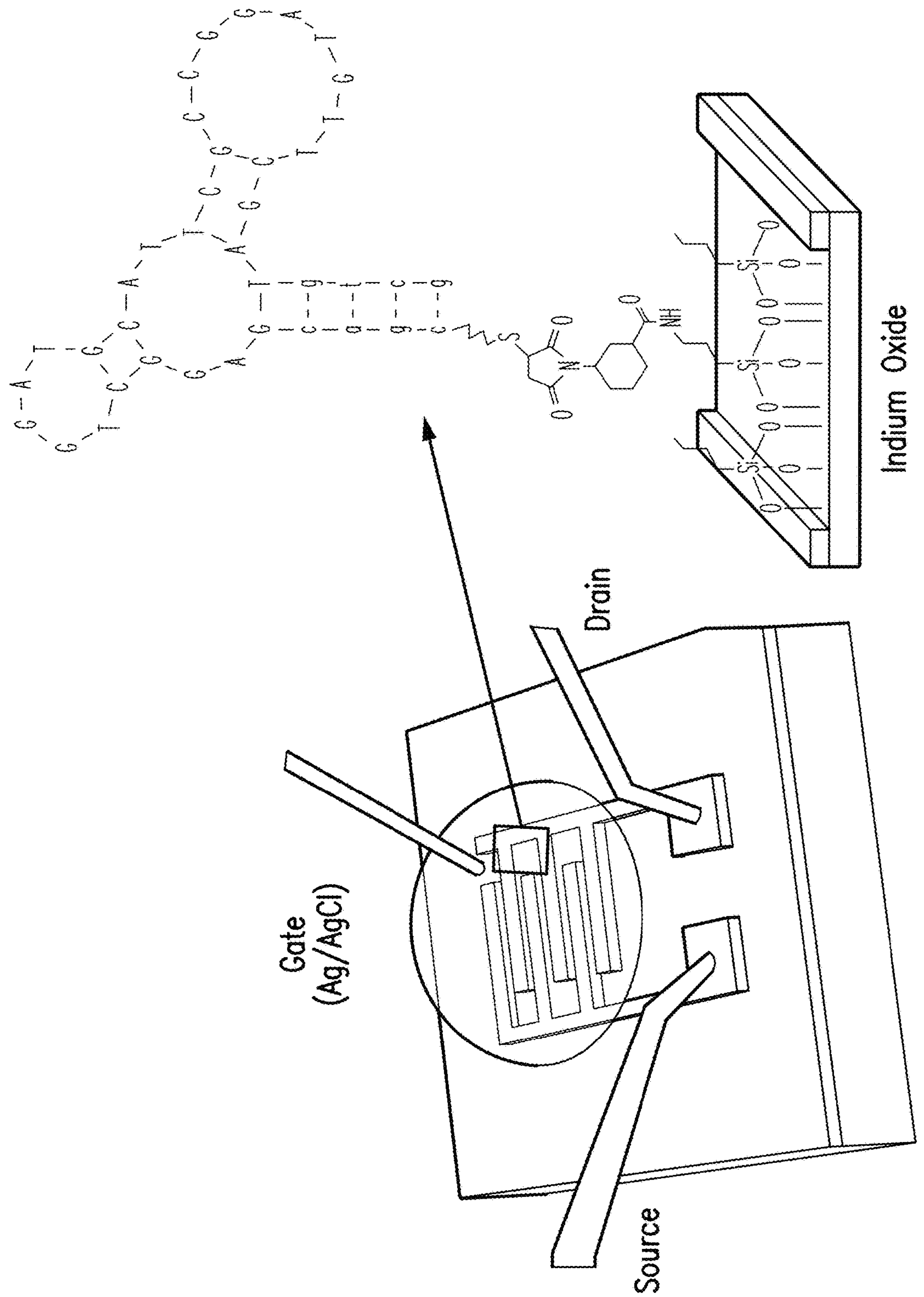
FIGS. 23A-E provide (23A) schematic illustrations of an example FET platform and surface chemistry, (23B) calibrated responses of Phe aptamers 1, 2, and 3, (23C) transfer curves for Phe 3 aptamer-FETs, (23D) circular dichroism spectra of Phe 3, and (23E) calibrated responses of the Phe 3 aptamer.

Each of the phenylalanine-specific aptamers was attached to the semiconducting channels of FETs for electronic detection of phenylalanine (FIG. 23A). Thiolated aptamers were attached to $In_2O_3$ surfaces via self-assembled silanes using m maleimidobenzoyl-N-hydroxysuccinimide as a crosslinker. Field-effect transistors were operated in a top-gated setup where the source-drain current ($I_{DS}$) was measured while sweeping the gate voltage ($V_{GS}$) during target exposure. Reorganization of surface-tethered negatively charged oligonucleotide aptamer backbones occurred in close proximity to metal-oxide semiconducting surfaces upon target capture to gate FET conductances and to result in target-concentration-dependent current changes under physiological ionic conditions.

Figure 23B:
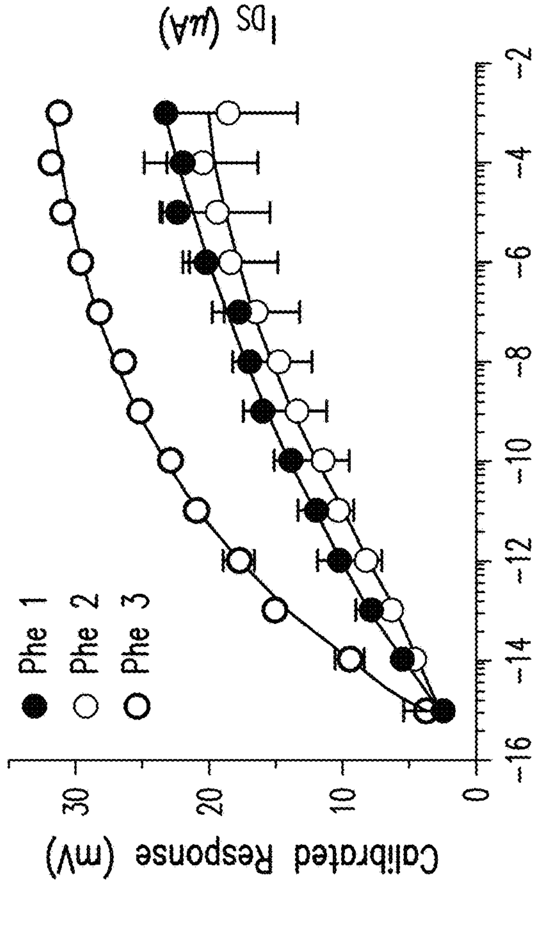

Phenylalanine-aptamer-FETs showed a wide range of concentration-dependent responses to phenylalanine (fM-mM) in 1×Ringer's solution, which mimics the ionic composition of the plasma fraction of human blood (FIG. 23B). Sensing in physiological buffers that are similar in terms of ion concentrations to the target biological matrix is important for evaluating oligonucleotide receptors because interactions with solution ions can result in alternate aptamer secondary structures and thus, differences in sensor sensitivities and selectivity. One of the aptamers recognizing phenylalanine complexed with Cp*Rh when attached to FETs was tested, as an example of the use of this type of aptamer. The Phe-Cp*Rh 2 aptamer showed similar responses to those of the direct phenylalanine aptamers (FIG. 28D), suggesting that metal complexation to increase sensitivity can be optional and direct phenylalanine detection can be sufficient in the context of FET sensors.

Figure 23C:
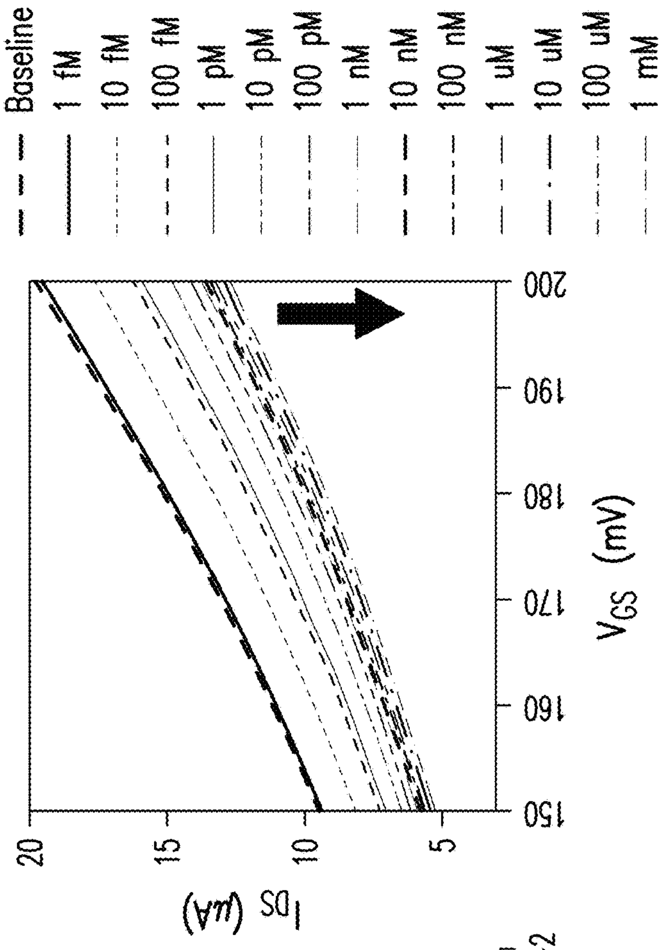
Figure 29B:
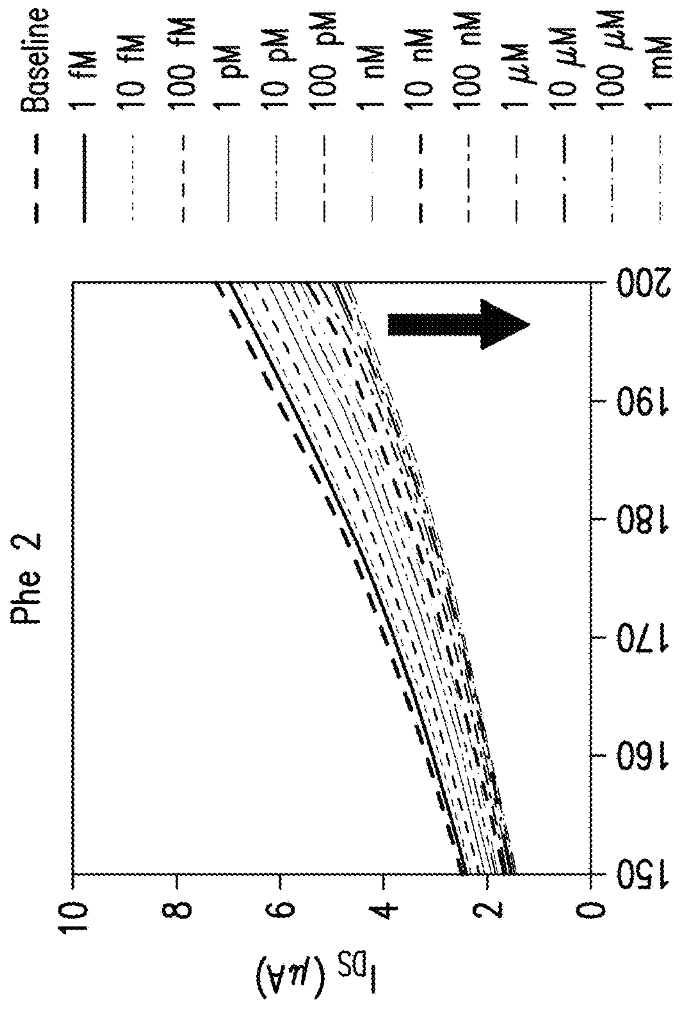
FIGS. 29A-B provide diagrams illustrating transfer characteristics (I-V curves) of field-effect transistors functionalized with the phenylalanine-specific aptamers (29A) Phe 1 and (29B) Phe 2 upon exposure to increasing concentrations of phenylalanine in 1×Ringer's solution.
Figure 29A:
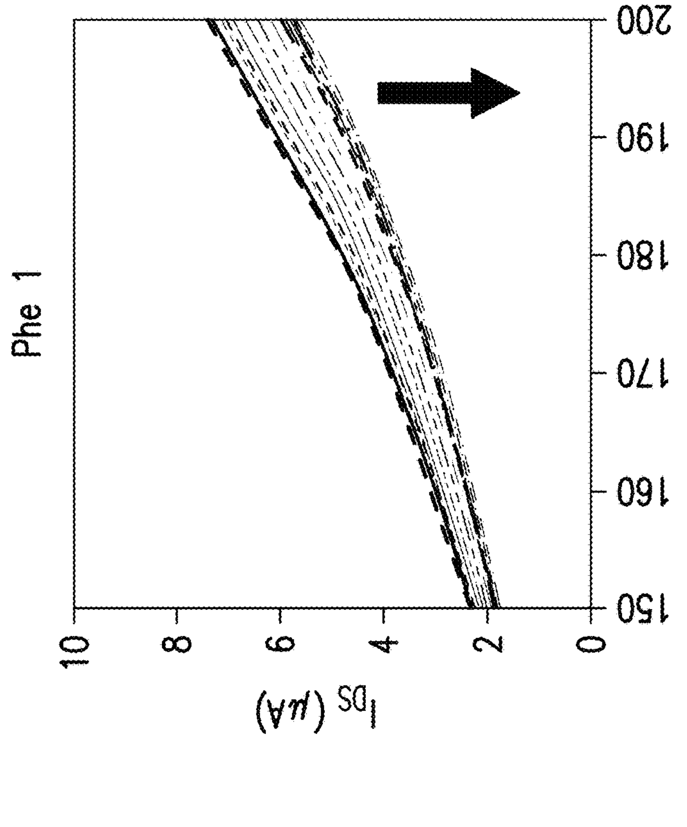

Target-concentration-dependent decreases in current were observed for FET transfer curves (IDS-$V_{GS}$ sweeps) for each of the three direct sensing aptamers (FIGS. 23C and 29). The decreases in FET transfer characteristics were observed here on n-type semiconductors to the dominant effect of negatively charged DNA aptamer backbones moving closer to the semiconductor channel surfaces and thereby gating the semiconductor upon target binding. Aptamer-FET small-molecule sensing is due to gating associated with the reorganization of charged DNA aptamer backbones, which can move charge either toward or away from the channel upon recognition, based at least in part on the aptamer of interest, and can be independent of the charge on the small-molecule targets.

Figure 23D:
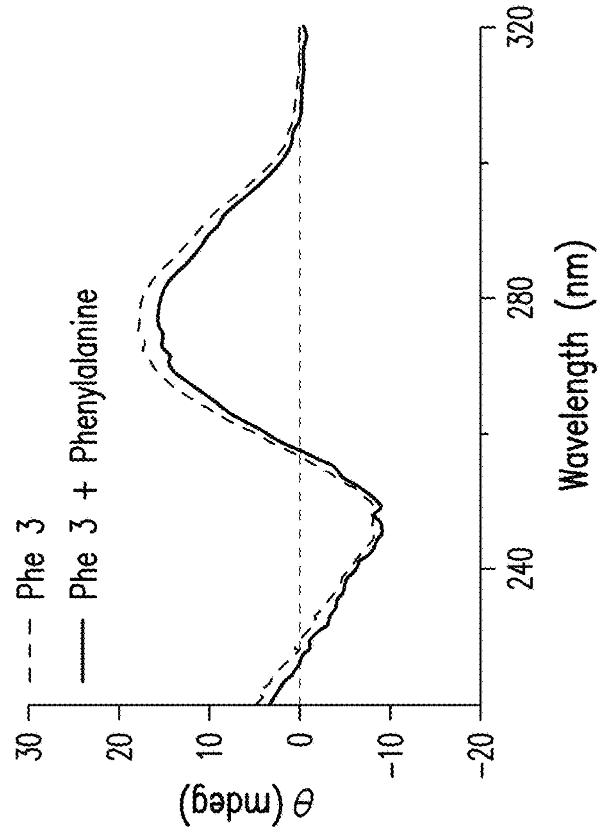
Figure 30A:
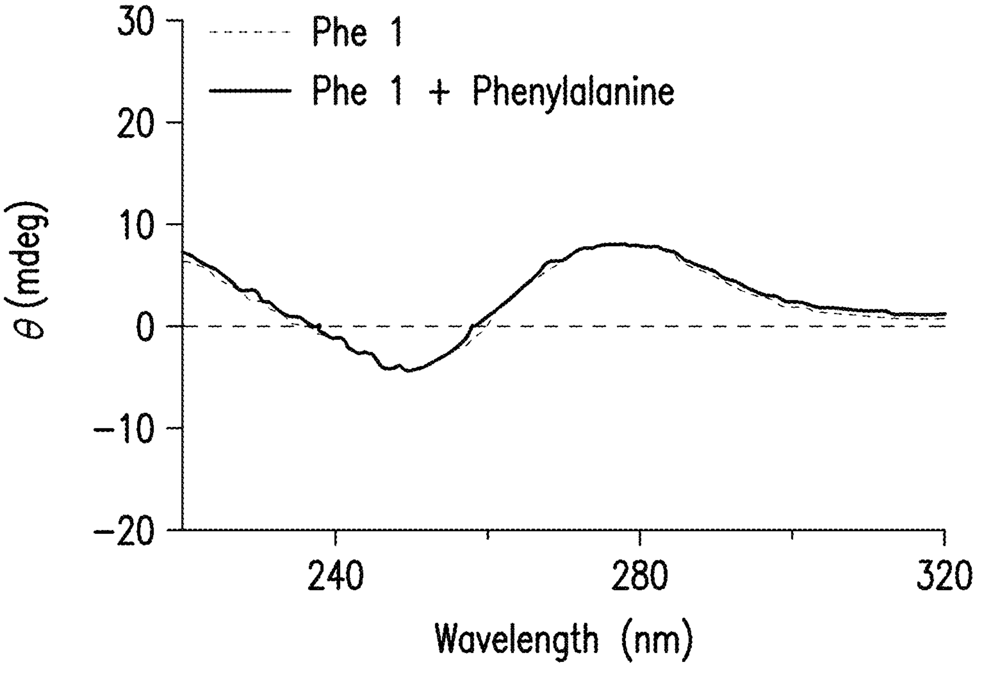
FIGS. 30A-B provide diagrams illustrating circular dichroism spectra of (30A) Phe 1 and (30B) Phe 2 before and after introduction of phenylalanine.
Figure 30B:
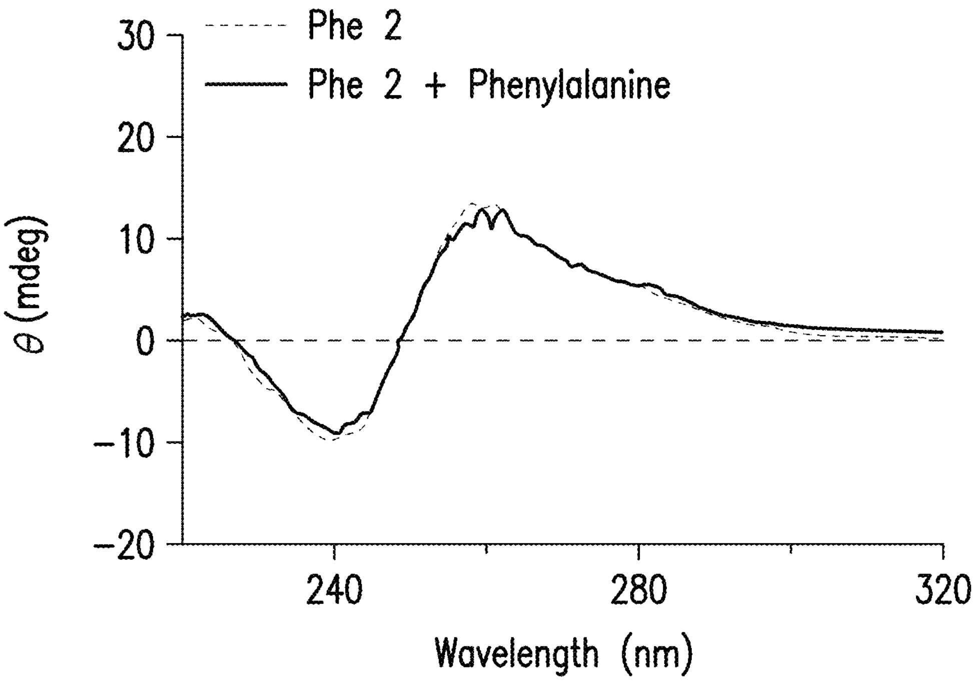

Circular dichroism (CD) spectroscopy was performed to investigate target-induced changes in aptamer secondary structures for the three phenylalanine direct-sensing aptamers, as CD spectral changes were associated with individual aptamer-FET responses. The spectra for Phe 3 showed a small but reproducible decrease in peak intensity at 280 nm after target capture, potentially corresponding to target-induced formation of hairpin motifs (FIG. 23D). Spectra showed negligible changes in peak positions or intensities for Phe 1 or Phe 2 upon association with phenylalanine (FIG. 30). A peak at 280 nm for Phe 1 can indicate the presence of B-DNA in the secondary structure, while a peak at 270 nm for Phe 2 can indicate the presence of a parallel G-quadruplex. Spectra shown in 30A-B are averages of N=2 spectra each. As such, the latter two aptamers can be considered not to form new secondary structural motifs upon target recognition, and as embodied herein, all three aptamers can primarily undergo adaptive target binding largely involving pre-formed secondary structures.

Figure 23E:
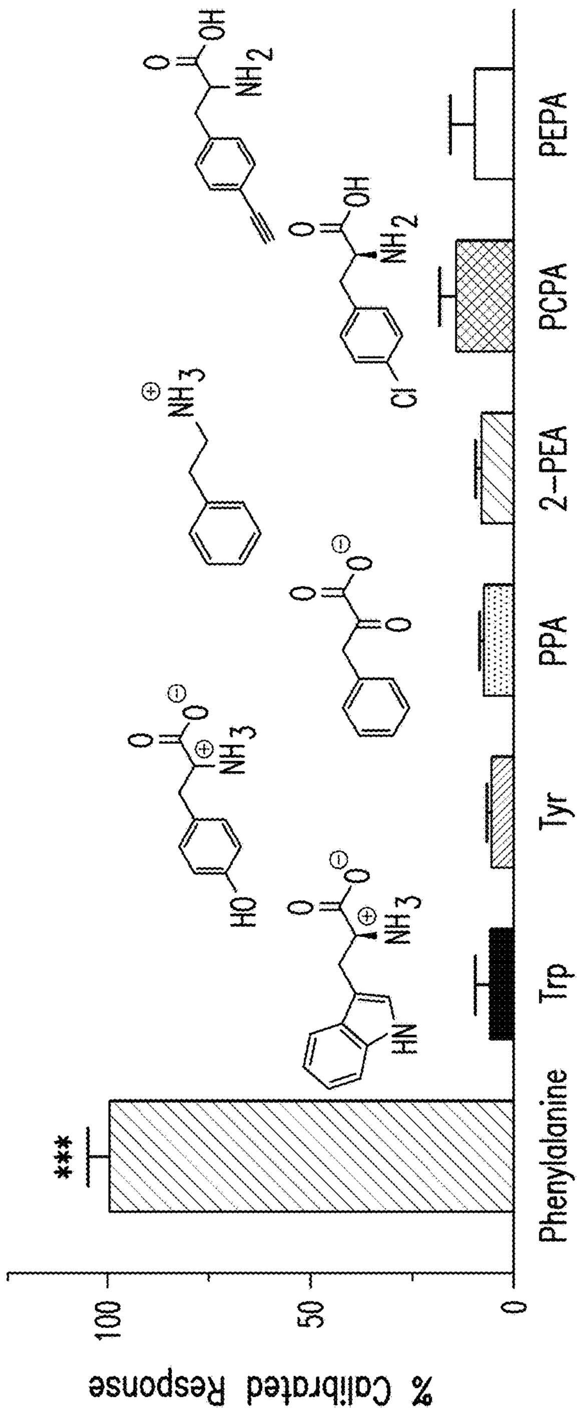
Figure 31:
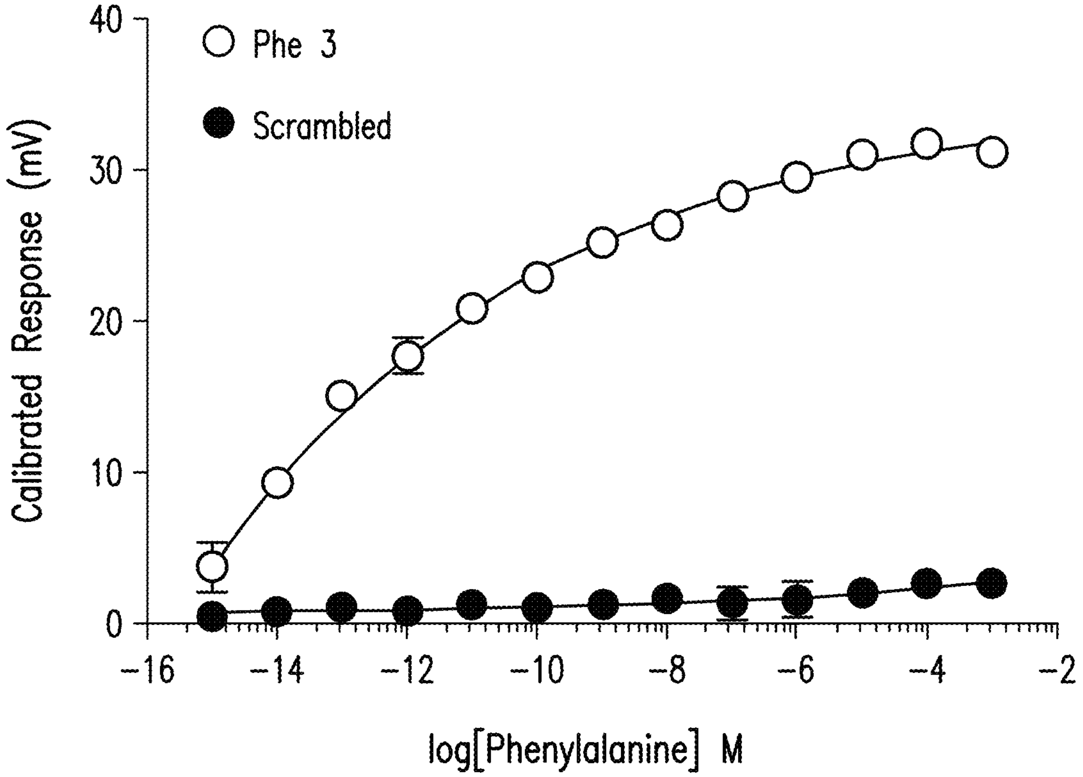
FIG. 31 provides a diagram illustrating example response curves of the disclosed field-effect transistor using a scrambled phenylalanine aptamer sequence.

Of the three direct-detection phenylalanine aptamers, Phe 3 showed the largest target-related responses and the smallest replication variability when integrated with FETs (FIG. 23B). The Phe 3 aptamer also showed the highest selectivity towards nonspecific targets compared to Phe 1 and Phe 2 in competitive fluorescence assays (FIG. 22C-E). To investigate selectivity on FETs, responses of Phe 3-aptamer-FETs to the aromatic amino acid tryptophan were measured, the phenylalanine metabolites tyrosine, phenylpyruvic acid, and 2 phenylethylamine, and the two phenylalanine analogs (FIG. 23E). Sensor responses upon exposure to 100 μM solutions of five of the nonspecific targets were <10% of the average response to an equivalent concentration of phenylalanine; responses to PCPA were 15% of the average phenylalanine response. As a further indication of selectivity, responses of FETs functionalized with a scrambled version of the Phe 3 sequence having the same numbers and types of nucleotides as the correct Phe 3 aptamer sequence but with a different predicted secondary structure were negligible (FIG. 31).

FIG. 23A shows schematic of the FET platform and surface chemistry. In this example, FETs were composed of 4-nm thin-film $In_2O_3$ as the channel material, with a 10-nm Ti adhesion layer and a 30-nm top Au layer patterned as interdigitated electrodes over the semiconductor layer. Sensing was performed by applying a source-drain bias voltage, sweeping the gate voltage with respect to a Ag/AgCl reference electrode in a solution-gated configuration, and measuring changes in source-drain currents. Thiolated aptamers were tethered to semiconductor surfaces using m-maleimidobenzoyl-N-hydroxysuccinimide ester to crosslink thiol groups to amine-terminated silanes, co-self-assembled with methyl-terminated silanes, which served as spacer molecules to adjust aptamer surface densities for target recognition. As shown in FIG. 23B, each of three phenylalanine aptamers attached to FETs (Phe 1, Phe 2, Phe 3) produced concentration-dependent responses in 1×Ringer's solution. FIG. 23C shows representative transfer (IDS-$V_{GS}$) curves for Phe 3 aptamer-FETs upon increasing phenylalanine concentrations and FIG. 23D shows circular dichroism spectra of Phe 3 in 1×Ringer's solution before and after introduction of phenylalanine (2 μM). Spectra shown are an average of N=3 spectra each. As shown in FIG. 23E, the Phe 3 aptamer, when incorporated into FETs, had negligible responses to nonspecific targets, including tryptophan (Trp), tyrosine (Tyr), phenylypyruvic acid (PPA), 2-phenylethylamine (2-PEA), para-chlorophenylalanine (PCPA), or para-ethynylphenylalanine (PEPA) compared to phenylalanine (all targets at 100 μM) [F (6, 10)=76; P<0.001]. Error bars, are standard errors of the means with N=3 for B, and N=3 for phenylalanine, PCPA, and PEPA and N=2 for Trp, Tyr, PPA, and 2-PEA in FIG. 23E. P value was P<0.001 vs all nonspecific targets.

Figure 24A:
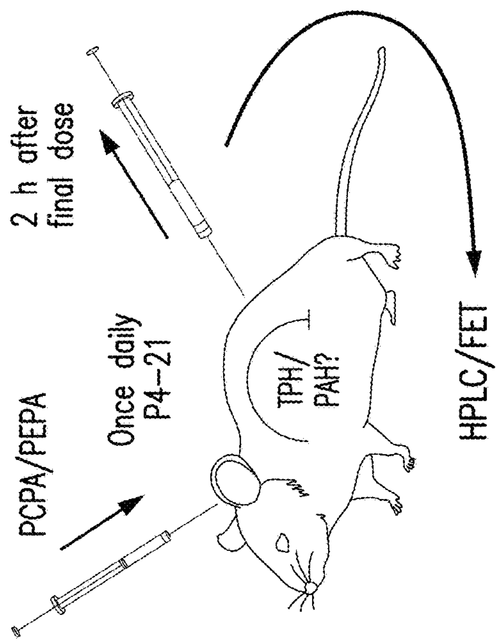
FIGS. 24A-C provide (24A) a schematic illustration of an example of an in vivo experimental design, (24B) measured serum phenylalanine concentrations from mice treated with PCPA, PEPA, or saline, and (24C) phenylalanine concentrations measured in mouse serum samples via aptamer-FETs vs. HPLC.

To investigate Phe 3-aptamer-FET detection of clinically relevant phenylalanine levels, phenylalanine was measured in serum (diluted with 1×Ringers) from mice injected daily with PCPA, PEPA, or saline during postnatal days 4-21 (FIG. 24A). This postnatal period in mice is the human developmental equivalent of the last trimester of pregnancy and the first postnatal year. This treatment period was selected to determine the impact of elevated phenylalanine levels on cortical axon development. Both para-substituted phenylalanine analogs inhibit tryptophan hydroxylase (TPH), which converts dietary tryptophan to 5 hydroxytryptophan. The latter is then decarboxylated to produce the neurotransmitter serotonin (5 hydroxytryptamine). However, PCPA can inhibit PAH activity, in addition to TPH, and PEPA can lack inhibitory effects on PAH.

Figure 24B:
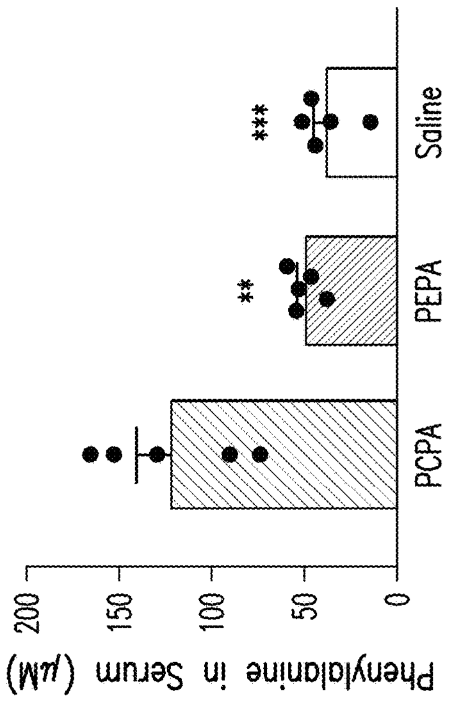
Figure 24C:
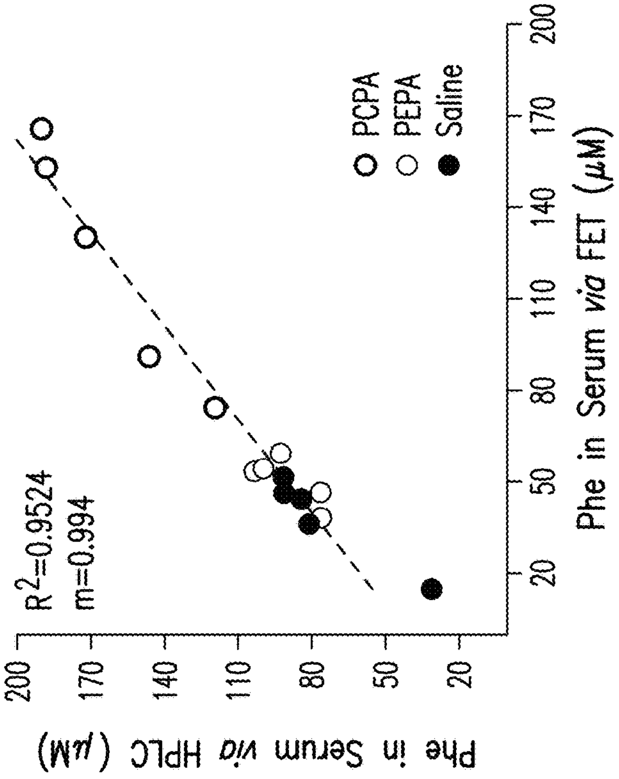
Figure 32:
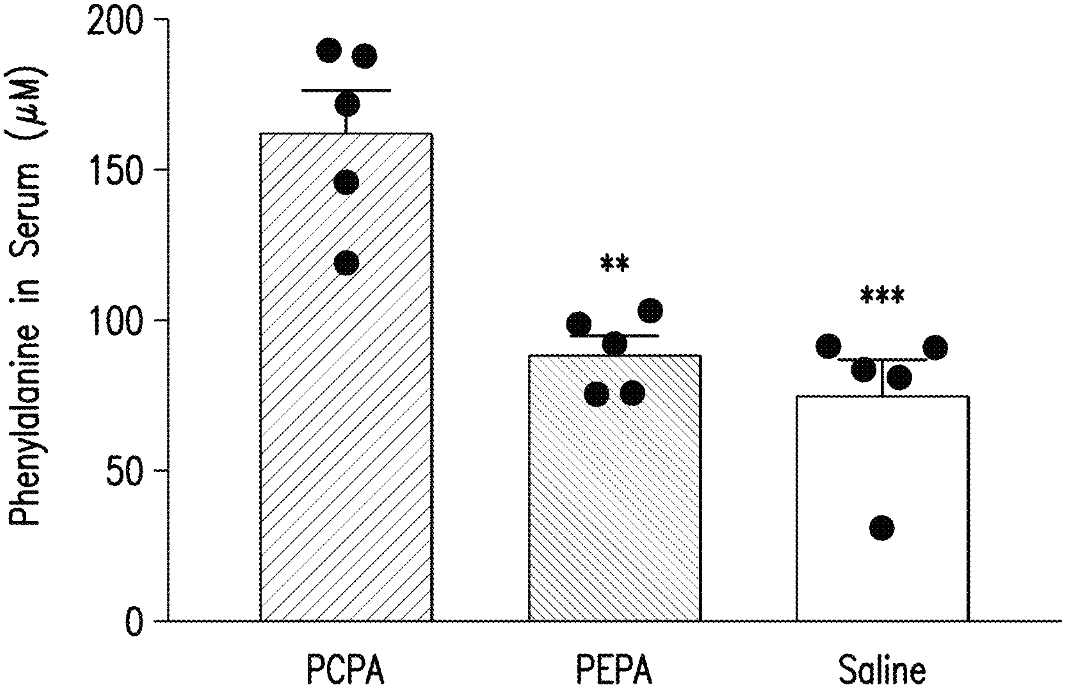
FIG. 32 provides a diagram illustrating measured phenylalanine levels in serum from mice treated with para-chlorophenylalanine (PCPA) or para-ethynylphenylalanine (PEPA).
Figure 33:
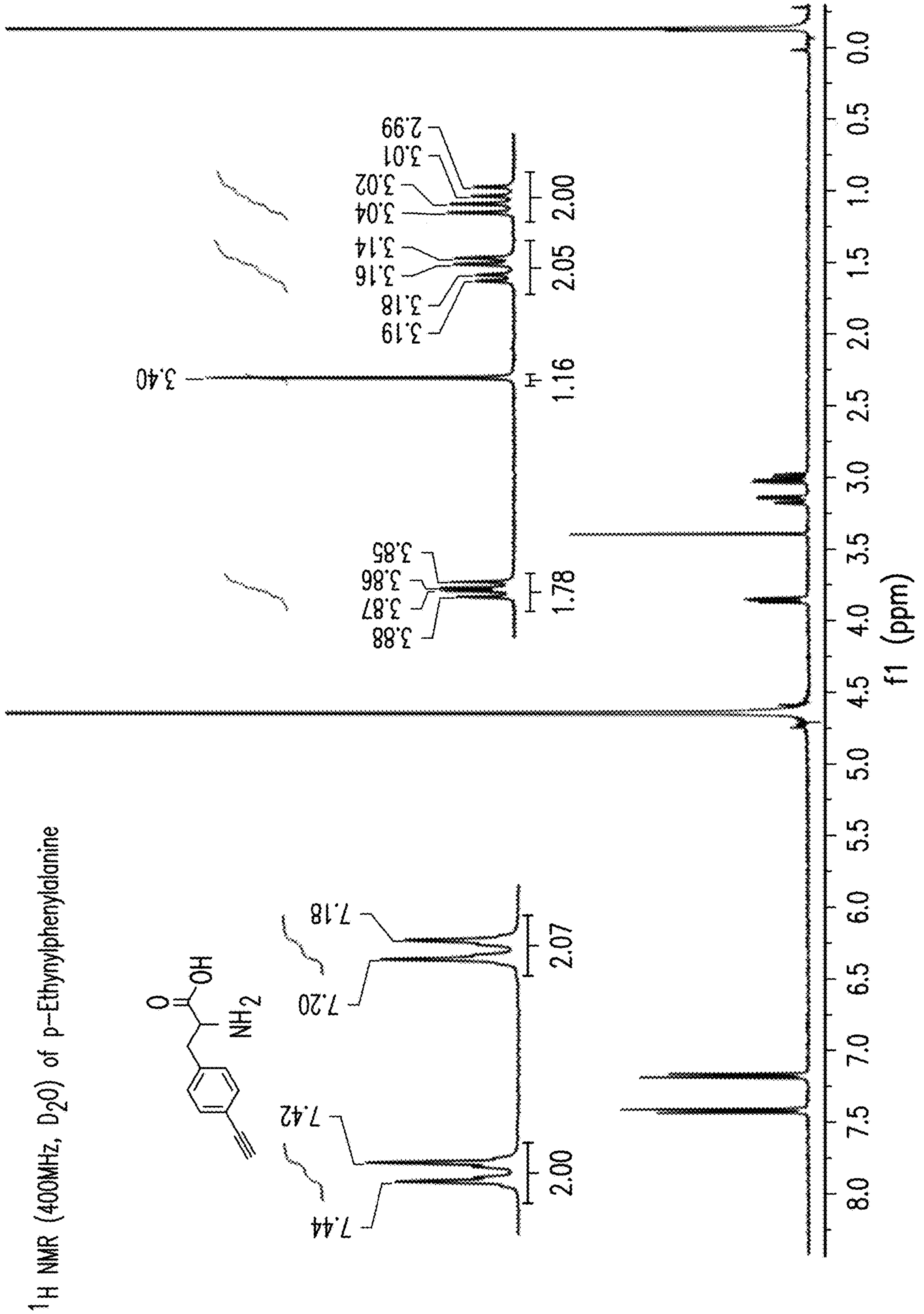
FIG. 33 provides a diagram illustrating a nuclear magnetic resonance spectrum of para-ethynylphenylalanine.

Mice receiving PCPA showed increases in serum phenylalanine levels (ca. 250%) compared to mice exposed to PEPA or saline (FIG. 24B). Phenylalanine concentrations in mouse serum samples were cross-validated via HPLC measurements (FIG. 32). Individual phenylalanine serum sample levels determined using aptamer-FETs were highly correlated with those measured by HPLC (R2=0.95; FIG. 24C). The slope of the regression line correlating phenylalanine levels determined by both methods was about 1 indicating that Phe 3-aptamer-FETs accurately reported phenylalanine levels.

Similar to phenylalanine, aptamer-FETs were used to determine serum glucose levels. Phenylalanine levels detected by aptamer-FETs in PCPA-treated mice (~120 μM) were at the low end of the range of serum levels in humans with modestly elevated phenylalanine, e.g., PKU patients adhering to dietary restrictions, and possibly, phenylalanine levels in some PKU carriers, i.e., individual with one mutant PAH allele (ca. one in 50 Caucasians).

FIG. 24A shows a schematic illustration of the in vivo experimental design. Mice were treated once per day with para-chlorophenylalanine (PCPA) or para-ethynylphenylalanine (PEPA) during postnatal days (P)4 21. These phenylalanine analogs inhibit tryptophan hydroxylase (TPH). Certain PCPA can also inhibit phenylalanine hydroxylase (PAH). Serum samples were collected 2 h after the final injection of each analog on P21. Phenylalanine concentrations were measured by Phe 3-aptamer-FETs and cross-correlated with high-performance liquid chromatography (HPLC) as a reference method. As shown in FIG. 24B, mice treated with PCPA had modestly elevated serum phenylalanine concentrations compared to mice treated with PEPA or saline [F(2,12)=17.3; P<0.01]. Data points depict levels from individual animals. Error bars are standard errors of the means with N=5 for each treatment group. P<0.01 vs PCPA; *P<0.001 vs PCPA. FIG. 24C shows a correlation of phenylalanine concentrations measured in mouse serum samples via aptamer-FETs compared to HPLC with the corresponding linearity index (R2) and regression slope (m). P=0.762 (Run's test), deviation from linearity is not significant.

Phenylalanine has been measured using chromatographic, plasmonic, and fluorimetric techniques. These methods, however, involve specialized laboratory instrumentation and some require complex extractions. As such, they can be unsuitable for rapid point-of-care or at-home monitoring. Certain colorimetric, paper-based detection platforms can be utilized for PKU diagnosis and monitoring in low-resource settings, but can involve the use of enzyme-based recognition elements, which can lose activity over time due to denaturation. Phenylalanine sensing has involved electrochemical signal transduction or a conductive electrode design involving graphene oxide, which can be defect prone and synthetically heterogeneous. Additionally, an electrochemical strategy can involve phenylalanine capture via a RNA phenylalanine aptamer (KD~120 μM) followed by phenylalanine oxidation at gold electrodes. The DNA aptamers reported herein have 10-fold higher affinities for phenylalanine, e.g., KD~12 μM (FIG. 22C-E). Moreover, aptamers including DNA instead of RNA can have intrinsic advantages, including in terms of higher stability when exposed to biological matrices, such as serum.

FIG. 31 shows results of field-effect transistor sensing of phenylalanine using a scrambled sequence, e.g., the same numbers and types of nucleotides as Phe 3, but with a different predicted secondary structure. Negligible responses were observed over all concentrations tested for the scrambled sequence. Data for the correct Phe 3 sequence are presented for reference. Error bars are standard errors of the means with N=3 for Phe 3 and N=2 for the scrambled sequence.

Three new DNA-based receptors that recognize the biochemically and medically important target phenylalanine were identified. Two aptamers that recognize a phenylalanine-organometallic complex (Phe-Cp*Rh) were also isolated. The direct-binding phenylalanine aptamers (and one of the Phe-Cp*Rh aptamers) were integrated with thin-film metal-oxide field-effect transistors (FETs). Phenylalanine-FET sensors detected phenylalanine under physiological ionic conditions over six orders of magnitude with fM detection limits. Sensors incorporating the Phe 3 aptamer showed improved selectivity for phenylalanine compared to similarly structured aromatic amino acids and metabolites. The accuracy and precision of these FET sensors were improved compared to a known laboratory method.

The ability to differentiate clinically relevant differences in serum phenylalanine levels with a minimal dilution demonstrates the capability of aptamer-FETs for use in electronic point-of-care devices for PKU diagnosis and management. Aptamer/device sensitivities can be tuned by altering the surface chemistries of the semiconducting channel or rationally modifying aptamer sequences can eliminate the need for serum dilution. Certain aptamer-FET sensors can be used for in vivo monitoring to investigate transiently induced or permanently maintained (through continuous administration of PCPA or via mice with constitutive reductions in PAH) elevations in phenylalanine. Rapid monitoring in PKU animal models would further illustrate how changes in PAH activity or diet impact temporally resolved phenylalanine levels.

DNA aptamers can thus be readily synthesized and the FET fabrication methods used herein are straightforward and easily scaled up. As embodied herein, miniaturized, e.g., varied aspect ratios, and nanostructured, e.g., increased surface-to-volume ratios, $In_2O_3$ thin-film FETs using low-cost soft-lithographic methods are described. Additionally, as embodied herein, the disclosed $In_2O_3$ FETs on flexible substrates demonstrated capabilities to tailor device performance and architectures for specific applications. Translation for at-home monitoring can involve development of FET-measurement technology, e.g., instrumentation, that is reliable, inexpensive, with few technological constraints, and that can be easily operated by users. As embodied herein, aptamer-FETs have direct potential for point-of-care phenylalanine determination for phenylketonuria disease management and monitoring of other at-risk populations.

In addition to the various embodiments depicted and claimed, the disclosed subject matter is also directed to other embodiments (e.g., other targets, other sensing environments) having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed is:

1. A sensor for detecting a target molecule in a sample comprising, a field-effect transistor comprising a semiconductor channel, an oligonucleotide attached to a surface of the semiconductor channel of the field-effect transistor via self-assembled silanes using a crosslinker in a first conformation and comprising a capture region and a stem region, wherein the stem region is positioned to transform a stem-loop structure of the oligonucleotide to a second conformation when the oligonucleotide binds to the target molecule.

2. The sensor of claim 1, wherein the oligonucleotide comprises an aptamer that includes a backbone, wherein the backbone is a neutral backbone, a nearly neutral backbone, or a negatively charged backbone, wherein at least about 25% of the backbone is negatively charged, wherein the transformed oligonucleotide is configured to change a conductance of the field-effect transistor, and wherein the sensor is positioned to provide chemically selective, and spatial and/or spatiotemporal information on the target molecules and their concentrations.

3. The sensor of claim 2, wherein the second conformation of the stem-loop structure repositions the backbone towards or away from a surface of the field-effect transistor, and wherein a negatively charged portion of the backbone repositions towards or away from a surface of the field-effect transistor.

4. The sensor of claim 2, wherein the aptamer is a stem-loop aptamer having a stem and a loop, wherein the loop comprises the capture region and the stem comprises the stem region, wherein the loop forms a binding pocket around the target molecule when the capture region binds to the target molecule, and wherein the loop comprises a secondary structure, wherein the secondary structure includes a base-paired structure that is configured to be formed by folding.

5. The sensor of claim 1, wherein the oligonucleotide further includes molecules that amplify the charge of the oligonucleotide, wherein the oligonucleotide is a non-binding oligonucleotide, wherein the oligonucleotide includes particles, dendrimers, organic species which have less than 1000 D molecular weight, fragments that attract other species, or combinations thereof, and wherein the oligonucleotide stem-loop structure is configured to be transformed into the second conformation within one or more Debye lengths from the surface, wherein the Debye length ranges from about 0.5 nm to about 3 nm in physiological conditions.

6. The sensor of claim 1, wherein the field-effect transistor comprises a metal oxide, wherein the field-effect transistor is a quasi-two-dimensional or two-dimensional FET, and wherein the field-effect transistor comprises an organic conducting polymer, a carbon material, or a combination thereof, wherein the carbon material includes a carbon nanotube or graphene.

7. The sensor of claim 1, wherein a multiplicity of sensors is configured to be used for multiplexed detection of one or more target molecules in the sample over a broader concentration range than a detectable target concentration range by a single sensor.

* * * * *

SEQUENCE LISTING

```
<160> NUMBER OF SEQ ID NOS: 98

<210> SEQ ID NO 1
<211> LENGTH: 15
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 1
acaatgtctc gttgt 15

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaagctgatt c 11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agtgtccatt g 11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agtgtccttt g 11

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acgaccgtgt gtgttgctct gtaacagtgt ccattgtcgt 40

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctctcgggac gaccgtgtgt gttgctctgt aacagtgtcc attgtcgtcc c 51

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
ctctcgggac gaccgtgtgt ggtagagtcg tcgggctcta acagtgtcct ttgtcgtccc 60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
ctctcgggac gaccgtgtgt gacgtgcgcc gtggggaacg tcagtgttct ttgtcgtccc 60

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
ctctcgggac gaccgtgtgt cgacttagag tcgagtgtcc tttgtcgtcc c 51

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
ctctcgggac gaccgtgtgt tgcaattctt gcaagtgttc tttgtcgtcc c 51

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (9)..(12)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other

<400> SEQUENCE: 11
nncgtgtgnn nngtgtccat tnn 23

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide -continued

<400> SEQUENCE: 12
cgacctggtg tgttgctctg taacagtgtc tattgtcg 38

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
ctctcgggac gaccgcgttt cccaagaaag caagtattgg ttggtcgtcc c 51

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
ctctcgggac gaccggtggg ggttcttttt caggggaggt acggtcgtcc c 51

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
ctctcgggac gacgaggctg gatgcattcg ccggatgttc gatgtcgtcc c 51

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gaccggtggg ggttcttttt caggggaggt acggtc 36

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(8)
<223> OTHER INFORMATION: a, c, t, g, unknown or other
<220> FEATURE:
<221> NAME/KEY: modified_base
<222> LOCATION: (13)..(16)
<223> OTHER INFORMATION: a, c, t, g, unknown or other
<220> FEATURE:
<221> NAME/KEY: modified_base
<222> LOCATION: (18)..(20)

<223> OTHER INFORMATION: a, c, t, g, unknown or other
<220> FEATURE:
<221> NAME/KEY: modified_base
<222> LOCATION: (24)..(26)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other

<400> SEQUENCE: 17
nncgnnnncc aannnngnnn gtannngtnn 30

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
gaccgcgttt cccaagaaag caagtattgg ttggtc 36

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
accgcgtttc ccaagaaagc aagtattggt tggtc 35

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (10)..(13)
<223> OTHER INFORMATION: a, c, t, g, unknown or other
<220> FEATURE:
<221> NAME/KEY: modified_base
<222> LOCATION: (19)..(22)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other

<400> SEQUENCE: 20
nngtgggggn nnnttttcnn nngaggtann 30

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
ctctcgggac gaggctggat gcattcgccg gatgttcgat gtcgtccc 48

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
cgacgaggct ggatgcattc gccggatgtt cgatgtcg 38

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (32)..(34)
<223> OTHER INFORMATION: a, c, t, g, unknown or other

<400> SEQUENCE: 23
nnnaggctgg atgcattcgc cggatgttcg annn 34

<210> SEQ ID NO 24
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
ctctcgggac gacgtggtgt gggagaaaga attttcattg ggtaggggg tcgtccc 57

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
acgacgtggt gtgggagaaa gaattttcat tggggtaggg ggtcgt 46

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (15)..(16)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other

<400> SEQUENCE: 26
nngtggtgtg ggagnncatt ggggtagggg nn 32

<210> SEQ ID NO 27
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ctctcgggac gacgccagtt tgaaggttcg ttcgcaggtg tggagtgacg tccc 54

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
cgacgccagt ttgaaggttc gttcgcaggt gtggagtgac gtcg 44

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (10)..(12)
<223> OTHER INFORMATION: a, c, t, g, unknown or other
<220> FEATURE:
<221> NAME/KEY: modified_base
<222> LOCATION: (19)..(21)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 29
ngccagtttn nnggttcgnn ngcaggtgtg gagtgacn 38

<210> SEQ ID NO 30
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ctctcgggac gactgcagcc tggggttgtg gggggtaggg gaggtctgag tcgtccc 57

<210> SEQ ID NO 31

<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
cgactgcagc ctggggttgt gggggtagg ggaggtctga gtcg 44

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 32
ntgcagcctg gggttgtggg gggtagggga ggtctgan 38

<210> SEQ ID NO 33
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
ctctcgggac gaccacacag aggcacaact cgcaggagca aagcggcagg tcgtccc 57

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
cgaccacaca gaggcacaac tcgcaggagc aaagcggcag gtcg 44

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (19)..(21)
<223> OTHER INFORMATION: a, c, t, g, unknown or other
<220> FEATURE:
<221> NAME/KEY: modified_base
<222> LOCATION: (31)..(33)
<223> OTHER INFORMATION: a, c, t, g, unknown or other
<220> FEATURE:

<221> NAME/KEY: modified_base
<222> LOCATION: (37)..(38)
<223> OTHER INFORMATION: a, c, t, g, unknown or other

<400> SEQUENCE: 35
nnacacagag gcacaactnn naggagcaaa nnngcann 38

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
ctctcgggac gacggggagt tagcatgacg gcaactttag tacttcgtcc c 51

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
cgacggggag gagttagcat gacggcaact ttagtacttc gtcg 44

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 38
nggggaggan ntttagtact tcn 23

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
ctctcgggac gaccacttca gacgctcaac gtttggggag gcacggcagg tcgtccc 57

<210> SEQ ID NO 40
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
cgaccacttc agacgctcaa cgtttgggga ggcacggcag gtcg 44

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(11)
<223> OTHER INFORMATION: a, c, t, g, unknown or other
<220> FEATURE:
<221> NAME/KEY: modified_base
<222> LOCATION: (19)..(25)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 41
ncacnnnnnn ngctcaacnn nnnnngaggc acggcagn 38

<210> SEQ ID NO 42
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
ctctcgggac gacgccagtt tgaaggttcg ttcgcaggtg tggagtgacg tcgtccc 57

<210> SEQ ID NO 43
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
ctctcgggac gacggggagg agttagcatg acggcaactt tagtacttcg tcgtccc 57

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
ctctcgggac gactggtagg cagatagggg aagctgattc gatgcgtggg tcgtccc 57

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgactggtag gcagataggg gaagctgatt cgatgcgtgg gtcg 44

<210> SEQ ID NO 46
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (8)..(10)
<223> OTHER INFORMATION: a, c, t, g, unknown or other
<220> FEATURE:
<221> NAME/KEY: modified_base
<222> LOCATION: (18)..(20)
<223> OTHER INFORMATION: a, c, t, g, unknown or other
<220> FEATURE:
<221> NAME/KEY: modified_base
<222> LOCATION: (26)..(28)
<223> OTHER INFORMATION: a, c, t, g, unknown or other
<220> FEATURE:
<221> NAME/KEY: modified_base
<222> LOCATION: (31)..(33)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 46
ntggtagnnn gatagggnnn gctgannnga nnngtggn 38

<210> SEQ ID NO 47
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctctcgggac gactggtagg caacagggga agggagttct gcgtacgtgg gtcgtccc 58

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cgactggtag gcaacagggg aagggagttc tgcgtacgtg ggtcg 45

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (18)..(19)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other

<400> SEQUENCE: 49
ntggnaggna acaggggnng ggagnnctnc gtncgtggn 39

<210> SEQ ID NO 50
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
ctctcgggac gacaggggca tatatagtct agggtttggt gtgggtagtg tcgtccc 57

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
cgacaggggc atatatagtc tagggtttgg tgtgggtagt gtcg 44

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 52
naggggcata tatagtctag ggtttggtgt gggtagtn 38

<210> SEQ ID NO 53
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
ctctcgggac gactggtagg cagcagggga agtaggcgtg tcctcgtggg tcgtccc 57

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
cgactggtag gcagcagggg aagtaggcgt gtcctcgtgg gtcg 44

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 55
ntggtaggca gcaggggaag taggcgtgtc ctcgtggn 38

<210> SEQ ID NO 56
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
ctctcgggac gaccagtagg ggatccacag tgaggggttt gtatgggtgg tcgtccc 57

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
gaccagtagg ggatccacag tgaggggttt gtatgggtgg tc 42

```
<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (11)..(14)
<223> OTHER INFORMATION: a, c, t, g, unknown or other
<220> FEATURE:
<221> NAME/KEY: modified_base
<222> LOCATION: (31)..(34)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other

<400> SEQUENCE: 58

nagtagggga nnnncagtga ggggtttgta nnnntn                              36


<210> SEQ ID NO 59
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

ctctcgggac gacggaggtg gtgtcttgga cagtggtatt cgcagttgcg tcgtccc       57


<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

cgacggaggt ggtgtcttgg acagtggtat tcgcagttgc gtcg                     44


<210> SEQ ID NO 61
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (10)..(20)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 61

nggaggtggn nnnnnnnnnn gtggtattcg cagttgcn                            38
```

-continued

<210> SEQ ID NO 62
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
ctctcgggac gacagagacg gggtgcttac ttggttcagg ggagtcgacg tcgtccc 57

<210> SEQ ID NO 63
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
acgacagaga cggggtgctt acttggttca ggggagtcga cgtcgt 46

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: modified_base
<222> LOCATION: (33)..(35)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other

<400> SEQUENCE: 64
nnagannngg ggtgcttact tggttcaggg gannngacnn 40

<210> SEQ ID NO 65
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
gacgacggtg gccttaatag atagatgata ttcttatatg tgtgaggggt ggtcgtc 57

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66

-continued gacgacggtg gcctatattg gtatgtatga agaatagaac tattaggggg tgtc 54

<210> SEQ ID NO 67
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
cgacggtggc ctattaaata gctttagttt aagaaaagta ataggggtg tcg 53

<210> SEQ ID NO 68
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
ctctcgggac gacggtggcc tattaagtag ctttagttca agaaaagtaa tagggggtgt 60
cgtccc 66

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
gacggtggcc tatattggta tgtatgaaga atagaactat tagggggtgt c 51

<210> SEQ ID NO 70
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
cgacggtggc ctattaagta gctttagttc aagaaaagta ataggggtg tcg 53

<210> SEQ ID NO 71
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(48)
<223> OTHER INFORMATION: a, c, t, g, unknown or other

<400> SEQUENCE: 71
ggaggctctc gggacgacnn nnnnnnnnnn nnnnnnnnnn nnnnnnnngt cgtcccgatg 60
ctgcaatcgt aa 72

<210> SEQ ID NO 72
<211> LENGTH: 79
<212> TYPE: DNA

-continued

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(54)
<223> OTHER INFORMATION: a, c, t, g, unknown or other

<400> SEQUENCE: 72
ggaggctctc gggacgacnn nnnnnnnnnn nnnnnnnnnn nnnnnnnnnn nnnngtcgtc     60
ccgcctttag gatttacag                                                  79

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggaggctctc gggacgac                                                   18

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ttacgattgc agcatcggga cg                                              22

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctgtaaatcc taaaggcggg acgac                                           25

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gtcgtcccga gagccata                                                   18

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gactggtagg cagatagggg aagctgattc gatgcgtggg tc                        42

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cgaccgtgtg tgtattctat acagtgtcca ttgtcg 36

<210> SEQ ID NO 79
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cgtcgtcccg agag 14

<210> SEQ ID NO 80
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gtcgtcccga gag 13

<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggtcgtcccg agag 14

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agtacgtcga tgctcgatca gtgggctagg tgcgtagcgg tctg 44

<210> SEQ ID NO 83
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cccgggaatt ccggaattgg ggcaattgat gagggggtca tggg 44

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
tttgaggtca atcccggttt aggccccaag tttgcgttgt 40

<210> SEQ ID NO 85
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
gtggggactt ttcggtataa gggcattggg aaattcggtg gaggga 46

<210> SEQ ID NO 86
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
ctctcgggac gacacagcgt gagccaacta attagtgcgt attgttcgtc cc 52

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
tgtcgtcccg agag 14

<210> SEQ ID NO 88
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
ctctcgggac gaccacggga tatcttcagg atggtggtaa ctggtcgtcc c 51

<210> SEQ ID NO 89
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
attgctattc accggcgcgg ggctggggca tcggtaat 38

```
<210> SEQ ID NO 90
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90

cgacacagcg tgagccaact aattagtgcg tattgtcg                             38


<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91

gtcgtcccga gagcc                                                      15


<210> SEQ ID NO 92
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(51)
<223> OTHER INFORMATION: a, c, t, g, unknown or other
<220> FEATURE:
<221> NAME/KEY: misc_feature
<222> LOCATION: (16)..(51)
<223> OTHER INFORMATION: This region may encompass 30-36 nucleotides

<400> SEQUENCE: 92

ggctctcggg acgacnnnnn nnnnnnnnnn nnnnnnnnnn nnnnnnnnnn ngtcgtccc      59


<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(23)
<223> OTHER INFORMATION: a, c, t, g, unknown or other

<400> SEQUENCE: 93

ggctctcggg acgacnnnnn nnngtcgtcc c                                    31


<210> SEQ ID NO 94
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94

gactggtagg cagatagggg aagctgattc gatgcgtggg tc                        42


<210> SEQ ID NO 95
<211> LENGTH: 36
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95

cgaccgtgtg tgtattctat acagtgtcca ttgtcg                            36


<210> SEQ ID NO 96
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96

cgggacgacc g                                                        11


<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97

ttgtcgtccc g                                                        11


<210> SEQ ID NO 98
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98

cgacacagcg tgagccaact aattagtgcg tattatcg                          38
```